United States Patent
Barnwell et al.

(10) Patent No.: US 7,217,708 B2
(45) Date of Patent: *May 15, 2007

(54) 3,7-DIAZABICYCLO [3.3.1] FORMULATIONS AS ANTI-ARRHYTHMIC COMPOUNDS

(75) Inventors: Neil Barnwell, Leichestershire (GB); Annika Björe, Mölndal (SE); Lal Cheema, Leicestershire (GB); David Cladingboel, Leichestershire (GB); Adam Herring, Leicestershire (GB); Karin Lövqvist, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 430 days.

This patent is subject to a terminal disclaimer.

(21) Appl. No.: 10/474,592

(22) PCT Filed: Apr. 12, 2002

(86) PCT No.: PCT/SE02/00725

§ 371 (c)(1),
(2), (4) Date: Oct. 10, 2003

(87) PCT Pub. No.: WO02/083688

PCT Pub. Date: Oct. 24, 2002

(65) Prior Publication Data

US 2004/0143000 A1    Jul. 22, 2004

(30) Foreign Application Priority Data

Apr. 12, 2001    (SE) .................................... 0101327

(51) Int. Cl.
*C07D 498/08*    (2006.01)
*A61K 31/5386*    (2006.01)
(52) U.S. Cl. ..................................... 514/230.5; 544/74
(58) Field of Classification Search .................. 544/74; 514/230.5

See application file for complete search history.

(56) References Cited

U.S. PATENT DOCUMENTS 6,559,143 B1 *    5/2003    Bjore et al. .............. 514/230.5

FOREIGN PATENT DOCUMENTS

| EP | 0 308 843 A2 | 9/1988 |
|---|---|---|
| WO | WO-91/07405 A1 | 5/1991 |
| WO | WO-99/31100 A1 | 6/1999 |
| WO | WO-00/77000 A1 | 12/2000 |
| WO | WO-01/28992 A2 | 4/2001 |

OTHER PUBLICATIONS

DeRuiter, J., et al., "Synthesis and in Vitro Aldose Reductase Inhibitory Activity of Compounds Containing an N-Acylglycine Moiety," J. Med. Chem.., 32, 1033-1038 (1989).
Dudley, K., et al., "Chemical Studies of Potential Relevance to Penicillin Hypersensitivity. The Synthesis of DL-2 Phenoxymethylpenicillenic Acid and of DL-2-(2,6-Dimethoxyphenyl)penicillenic Acid(1)," J. Heterocyclic Chem., 10, 935-941 (1975).
Ginzel, K., et al., "Indirect Electrochemical a-Methoxylation of N-Acyl and N-Carboalkoxy a-Amino Acid Esters and Application as Cationic Glycine Equivalents," Tetrahedron, 45(6), 1691-1701 (1989).
Davis, F., et al., "Asymmetric Synthesis of 2H-Azirine 2-Carboxylate Esters," J. Org. Chem., 64, 8929-8935 (1999).
Paolo, C., "Swelling-controlled release in hydrogel matrices for oral route," Advanced Drug Delivery Reviews, 11, 37-57 (1993).
Paudler et al., "3,7-Disubstituted Octahydro-1,5-diazocines. Their Conversion into Tetrahydro-1,5-diazocines and into Ring-Contracted Products," J. Org. Chem. 32:2425-2430 (1967).

* cited by examiner

*Primary Examiner*—Kahsay Habte
(74) *Attorney, Agent, or Firm*—Christer Hallgren Pepper Hamilton LLP

(57) ABSTRACT

There is provided substantially crystalline forms of 4-({3-[7-(3,3-dimethyl-2-oxobutyl)    -9-oxa-3,7-diazabicyclo [3.3.1]non-3-yl]propyl}amino)benzo-nitrile; tert-butyl 2 -{7-[3-(4-cyanoanilino)propyl]-9-oxa-3,7-diazabicyclo-[3.3.1]non-3-yl}ethylcarbamate; tert-butyl 2-{7-[4-(4-cyanophenyl)butyl]-9-oxa-3,7-diazabicyclo[3.3.1]non-3-yl}ethylcarbamate; or tert-butyl 2-{7-[2S)-3-(4-cyanophenoxy)-2-hydroxypropyl]-9-oxa-3,7-diazabicyclo-[3.3.1]non-3-yl}ethylcarbamate and pharmaceutically-acceptable salts thereof, which compounds are useful in the treatment of cardiac arhythmias.

71 Claims, 23 Drawing Sheets

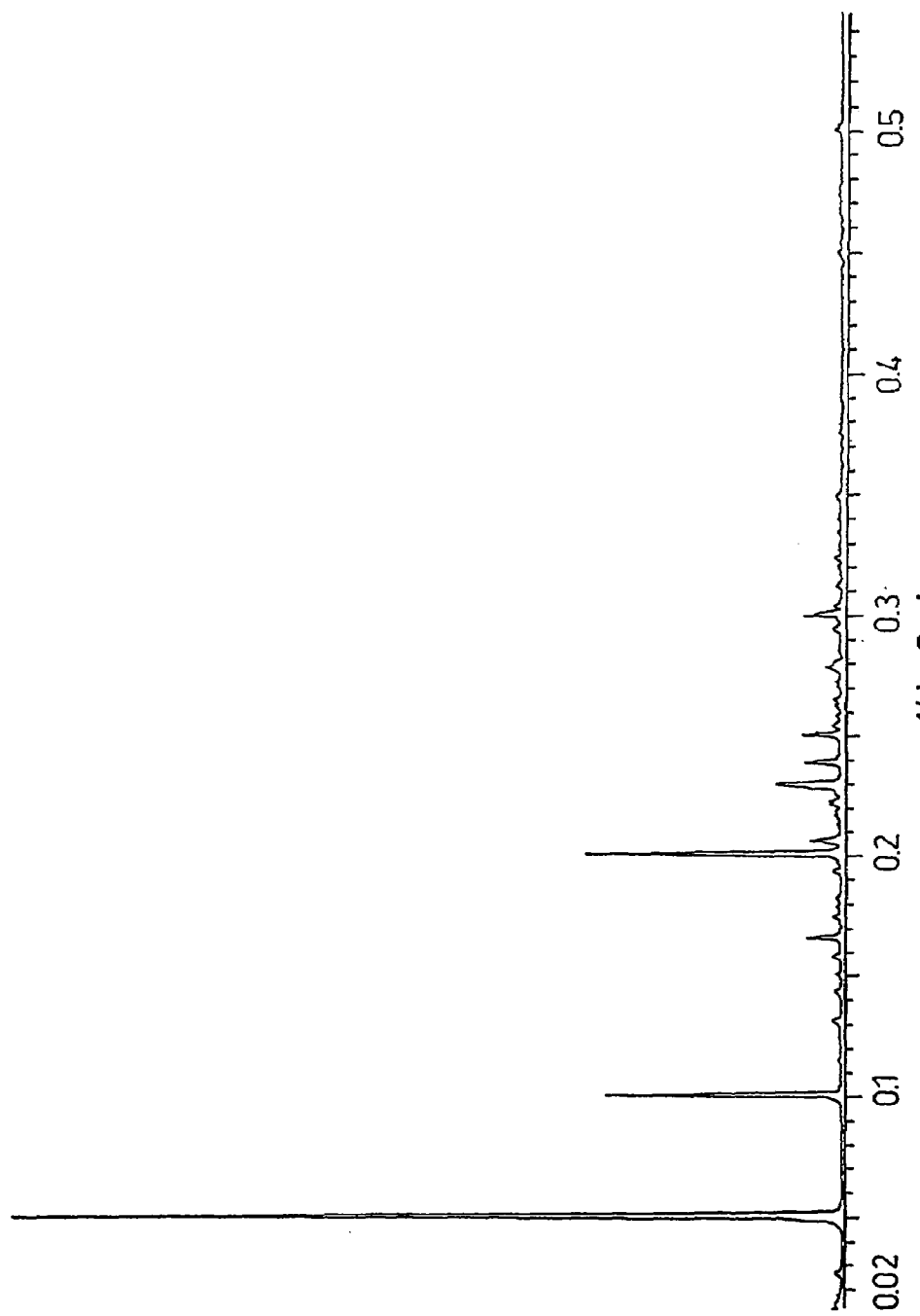

3,7-DIAZABICYCLO [3.3.1] FORMULATIONS AS ANTI-ARRHYTHMIC COMPOUNDS

RELATED APPLICATIONS

This application is a national stage filing under 35 U.S.C. 371 of International Application PCT/SE02/00725, filed Apr. 12, 2002, which claims priority from Sweden Application No. 0101327-5, filed Apr. 12, 2001, the specifications of each of which are incorporated by reference herein. International Application PCT/SE02/00725 was published under PCT Article 21(2) in English.

1. Field of the Invention

This invention relates to new solid state forms of certain antiarrhythmic drugs, to pharmaceutical compositions containing them, and to processes for obtaining them.

BACKGROUND OF THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations comprising the active compound.

Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present significant problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, such as modified-release compositions, it is important, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound will be. This can usually only be determined empirically.

2. Prior Art

International patent application WO 01/28992 discloses a number of oxabispidine compounds, including:

(a) 4-({3-[7-(3,3-dimethyl-2-oxobutyl)-9-oxa-3,7-diazabicyclo[3.3.1]non-3-yl]propyl}amino)benzonitrile:

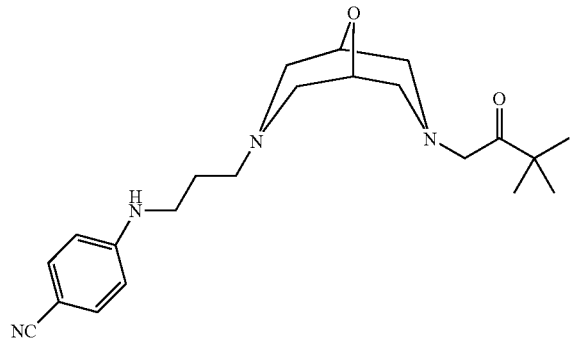

which compound is referred to hereinafter as Compound A. Compound A is specifically disclosed in WO 01/28992, both in the form of the free base and in the form of a benzenesulphonate salt;

(b) tert-butyl 2-{7-[3-(4-cyanoanilino)propyl]-9-oxa-3,7-diazabicyclo-[3.3.1]non-3-yl}ethylcarbamate

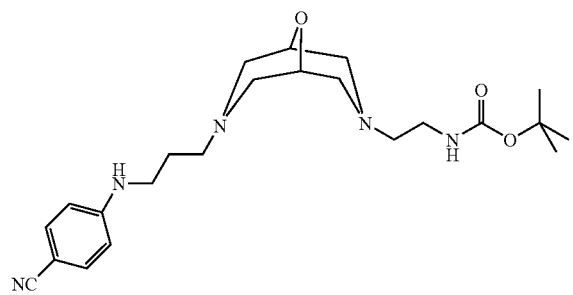

in the form of the free base, which compound is referred to hereinafter as Compound B;

(c) tert-butyl 2-{7-[4-(4-cyanophenyl)butyl]-9-oxa-3,7-diazabicyclo-[3.3.1]non-3-yl}ethylcarbamate

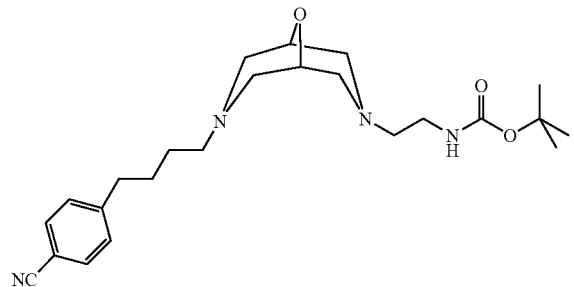

in the form of the free base, which compound is referred to hereinafter as Compound C; and (d) tert-butyl 2-{7-[(2S)-3-(4-cyanophenoxy)-2-hydroxypropyl]-9-oxa-3,7-diazabicyclo[3.3.1]non-3-yl}ethylcarbamate

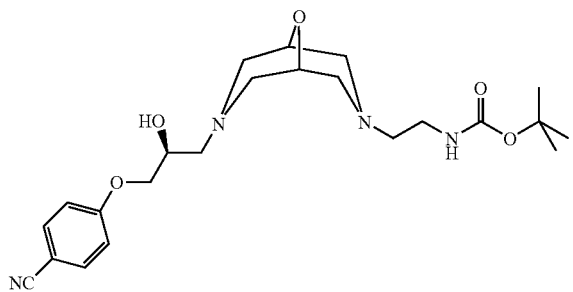

in the form of the free base, which compound is referred to hereinafter as Compound D.

The compounds of international patent application WO 01/28992 are indicated as being useful in the treatment of cardiac arrhythmias.

Processes for the synthesis of Compounds A, B, C and D are described in Examples 3, 7, 8 and 9 (respectively) of WO 01/28992.

Specific pharmaceutically-acceptable salts of Compounds B, C and D are not disclosed in WO 01/28992. Further, no information is provided in relation to different crystalline forms of any of Compounds A, B, C or D, or salts thereof, that may be prepared.

DISCLOSURE OF THE INVENTION

According to a first aspect of the invention there is provided a pharmaceutically-acceptable salt of Compound A, of Compound B, of Compound C, or of Compound D, provided that the salt is not the benzenesulphonic acid salt of Compound A.

According to a second aspect of the invention there is provided Compound A, Compound B, Compound C or Compound D, or a pharmaceutically-acceptable salt of any of those compounds, in substantially crystalline form.

Compounds A, B, C and D, and salts thereof, according to the first and second aspects of the invention are referred to hereinafter as "the compounds of the invention".

Although we have found that it is possible to produce compounds of the invention in forms which are greater than 80% crystalline, by "substantially crystalline" we include greater than 20%, preferably greater than 30%, and more preferably greater than 40% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

It is preferred that, when the compound of the invention is a para-toluenesulphonic acid salt of Compound A, it is provided in a substantially crystalline form.

When the compound of the invention is provided as a crystalline form of Compound A, benzenesulphonic acid salt, it is preferred that the crystalline form is not the form specifically described hereinafter in Example 4 (and/or Claim 8).

When the compound of the invention is provided as a crystalline form of Compound A (free base), it is preferred that the crystalline form is not the form specifically described hereinafter in any one of Example 1 (and/or Claim 4), Example 2 (and/or Claim 5), or Example 3 (and/or Claim 6).

When the compound of the invention is provided as a crystalline form of Compound A, it is preferred that the compound is not provided as the free base, or, when provided in the form of a salt, as the benzenesulphonate salt.

When the compound of the invention is provided as a crystalline form of Compound C (free base), it is preferred that the crystalline form is not the form specifically described hereinafter in Example 12 (and/or Claim 25).

When the compound of the invention is provided as a crystalline form of Compound C, it is preferred that the compound is not provided as the free base.

When the compound of the invention is provided as a crystalline form of Compound D (free base), it is preferred that the crystalline form is not the form specifically described hereinafter in Example 9 (and/or Claim 19).

When the compound of the invention is provided as a crystalline form of Compound D, it is preferred that the compound is not provided as the free base.

When the compound of the invention is provided as a crystalline form of Compound B, it is preferred that the compound is not provided as the free base.

The compounds of the invention may be in the form of a solvate, a hydrate or a mixed solvate/hydrate. Solvates may be of one or more organic solvents, such as lower alkyl (e.g. $C_{1-4}$ alkyl) alcohols (e.g. methanol, ethanol or iso-propanol), ketones (such as acetone), esters (such as ethyl acetate) or mixtures thereof.

Compounds of the invention may have improved stability when compared to compounds/salts disclosed in WO 01/28992.

The term "stability" as defined herein includes chemical stability and solid state stability.

By "chemical stability", we include that it may be possible to store compounds of the invention in an isolated form, or in the form of a formulation in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition.

By "solid state stability", we include that it may be possible to store compounds of the invention in an isolated solid form, or in the form of a solid formulation in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 75%), and/or exposure to 460 lux of UV/visible light, for prolonged periods (i.e. greater than or equal to six months). Under such conditions, compounds of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

Preferred salts of Compounds A, B, C and D include basic or, preferably, acidic addition salts, which salts may be formed by addition of an appropriate amount of the appropriate acid or base prior to isolation (which may include crystallisation). For example, in the case of compounds of the invention in substantially crystalline form, acid or base may be added to the crystallisation mixture before crystallisation is effected.

Preferred addition salts include inorganic and, especially, organic acid acidic addition salts, preferably salts of carboxylic acids, such as hippuric acid, naphthoic acid and hydroxy-substituted naphthoic acid (e.g. 1-hydroxy-2-naphthoic acid), aspartic acid, maleic acid, succinic acid malonic acid, acetic acid, fumaric acid, benzoic acid, terephthalic acid, pamoic acid and hydroxybenzoic acid; those of hydroxy acids, such as salicylic acid, glycolic acid, malic acid, ascorbic acid, citric acid, gluconic acid, lactic acid, as well as tartaric acid and derivatives thereof, such as O,O'-dibenzoyltartaric acid (e.g. O,O'-dibenzoyl-D-tartaric acid or O,O'-dibenzoyl-L-tartaric acid) and O,O'-di-para-toluoyl-tartaric acid (e.g. O,O'-di-para-toluoyl-D-tartaric acid or O,O'-di-para-toluoyl-L-tartaric acid); those of other diacids, such as 2,2,3,3-tetramethyl-1,4-dibutanoic acid and 1,2-cyclopentanedi-carboxylic acid; and those of alkyl-, aryl- and alkylarylsulphonic acids, e.g. $C_{1-8}$ alkyl- and $C_{6-10}$ aryl- and $C_{1-4}$-alkyl-$C_{6-10}$ aryl-sulphonic acids (which aryl- and alkylarylsulphonic acids may be substituted, at the aryl part, with for example, one or more methyl, methoxy, hydroxy or halo groups), including salts of benzenesulphonic acid, toluenesulphonic acid, a hydroxy-substituted benzenesulphonic acid, naphthalenesulphonic acid, naphthalenedisulphonic acid, mesitylenesulphonic acid, methanesulphonic acid, ethanesulphonic acid and 2-hydroxyethane sulphonic acid.

Acid addition salts, particularly of Compound D, that may also be mentioned include those in which the acid is a derivative of hippuric acid, for example an acid of formula I,

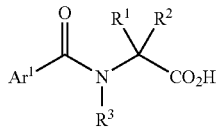

wherein $Ar^1$ represents phenyl or naphthyl, both of which are optionally substituted by one or more substituents selected from halo (e.g. chloro), nitro, $C_{1-6}$ alkyl, $C_{1-6}$ alkoxy, hydroxy and phenyl; and $R^1$, $R^2$ and $R^3$ independently represent H or $C_{1-3}$ alkyl.

It will be appreciated by the skilled person that when $Ar^1$ represents phenyl and $R^1$, $R^2$ and $R^3$ all represent H, then the acid of formula I is hippuric acid.

Preferred $Ar^1$ groups include phenyl, which phenyl group is optionally substituted by phenyl (for example in the 4-position relative to the point of attachment of the C(O) group), chloro (for example in the 3- and/or 4-positions relative to the C(O) group), nitro (for example in the 4-position relative to the C(O) group) and/or $C_{1-4}$ alkyl, such as methyl (for example in the 2- and/or 4-positions relative to the C(O) group); and naphthyl. More preferred values of $Ar^1$ include phenyl, 4-phenylphenyl (biphenyl), 3,4-dichlorophenyl, 2-naphthyl, 4-nitrophenyl and 2,4,6-trimethylphenyl.

Preferred $R^1$ and $R^2$ groups include H and methyl. It is preferred that $R^1$ and $R^2$ either both represent H or both represent methyl.

Preferred $R^3$ groups include H.

When $R^1$ and $R^2$ both represent methyl, it is preferred that $Ar^1$ represents phenyl. When $R^1$ and $R^2$ both represent H, it is preferred that $Ar^1$ represents 4-nitrophenyl, 2,4,6-trimethylphenyl or, especially, 3,4-dichlorophenyl, 2-naphthyl or 4-phenylphenyl (biphenyl).

Acids of formula I are commercially available (e.g. hippuric acid, 4-nitrohippuric acid and 2-, 3- or 4-methylhippuric acid); or may be prepared in accordance with standard techniques.

For example acids of formula I may be prepared by reaction of a compound of formula II,

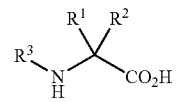

wherein $R^1$, $R^2$ and $R^3$ are as hereinbefore defined, with an acid chloride of formula III,

wherein $Ar^1$ is as hereinbefore defined, for example in the presence of base, e.g. aqueous NaOH, in accordance with classical Schotten-Baumann procedures (see, for example, *J. Med. Chem.*, 1989, 32, 1033). Neutralisation with acid, e.g. conc. hydrochloric acid, may precipitate the acid of formula I, which may be recrystallised if necessary from various solvents, e.g. iso-propyl alcohol, methanol, ethanol, acetone and water, or mixtures of those solvents.

Alternatively, ester (e.g. lower alkyl ester) derivatives of compounds of formula II, optionally in the form of a salt, e.g. the hydrochloride salt, can be reacted with an acid chloride of formula III, in the presence of base, e.g. triethylamine, in a suitable solvent, e.g. dichloromethane, to give an ester-amide of formula IV,

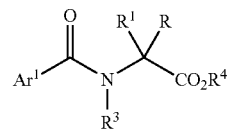

wherein $R^4$ represents lower alkyl (such as $C_{1-6}$ alkyl) or lower alkylphenyl (e.g. $C_{1-3}$ alkylphenyl) and $Ar^1$, $R^1$, $R^2$ and $R^3$ are as hereinbefore defined (see, for example, *J. Heterocyclic Chem.* 1973, 10, 935, *Tetrahedron* 1989, 45, 1691 and *J. Org. Chem.*, 1999, 64, 8929). Ester-amides of formula IV may be solids at room temperature and may thus be purified by crystallisation following their formation, if appropriate. Compounds of formula IV may then be converted to compounds of formula I by standard hydrolysis, e.g. with aqueous sodium hydroxide followed by addition of an acid, e.g. hydrochloric acid, to precipitate the product. Recrystallisation may then be carried out, if required.

Compounds of formulae I, II and IV in which $R^3$ represents $C_{1-3}$ alkyl may be made by standard alkylation of a corresponding compound of formula I, II or IV in which $R^3$ represents H.

Compounds of formulae II (and ester derivatives) and III are commercially available or may be made readily by way of routine techniques.

According to a further aspect of the invention, there is provided a process for the preparation of a compound of the invention which comprises:

(a) addition of an appropriate amount of an acid, or a base, to Compound A, B, C or D to form an acid, or base, addition salt; and/or (b) crystallising Compounds A, B, C or D, or salt of Compound A, B, C or D.

It is possible to crystallise Compounds A, B, C and D, and pharmaceutically-acceptable salts thereof, with or without the presence of a solvent system (e.g. crystallisation may be from a melt, under supercritical conditions, or achieved by sublimation). However, we prefer that the crystallisation is from an appropriate solvent system.

Crystalline acidic or basic addition salts of Compounds A, B, C or D may be provided by adding an appropriate amount of the appropriate acid or base to the crystallisation mixture (e.g. solvent system including Compound A, B, C or D as the free base) before crystallisation is effected. For example, organic acids may be added (optionally in the form of a solution comprising an appropriate polar solvent (e.g. a lower alkyl alcohol, such as methanol or ethanol) or an acetate, such as ethyl acetate) to Compound A, B, C or D (optionally in the form of a solution, wherein the free base is in an appropriate crystallisation solvent). (The skilled person will appreciate that, in this context, the term "free base" means "free form" of Compounds A, B, C or D (i.e. forms that are not in the form of acidic or basic addition salts).)

The skilled person will appreciate that acid or base may be combined in this way with Compound A, B, C or D by way of dissolving the appropriate materials in appropriate solvents as described above, at least partly removing those solvents, and then re-dissolving the resultant mixture prior to performing a crystallisation as described herein.

When the compounds of the invention are in the form of acid addition salts, suitable stoichiometric ratios of acid to free base are in the range 0.25:1.5 to 1.5:1, such as 0.45:1.25 to 1.25:1, including 0.50:1 to 1:1.

The solvent system may be heterogeneous or homogeneous and may thus comprise one or more organic solvents, such as alkyl acetates (e.g. linear or branched $C_{1-6}$ alkyl acetates, such as ethyl acetate, iso-propyl acetate and butyl acetate); lower (e.g. linear or branched $C_{1-6}$) alkyl alcohols, such as hexan-1-ol, 3-methylbutan-1-ol, pentan-1-ol, pentan-2-ol, 4-methyl-2-pentanol and 2-methyl-1-propanol, or a $C_{1-4}$ alkyl alcohol, such as methanol, ethanol, n-propanol, iso-propanol and butanol (e.g. n-butanol); aliphatic (e.g. $C_{6-12}$, such as $C_{7-12}$, aliphatic) hydrocarbons (e.g. iso-hexane, iso-octane and n-heptane) and aromatic hydrocarbons (e.g. toluene); chlorinated alkanes (e.g. chloroform and dichloromethane); dialkyl ketones (e.g. acetone, methyl iso-butyl ketone), acetonitrile, dialkyl ethers (e.g. diethyl ether, di-iso-propyl ether, di-n-propyl ether, di-n-butyl ether and tert-butyl methyl ether); and/or aqueous solvents, such as water. Mixtures of any of the above-mentioned solvents may be used.

Different crystalline forms may have different solubilities in any given solvent at any given temperature. In this respect, above-mentioned solvents may be employed as "antisolvents" (i.e. a solvent in which compounds of the invention are poorly soluble), and may thus aid the crystallisation process. Antisolvents thus include hydrocarbons and dialkyl ethers listed above.

Suitable solvents thus include alkyl acetates (such as ethyl acetate or iso-propyl acetate), lower alkyl alcohols (such as methanol, ethanol and iso-propanol), chlorinated methanes (such as dichloromethane), alkanes (such as n-heptane), ethers (such as diethyl ether), ketones (such as acetone), water etc.

Crystallisation of compounds of the invention from an appropriate solvent system may be achieved by attaining supersaturation in a solvent system which comprises Compound A, B, C or D or salt thereof, (e.g. by cooling, by solvent evaporation and/or via the addition of anti-solvent (i.e. a solvent in which the compounds of the invention are poorly soluble (e.g. a hydrocarbon, such as iso-octane, n-heptane or iso-hexane, or a dialkyl ether, such as di-iso-propyl ether, di-n-butyl ether, etc))), or by decreasing the solubility of the substance by the addition of a salt (such as NaCl), or, in the case of compounds of the invention that are acid addition salts, addition of an excess of the appropriate acid.

Crystallisation temperatures and crystallisation times depend upon the compound or salt that is to be crystallised, the concentration of that compound/salt in solution, and the solvent system which is used.

Crystallisation may also be initiated and/or effected by way of standard techniques, for example with or without seeding with crystals of the appropriate crystalline compound of the invention, and/or by adjustment of pH.

A particular crystallisation process that may be used to prepare Compounds A, B, C and, especially, D and salts thereof, involves dissolving compound of the invention in a solvent system comprising a $C_{3-7}$ alkyl alcohol and an appropriate di-$C_{3-5}$-alkyl ether antisolvent.

According to a further aspect of the invention there is thus provided a process for the preparation of a substantially crystalline form of Compound A, Compound B, Compound C or, especially, Compound D, or a pharmaceutically-acceptable salt of any of those compounds, which process comprises crystallising the relevant compound from a solvent system comprising a combination of a $C_{3-7}$ alkyl alcohol and a di-$C_{3-5}$-alkyl ether.

Preferred ethers include di-$C_{3-5}$-alkyl ethers, such as di-n-propyl ether, di-iso-propyl ether and di-n-butyl ether. Preferred alcohols include n-propanol, iso-propanol, n-butanol, 4-methyl-2-pentanol, 3-methyl-1-butanol, 2-methyl-1-propanol and pentan-1-ol.

Preferred solvent combinations include:
n-propanol and di-n-propyl ether;
iso-propanol and di-iso-propyl ether;
n-butanol and di-n-butyl ether;
4-methyl-2-pentanol and di-n-butyl ether;
iso-propanol and di-n-butyl ether;
4-methyl-2-pentanol and di-iso-propyl ether; and
pentan-1-ol and di-iso-propyl ether.

Compound/salt may be added to the alcohol/ether solvent system with the latter in pre-mixed form. Alternatively, compound/salt may be dissolved in the appropriate alcohol and then ether may be added to the resultant solution. Salts may also be made in situ as hereinbefore described.

Preferably compound/salt is dissolved in the solvent combination by heating to an elevated temperature (e.g. 50 to 100° C., such as 65 to 90° C., e.g. 75 to 85° C.) to ensure complete dissolution. Then the resultant solution is allowed to cool to effect crystallisation.

This alcohol/ether crystallisation process is preferably employed to provide crystalline forms of Compound D and salts thereof. Preferably it may be used to provide crystalline Compound D in the form of the free base.

We have found that, when compounds of the invention (and particularly Compound D) are prepared by crystallisation from this particular solvent system, highly crystalline material is obtained in an efficient manner, with a high recovery of crystalline material (in a good yield), and in a predictable amount of time.

Compounds of the invention may also be prepared in the form of a solvate (by which we include in the form of a hydrate, such as a monohydrate) or otherwise (e.g. in the form of an anhydrate).

To ensure that anhydrate is produced, the solvent from which the crystallisation occurs should preferably be dried, either before or during the crystallisation process, in order to reduce the water content below a critical level, which should preferably not be exceeded during the crystallisation. Solvent may be dried during the crystallisation process, for example by decreasing the water content of a mixture of the compound/salt to be crystallised and the appropriate organic solvent/aqueous solvent system (e.g. by increasing the amount of organic solvent that is present and/or removal of water by formation of an azeotrope, with successive distillations).

To ensure that hydrates (e.g. monohydrates) are produced, water must be present in the solvent from which the crystallisation occurs. The water content should preferably be kept above the critical level mentioned above during the crystallisation.

The "critical level" of water depends upon factors such as temperature, concentration in solution of the compound to be crystallised, impurity profile, and the solvent system which is employed, but may be determined non-inventively.

Thus, crystalline hydrates may be prepared by crystallising compounds of the invention from a solvent system comprising water, or a combination of water and one or more organic solvents, including organic solvents that are capable of dissolving water (e.g. methanol, ethanol, isopropanol, etc).

Conversely, crystalline anhydrates may be prepared by crystallising compounds of the invention from an appropriate organic solvent system which may have been dried, and/or may be dried during the crystallisation process, such that the water content is below the above-mentioned critical level. Thus, anhydrate may be produced by crystallisation from a solvent system which is substantially free of water.

By "substantially free of water", we include that the water content in the solvent system is below that which will result in the formation of, at most, 10% of hydrate (e.g. monohydrate), for any particular solvent system and set of crystallisation conditions.

Compounds of the invention that are anhydrates contain no more than 3%, preferably 2%, more preferably 1% and more preferably 0.5% (w/w) water, whether such water is bound (crystal water or otherwise) or not. Hydrates contain no less than 0.5 mol of water per mol of compound of the invention.

Whether anhydrates or hydrates crystallise is related to kinetics and to the equilibrium conditions of the respective forms at the specific conditions.

When the compound of the invention is provided as a crystalline form of Compound A, benzenesulphonic acid salt, it is preferred that that salt is provided as a monohydrate.

Further, as will be appreciated by the skilled person, compounds of the invention that are in the same chemical form (free base/salt) may also be obtained in different physical forms (e.g. different crystalline forms) under different crystallisation conditions. The crystalline form of the compound of the invention that is obtained depends upon both the kinetics and the thermodynamics of the crystallisation process. Under certain thermodynamic conditions (solvent system, temperature, pressure and concentration of compound of the invention), one crystalline form may be more stable than another (or indeed any other). However, crystalline forms that have a relatively low thermodynamic stability may be kinetically favoured. Thus, in addition, kinetic factors, such as time, impurity profile, agitation, the presence or absence of seeds, etc. may also influence which forms appear. Thus, the procedures disclosed herein may be adapted by the skilled person as appropriate in order to obtain different crystalline forms.

Different crystalline forms of the compounds of the invention may be readily characterised using X-ray powder diffraction (XRPD) methods, for example as described hereinafter.

In order to ensure that a particular crystalline form is prepared in the absence of other crystalline forms, crystallisations are preferably carried out by seeding with nuclei and/or seed crystals of the desired crystalline form in substantially complete absence of nuclei and/or seed crystals of other crystalline forms. Seed crystals of appropriate compound/salt may be prepared, for example, by way of slow evaporation of solvent from a portion of solution of appropriate compound/salt.

Compounds of the invention may be isolated using techniques which are well known to those skilled in the art, for example decanting, filtering or centrifuging.

Compounds may be dried using standard techniques. It will be appreciated by the skilled person that drying temperature and drying time may affect the solid state properties of compounds (or salts) that are in the form of solvates, such as hydrates (e.g. dehydration may occur at elevated temperatures and/or reduced pressure). For example, following the formation of crystalline hydrate, there may be a critical humidity below which the drying should not be performed, as the crystal water may be lost and a solid state transformation may occur, i.e. the crystal water may be lost if the crystals are dried at high temperatures or at very low pressures for a longer period.

We have found that, by employing crystallisation processes as described herein, it is possible to produce compounds of the invention with a higher chemical purity than that of the compound of the invention which is to be isolated in the first instance.

Further purification of compounds of the invention may be effected using techniques, which are well known to those skilled in the art. For example impurities may be removed by way of recrystallisation from an appropriate solvent system (e.g. ethyl acetate, iso-propyl acetate, dichloromethane, isopropanol, n-heptane, methanol, ethanol, methylethyl ketone, acetonitrile, pentan-2-ol, 3-methylbutan-1-o, hexan-1-ol, water or a combination of these solvents). Suitable temperatures and times for the recrystallisation depend upon the concentration of the compound, or salt, in solution, and upon the solvent system which is used.

When compounds of the invention are crystallised, or recrystallised, as described herein, the resultant compound, or salt, may be in a form which has improved chemical and/or solid state stability, as mentioned hereinbefore.

Pharmaceutical Preparations and Medical Uses

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as may be demonstrated in tests, such as those described in inter alia international patent applications WO 99/31100, WO 00/77000 and WO 01/28992, the relevant disclosures in which documents are hereby incorporated by reference.

The compounds of the invention are thus expected to be useful in both the prophylaxis and the treatment of arrhythmias, and in particular atrial and ventricular arrhythmias. Particular disease states that may be mentioned include atrial fibrillation (e.g. atrial flutter).

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found selectively to delay cardiac repolarization. Although compounds of the invention have been found to delay cardiac repolarisation in particular, in the treatment of arrhythmias, their mode(s) of activity is/are not necessarily restricted to this mode of action.

According to a further aspect of the invention, there is provided a method of treatment of an arrhythmia which method comprises administration of a therapeutically effective amount of a compound of the invention to a person suffering from, or susceptible to, such a condition.

For the avoidance of doubt, by "treatment" we include the therapeutic treatment, as well as the prophylaxis, of a condition.

The compounds of the invention will normally be administered orally, subcutaneously, intravenously, intraarterially, transdermally, intranasally, by inhalation, or by any other parenteral route, in the form of pharmaceutical preparations comprising the active ingredient (either as the free base or as a salt), in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

The compounds of the invention may be further processed before formulation into a suitable pharmaceutical formulation. For example, the crystalline form may be milled or ground into smaller particles.

Preferred pharmaceutical formulations include those in the form of a gelling matrix system, in which compounds of the invention are provided in association with a polymer that swells in an aqueous medium, such as those found in the gastrointestinal tract. Such systems are well known in the art (see, for example, *Advanced Drug Delivery Reviews,* 11, 37 (1993)).

The amount of compound of the invention which is employed in such a formulation will depend on the condition, and patient, to be treated, as well as the compound(s) which is/are employed, but can be determined non-inventively.

Suitable daily doses of the compounds of the invention in the (e.g. therapeutic) treatment of humans are about 0.005 to 25.0 mg/kg body weight at oral administration, and about 0.005 to 10.0 mg/kg body weight at parenteral administration, of free base (i.e., in the case of a salt, excluding any weight resulting from the presence of a counter ion). Preferable ranges of daily doses of the compounds of the invention (in the form of free base as indicated above) in the (e.g. therapeutic) treatment of humans are about 0.005 to 10.0 mg/kg body weight at oral administration and about 0.005 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

The compounds of the invention have the advantage that they are in a form which provides for improved ease of handling. Further, the compounds of the invention have the advantage that they may be produced in forms which have improved chemical and solid state stability (including e.g. lower hygroscopicity). Thus, the compounds may be stable when stored over prolonged periods.

Compounds of the invention may also have the advantage that they may be cystallised in good yields, in a higher purity, in less time, more conveniently, and at a lower cost, than forms of Compounds A, B, C and D and salts thereof prepared previously.

The invention is illustrated, but in no way limited, by the following examples, with reference to the enclosed figures in which:

FIG. 5(*b*) shows an X-ray powder diffractogram for the crystalline form of Compound A, para-toluenesulphonic acid salt (B Form), obtained by way of Example 5.

GENERAL PROCEDURES

Figure 1:
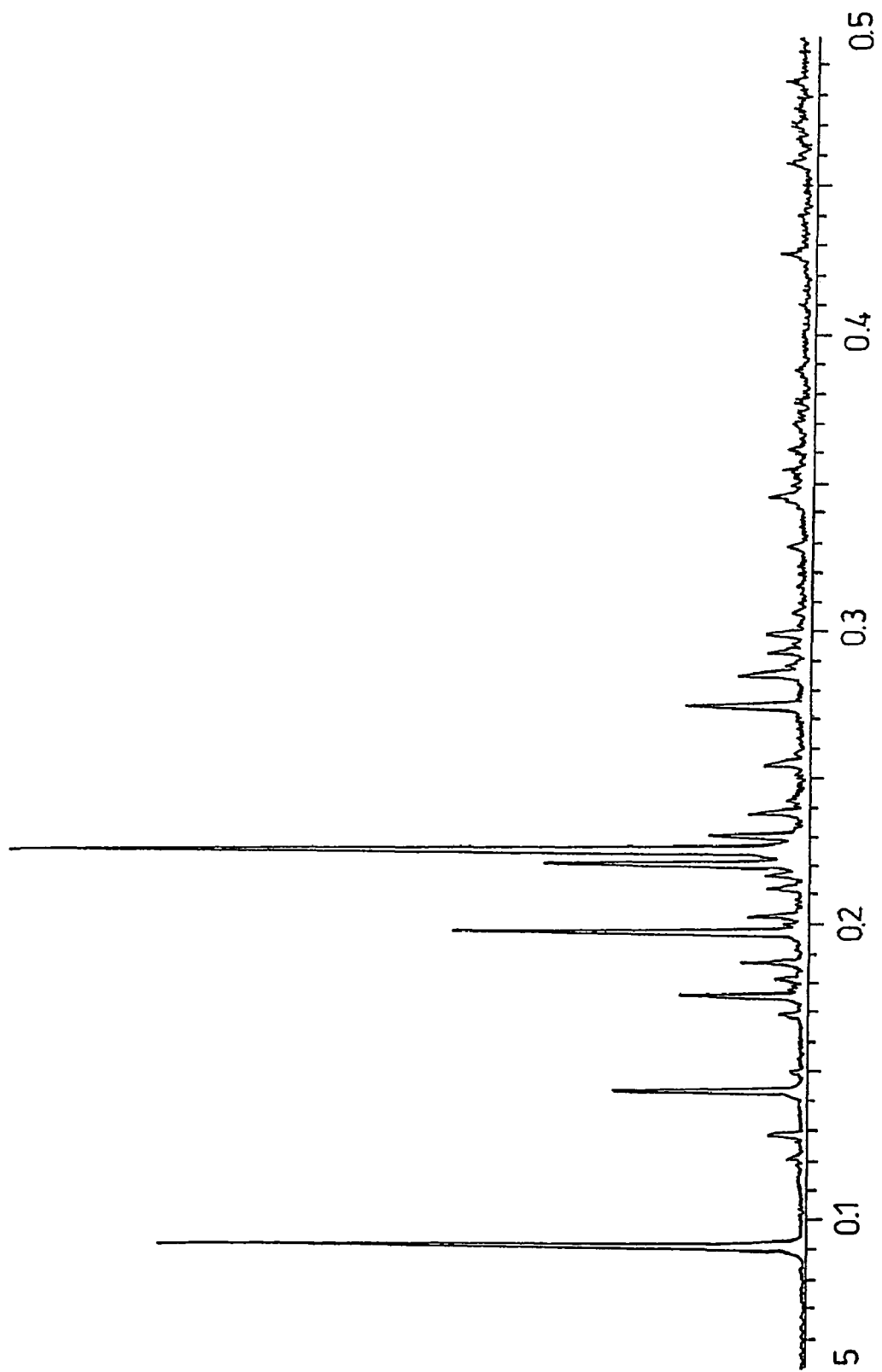
FIG. 1 shows an X-ray powder diffractogram for the crystalline form of Compound A (B Form), obtained by way of Example 1.

X-ray powder diffraction analysis (XRPD) was performed using variable slits on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a Siemens D5000 diffractometer.

Differential scanning calorimetry (DSC) was performed using a Mettler DSC820 instrument, according to standard methods, for example those described in Höhne, G. W. H. et al (1996), *Differential Scanning Calorimetry*, Springer, Berlin.

Thermogravimetric analysis (TGA) was performed using a Mettler Toledo TGA850 instrument.

It will be appreciated by the skilled person that crystalline forms of compounds of the invention may be prepared by analogy with processes described herein and/or in accordance with the Examples below, and may show essentially the same XRPD diffraction patterns and/or DSC and/or TGA thermograms as those disclosed herein. By "essentially the same" XRPD diffraction patterns and/or DSC and/or TGA thermograms, we include those instances when it is clear from the relevant patterns and/or thermograms (allowing for experimental error) that essentially the same crystalline form has been formed. When provided, DSC onset temperatures may vary in the range ±5° C. (e.g. ±2° C.), and XRPD distance values may vary in the range ±2 on the last decimal place. It will be appreciated by the skilled person that XRPD intensities may vary when measured for essentially the same crystalline form for a variety of reasons including, for example, preferred orientation.

PREPARATION A

Preparation of Compound A and Benzenesulphonate Salt Thereof (i) 4-[(3-Hydroxypropyl)amino]benzonitrile Alternative 1 A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added The mixture was allowed to cool to room temperature, and was then extracted with diethyl ether. The organic layer was separated, dried ($Na_2SO_4$), filtered and concentrated in vacuo to yield 17 g (97%) of the sub-title compound as an oil that crystallised upon standing.

Alternative 2 4-Fluorobenzonitrile (24.6 g, 0.203 mol, Aldrich 99%) was added to 3-amino-1-propanol (122.0 g, 1.625 mol, 8 equiv., Aldrich 99%) and the mixture heated to 80° C. for 5 hours, under nitrogen. The solution was allowed to cool to 22° C. and water (300 mL) was added. The cloudy solution was extracted twice with methylene chloride (300 mL and 200 mL) and the combined methylene chloride extracts were washed with water (300 mL; GC analysis of organic layer gave ~1.0 area % aminopropanol remaining).

Alternative 3 To 4-fluorobenzonitrile (30.29 g, 247.7 mmol, 1.0 eq), was added 3-amino-1-propanol (150 mL, 148.8 g, 1981.5 mmol, 8.0 eq). The mixture was stirred under nitrogen at room temperature (27° C.) until all of the solid had dissolved. The solution was heated (oil bath) to 77° C. and kept at this temperature for 7 hours, before being stirred at ambient temperature overnight (14 hours). Water (365 mL) was added, and the resultant cloudy solution was extracted with dichloromethane (365 mL, then 245 mL). The combined organic layers were washed with water (365 mL). The DCM solution of the product was dried by distillation: solvent (200 mL) was removed and replaced with fresh DCM (200 mL). More solvent (250 mL) was removed to bring the total solvent volume to 365 mL.

(ii) 3-(4-Cyanoanilino)propyl 4-methylbenzenesulfonate

Alternative I A cooled (0° C.) solution of 4-[(3-hydroxypropyl)-amino]benzonitrile (from step (i) (Alternative 1)

above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the title compound.

Alternative II The solution of the crude 4-[(3-hydroxypropyl)amino]-benzonitrile (from step (i) (Alternative 2) above) was concentrated to a volume of 300 mL by distillation and a further 200 mL methylene chloride added and re-distilled to 300 mL (solution water by Karl-Fischer 0.07%). Triethylamine (20.55 g, 0.203 mol), followed by 4-(N,N-dimethylamino)pyridine (248 mg, 2.0 mmol) was added and the solution was cooled to 0° C. A solution of tosyl chloride (38.70 g, 0.203 mol) in methylene chloride (150 mL) added over ca. 30 minutes with cooling and good agitation, allowing the temperature to rise to 5° C. The reaction was stirred for 23 hours in the range 3 to 5° C. under nitrogen. (After 5 hours, triethylamine hydrochloride precipitation occurred. TLC showed very little if any further conversion of residual cyano alcohol at 20–23 hours.) Water (300 mL) was added and the layers vigorously agitated for 15 min. The organic solution was concentrated by distillation at 35 to 40° C. to a volume of ca. 60 to 70 mL. iso-Propanol (100 mL) was added over 5 minutes. (At this stage, some granular precipitation of product occurred prior to addition of iso-propanol. Crystallization occurred rapidly upon addition of iso-propanol.) Distillation was continued using vacuum to remove the last of the methylene chloride. (A further ~30 mL was removed and the distillate was checked by GC for the absence of methylene chloride.) The crystal slurry was cooled to 0 to 5° C. over ca. 1 hour with slow agitation and held for one hour at 0–5° C. The crystals were filtered on a medium sinter and the compacted damp filter cake carefully washed with cold (0° C.) iso-propanol (80 mL). The filter cake was dried under vacuum and a stream of nitrogen overnight. Yield: 52.6 g, 78.4 mole %; HPLC: 99.64 area %.

Microanalysis: found (theory): % C: 61.60 (61.67); % H: 5.41 (5.49); % N: 8.44 (8.47); % S: 9.71(9.70).

(iii) N,N-Bis (2-oxiranylmethyl)benzenesulphonamide

Water (2.5 L, 10 vol.) followed by epichlorohydrin (500 mL, 4 eq.) were added to benzenesulphonamide (250 g, 1 eq.). The reactants were heated to 40° C. Aqueous sodium hydroxide (130 g in 275 mL of water) was added such that the temperature of the reaction remained between 40° C. and 43° C. This took approximately 2 hours. (The rate of sodium hydroxide addition needs to be slower at the start of the addition than at the end in order to keep within the temperature range stated.) After the addition of sodium hydroxide was complete, the reaction was stirred at 40° C. for 2 hours, then at ambient temperature overnight. The excess epichlorohydrin was removed as a water azeotrope by vacuum distillation (ca. 40 mbar, internal temp 30° C.), until no more epichlorohydrin distilled. Dichloromethane (1 L) was added and the mixture stirred rapidly for 15 minutes. The phases were allowed to separate (this took 10 minutes although totally clear phases are obtained after standing overnight). The phases were separated and the dichloromethane solution used in the subsequent step below.

$^1$H NMR (400 MHz, $CDCl_3$): δ 2.55–2.65 (2H, m), 2.79 (2H, t, J 4.4), 3.10–3.22 (4H, m), 3.58–3.73 (2H, m), 7.50–7.56 (2H, m), 7.58–7.63 (1H, m), 7.83–7.87 (2H, m).

(iv) 5-Benzyl-3,7-dihydroxy-1-phenylsulphonyl-1,5-diazacyclooctane

IMS (2.5 L, 10 vol) was added to the dichloromethane solution from step (iii) above. The solution was distilled until the internal temperature reached 70° C. Approximately 1250 mL of solvent was collected. More IMS (2.5 L, 10 vol) was added followed by benzylamine (120 mL, 0.7 eq.) in one portion (no exotherm seen), and the reaction was heated at reflux for 6 hours (no change from 2 hour sampling point). More benzylamine was added (15 mL) and the solution was heated for a further 2 hours. The IMS was distilled off (ca. 3.25 L) and toluene was added (2.5 L). More solvent was distilled (ca. 2.4 L) and then further toluene added (1 L). The head temperature was now 110° C. A further 250 mL of solvent was collected at 110° C. Theoretically, this left the product in ca. 2.4 L of toluene at 110° C. This solution was used in the next step.

$^1$H NMR (400 MHz, $CDCl_3$): δ 7.83–7.80 (4H, m, ArH), 7.63–7.51 (6H, m, ArH), 7.30–7.21 (10H, ArH), 3.89–3.80 (4H, m, CH(a)+CH(b)), 3.73 (2H, s, $CH_2Ph(a)$), 3.70 (2H, s, $CH_2Ph(b)$), 3.59 (2H, dd, $CHHNSO_2Ar(a)$), 3.54 (2H, dd, $CHHNSO_2Ar(b)$), 3.40 (2H, dd, $CHHNSO_2Ar(b)$), 3.23 (2H, dd, $CHHNSO_2Ar(a)$), 3.09–2.97 (4H, m, CHHNBn(a)+ CHHNBn(b)), 2.83 (2H, dd, CHHNBn(b)), 2.71 (2H, dd, CHHNBn(a))

(Data taken from purified material comprising a 1:1 mixture of trans-(a), and cis-diol (b))

(v) 3-Benzyl-7-(phenylsulphonyl)-9-oxa-3,7-diazabicyclo[3.3.1]nonane

The toluene solution from the previous step (iv) above was cooled to 50° C. Anhydrous methanesulphonic acid (0.2 L) was added. This caused a temperature rise from 50° C. to 64° C. After 10 minutes, methanesulphonic acid was added (1 L) and the reaction heated to 110° C. for 5 hours. Toluene was then distilled from the reaction; 1.23 L was collected. (Note that the internal temperature should not be allowed higher than 110° C. at any stage otherwise the yield will be decreased.) The reaction was then cooled to 50° C. and a vacuum applied to remove the rest of the toluene. Heating to 110° C. and 650 mbar allowed a further 0.53 L to be removed. (If the toluene can be removed at a lower temperature and pressure then that is beneficial.) The reaction was then left to cool to 30° C. and deionised water (250 mL) was added. This caused the temperature to rise from 30° C. to 45° C. More water (2.15 L) was added over a total time of 30 minutes such that the temperature was less than 54° C. The solution was cooled to 30° C. and then dichloromethane (2 L) was added. With external cooling and rapid stirring, the reaction mixture was basified by adding aqueous sodium hydroxide (10 M, 2 L) at a rate that kept the internal temperature below 38° C. This took 80 minutes. The stirring was stopped and the phases separated in 3 minutes. The layers were partitioned. IMS (2 L) was added to the dichloromethane solution and distillation started. Solvent (2.44 L) was collected until the head temperature reached 70° C. Theoretically, this left the product in 1.56 L of IMS. The solution was then allowed to cool to ambient temperature overnight with slow stirring. The solid product that precipitated was filtered and washed with IMS (0.5 L) to give a fawn-coloured product that, on drying at 50° C., in vacuum, gave 50.8 g (8.9% over 3 steps). 20.0 g of this product was dissolved in acetonitrile (100 mL) at reflux to give a pale yellow solution. After cooling to ambient temperature, the crystals that formed were collected by filtration and washed with acetonitrile (100 mL). The product was dried in vacuo at 40° C. for 1 hour to give 17.5 g (87%) of sub-title compound.

$^1$H NMR (400 MHz, CDCl$_3$): δ 7.18–7.23 (10H, m), 3.86–3.84 (2H, m), 3.67 (2H, d), 3.46 (2H, s), 2.91 (2H, d), 2.85 (2H, dd), 2.56 (2H, dd)

(vi) 3-Benzyl-9-oxa-3,7-diazabicyclo[3.3.1] nonane×2 HCl

Concentrated hydrobromic acid (1.2 L, 3 rel. vol.) was added to solid 3-benzyl-7-(phenylsulphonyl)-9-oxa-3,7-diazabicyclo[3.3.1]nonane (400 g, see step (v) above) and the mixture was heated to reflux under a nitrogen atmosphere. The solid dissolved in the acid at 95° C. After heating the reaction for 8 hours, HPLC analysis showed that the reaction was complete. The contents were cooled to room temperature. Toluene (1.2 L, 3 rel. vol.) was added and the mixture stirred vigorously for 15 minutes. Stirring was stopped and the phases were partitioned. The toluene phase was discarded along with a small amount of interfacial material. The acidic phase was returned to the original reaction vessel and sodium hydroxide (10 M, 1.4 L, 3.5 rel. vol.) was added in one portion. The internal temperature rose from 30° C. to 80° C. The pH was checked to ensure it was >14. Toluene (1.6 L, 4 rel. vol.) was added and the temperature fell from 80° C. to 60° C. After vigorous stirring for 30 minutes, the phases were partitioned. The aqueous layer was discarded along with a small amount of interfacial material. The toluene phase was returned to the original reaction vessel, and 2-propanol (4 L, 10 rel. vol.) was added. The temperature was adjusted to between 40° C. and 45° C. Concentrated hydrochloric acid (200 mL) was added over 45 minutes such that the temperature remained at between 40° C. and 45° C. A white precipitate formed. The mixture was stirred for 30 minutes and then cooled to 7° C. The product was collected by filtration, washed with 2-propanol (0.8 L, 2 rel vol.), dried by suction and then further dried in a vacuum oven at 40° C.

Yield=297 g (91%). $^1$H NMR (CD$_3$OD+4 drops D$_2$O): δ 2.70 (br d, 2H), 3.09 (d, 2H), 3.47 (br s, 4H), 3.60 (s, 2H), 4.12 (br s, 2H), 7.30–7.45 (m, 5H). API MS: m/z=219 [C$_{13}$H$_{18}$N$_2$O+H]$^+$.

(vii) 3,3-Dimethyl-1-[9-oxa-7-(phenylmethyl)-3,7-diazabicyclo[3.3.1]non-3-yl]-2-butanone Water (500 mL, 5 vol.) followed by 1-chloropinacolone (45.8 mL, 1 eq.) were added to sodium bicarbonate (114.2 g, 4 eq.). A solution of 3-benzyl-9-oxa-3,7-diazabicyclo [3.3.1]nonane×2 HCl (100.0 g; see step (vi) above) in water (300 mL, 3 vol.) was added slowly, so that the evolution of carbon dioxide was controlled (20 mins.). The reaction mixture was heated at 65 to 70° C. for 4 hours. After cooling to ambient temperature, dichloromethane (400 mL, 4 vol.) was added and, after stirring for 15 minutes, the phases were separated. The aqueous phase was washed with dichloromethane (400 mL, 4 vol.) and the organic extracts combined. The solution was distilled and solvent collected (550 mL). Ethanol (1 L) was added and the distillation continued. Further solvent was collected (600 mL). Ethanol (1 L) was added and the distillation continued. Further solvent was collected (500 mL) (the head temperature was now 77° C.). This solution (theoretically containing 1150 mL of ethanol) was used directly in the next step.

$^1$H NMR (400 MHz, CDCl$_3$): δ 1.21 (9H, s), 2.01–2.59 (2H, m), 2.61–2.65 (2H, m), 2.87–2.98 (4H, m), 3.30 (2H, s), 3.52 (2H, s), 3.87 (2H, br s), 7.26 (2H, d, J7.6), 7.33 (1H, dd, J7.6, 7.6), 7.47 (2H, d, J7.6).

(viii) 3,3-Dimethyl-1-(9-oxa-3,7-diazabicyclo[3.3.1] non-3-yl)-2-butanone

Palladium on charcoal (44 g, 0.4 wt. eq. of 61% wet catalyst, Johnson Matthey Type 440 L) was added to the ethanol solution from the previous step (vii) above. The mixture was hydrogenated at 4 bar. The reaction was considered complete after 5 hours. The catalyst was removed by filtration and washed with ethanol (200 mL). The combined ethanol filtrates were/may be used in step (ix) below. Solution assay gave 61.8 g of title product in ethanol (theoretically 1.35 L; measured 1.65 L). A portion of the product was isolated and purified. Analysis was performed on the purified product.

$^1$H NMR (300 MHz, CDCl$_3$): δ 1.17 (9H, s), 2.69 (2H, dt, J 11.4, 2.4), 2.93 (2H, d, J 10.8), 3.02 (2H, d, J 13.8), 3.26 (2H, s), 3.32 (2H, dt, J 14.1), 3.61 (2H, br s).

This reaction may also be performed using a lower weight ratio of catalyst to benzylated starting material. This may be achieved in several different ways, for example by using different catalysts (such as Pd/C with a metal loading different from that in the Type 440 L catalyst employed above, or Rh/C) and/or by improving the mass transfer properties of the reaction mixture (the skilled person will appreciate that improved mass transfer may be obtained, for example, by performing the hydrogenation on a scale larger than that described in the above reaction). Using such techniques, the weight ratio of catalyst to starting material may be reduced below 4:10 (e.g. between 4:10 and 1:20.).

(ix) Compound A, benzenesulphonic acid salt monohydrate

Method 1

Potassium carbonate (56.6 g, 1.5 equiv) and 3-(4-cyanoanilino)propyl-4-methylbenzenesulphonate (see step (ii) above, 90.3 g, 1 equiv) were added to an ethanol solution of 3,3-dimethyl-1-(9-oxa-3,7-diazabicyclo[3.3.1]non-3-yl)-2-butanone (see step (viii) above; 61.8 g from assay in 1.65 L). The reaction was heated at 80° C. for 4 hours. An assay showed some reactant remained (8.3 g), so more 3-(4-cyanoanilino)propyl-4-methylbenzenesulphonate (12.2 g) was added, and the resultant was heated at 80° C. for 4 hours. Solvent (1.35 L) was distilled, then iso-propyl acetate (2.5 L) added. Solvent (2.51 L) was removed. iso-Propyl acetate (2.5 L) was added. Solvent (0.725 L) was removed. The internal temperature was now at 88° C. Solvent (0.825 L) was removed, leaving the product as an iso-propyl acetate solution (theoretically in 2.04 L). After cooling to 34° C., water (0.5 L) was added. There was a black suspension, possibly of Pd, in the mixture. The pH of the aqueous phase was 11. Sodium hydroxide (1 M, 0.31 L) was added, so that the temperature was less than 25° C., and the mixture was stirred vigorously for 5 minutes. The pH of the aqueous phase was 12. The phases were separated and the aqueous phase discarded. More water (0.5 L) was added, and the phases were separated. The aqueous phase was discarded. The remaining ester solution was filtered to remove suspended particles, and the filtrate was then made up to exactly 2 L. The solution was then split into 2×1 L portions.

(In order to avoid producing sub-title product comprising a high palladium content, the following treatment may be performed: Deloxan® resin (12.5 g, 25 wt %) was added to the solution of the free base (1 L), and the mixture heated at reflux with vigorous stirring for 5 hours. The solution was then cooled to room temperature, and was stirred for 2 days. The resin was removed by filtration.)

An assay was performed to calculate the required amount of benzenesulphonic acid, to make the benzenesulphonate salt.

A solution of benzenesulphonic acid (20.04 g, 1 eq., assuming acid was pure monohydrate) in isopropyl acetate (200 mL) was added over 5 minutes (better to add slower if possible) with vigorous stirring to the solution of the free base (1 L) and a pale yellow precipitate formed. The temperature rose from 18° C. to 22° C. After 10 minutes, the mixture was cooled to 10° C. and the product collected by filtration. The product was washed with iso-propyl acetate (250 mL), sucked dry on the filter then dried under vacuum at 40° C. for 2 days to give 59.0 g (61% from 3-benzyl-9-oxa-3,7-diazabicyclo[3.3.1]nonane×2 HCl).

(The crude benzenesulphonate salt was alternatively prepared by the addition of a 70% (w/w) aqueous solution of benzenesulphonic acid to an ethanolic solution of the free base.)

The crude sub-title product is isolated as a monohydrate.

Ethanol (500 mL) and water (250 mL) were added to crude sub-title compound (50.0 g). The solution was heated to 75° C. Material was all dissolved at 55° C. The solution was held at 75° C. for 5 minutes, then cooled to 5° C. over 1 hour. Precipitation started at 18° C. The cold solution was filtered and the filtrate washed with ethanol:water (2:1; 150 mL), sucked dry on the filter, and then dried in vacuo at 40° C. to give pure sub-title product (41.2 g, 82%).

(This recrystallisation may be carried out with greater volumes of solvent if necessary to fit the reaction vessels e.g.

EtOH:water 2:1, 45 vol. (gave 62% recovery)

EtOH:water 6:1, 35 vol. (gave 70% recovery).)

The sub-title product was isolated as the monohydrate following the rescrystallisation (as determined by single crystal X-ray diffraction).

Method 2

(a) 3-(4-Cyanoanilino)propyl benzenesulfonate

To the solution of 4-[(3-hydroxypropyl)amino]benzonitrile (from step (i) Alternative 3 above, assumed 43.65 g, 247.7 mmol, 1.0 eq) in dichloromethane (360 mL total solution volume) was added, sequentially, triethylamine (52 mL, 37.60 g, 371.55 mmol, 1.5 eq) and trimethylamine hydrochloride (11.89 g, 123.85 mmol, 0.5 eq) in one portion. The yellow solution was cooled to −20° C. (using an acetone/dry ice bath or a cold plate), and treated with a solution of benzenesulfonyl chloride (32 mL, 43.74 g, 247.7 mmol, 1.0 eq) in dichloromethane (220 mL, 5 vols with respect to the cyanoalcohol) via a pressure equalising dropping funnel. The solution was added portionwise such that the internal temperature did not exceed −14° C. The addition took 25 minutes to complete. The mixture was then stirred for 35 minutes at between −15 and −10° C. Water (365 mL) was added and the temperature rose to 10° C. The mixture was cooled back to 0+ C. and stirred vigorously for 15 minutes. The organic layer (volume 570 mL) was collected and distilled at atmospheric pressure to remove DCM (450 mL, pot temperature 40–42° C., still-head temperature 38–39° C.). Ethanol (250 mL) was added, and the solution was allowed to cool to below 30° C. before turning on the vacuum. More solvent was removed (40 mL was collected, pressure 5.2 kPa (52 mbar), pot and still-head temperatures were 21–23° C.), and the product gradually came out of solution. The distillation was stopped at this point, and more ethanol (50 mL) was added. The mixture was warmed (hot water bath at 50° C.) to 40° C. to dissolve all the solid, and water (90 mL) was added slowly via a dropping funnel. The solution was stirred slowly at room temperature (20° C.) overnight (15 hours), by which time some product had crystallised out. The mixture was cooled to −5° C. (ice/methanol bath) and stirred at this temperature for 20 minutes before collecting the pale yellow solid by filtration. The solid was washed with an ethanol/water mixture (42 mL EtOH, 8 mL $H_2O$), and suction dried for 30 minutes before drying to constant weight in the vacuum oven (40° C., 72 hours). The mass of crude product obtained was 47.42 g (149.9 mmole, 60%). Ethanol (160 mL, 8 vols) was added to the crude product (20.00 g, 63.22 mmol, 1.0 eq). The mixture was stirred under nitrogen and warmed to 40° C. using a hot water bath. On reaching this temperature, all of the solid had dissolved to give a clear, yellow solution. Water (60 mL, 3 vols) was added dropwise over a period of 10 minutes, whilst the internal temperature was maintained in the range 38–41° C. The water bath was removed, and the solution was allowed to cool to 25° C. over 40 minutes, by which time crystallisation had begun. The mixture was cooled to −5° C. over 10 minutes, then held at this temperature for a further 10 minutes. The pale yellow solid was collected by filtration, suction dried for 10 minutes, then dried to constant weight in a vacuum oven (40° C., 15 hours). The mass of sub-title compound obtained was 18.51 g (58.51 mmol, 93% (from the crude product)).

(b) Compound A, benzenesulphonic acid salt monohydrate

To an ethanol solution (total volume 770 mL, approx. 20 vols with respect to the amine) of 3,3-dimethyl-1-(9-oxa-3,7-diazabicyclo[3.3.1]non-3-yl)-2-butanone (assumed 34.97 g (verified by assay), 154.5 mmol, 1.0 eq; see step (viii) above) was added 3-(4-cyanoanilino)propyl benzenesulfonate (49.05 g, 154.52 mmol, 1.0 eq; see step (a) above) in one portion. The resultant mixture was heated at 74° C. for 6 hours, then stirred at room temperature (20° C.) for 65 hours (over the weekend; the skilled person will appreciate that the reaction will also succeed without this prolonged stirring at room temperature). Ethanol (370 mL) was removed, and water (200 mL) was added (this gave a 2:1 EtOH:$H_2O$ mixture, total volume 600 mL). Upon adding the water, the pot temperature fell from 80° C. to 61° C. The solution was re-heated to 70° C., then allowed to cool naturally to ambient temperature overnight (19 hours), whilst stirring slowly. A solid was observed at this stage. The mixture was cooled to 0° C. and then stirred at this temperature for 15 minutes before collecting the off-white solid by filtration. The solid was washed with a cold 2:1 mixture of ethanol:water (150 mL), suction dried for 1.25 hours, then oven-dried (40° C., 20 hours). The mass of crude product obtained was 57.91 g (103.3 mmol, 60%).

The crude product was found to be 98.47% pure (as determined by HPLC analysis), and was recrystallised (using the procedure detailed below) to give the sub-title compound in a purity of 99.75% (84% recovery).

Recrystallisation procedure:

Ethanol (562 mL) and water (281 mL) were added to the crude product obtained above (56.2 g). The solution was heated to 75° C. All material dissolved at 55° C. The solution was held at 75° C. for 5 minutes, before being cooled to 5° C. over 1.5 hours. Precipitation started at 35° C. The cold solution was filtered and the collected precipitate was washed with ethanol:water (2:1, 168 mL). The solid material was sucked dry on the filter, before being dried in vacuo at 40° C. to give product (47.1 g, 84%).

(x) Compound A (Free Base)

Method I

Crude benzenesulphonate salt (50.0 g, 1.0 equiv, from step (ix) above; Method 1) was added to aqueous sodium hydroxide (1 M, 500 mL) washing in with dichloromethane (1.0 L, 20 vol). The combined mixture was stirred for 15 minutes. The layers were then separated and a small amount of interfacial material was left with the upper aqueous layer. Ethanol (500 mL, 10 vol) was added to the dichloromethane solution and then solvent was removed by distillation (1.25 L). The still head temperature was now at 78° C. The solution was allowed to cool to below reflux and ethanol (250 mL, 5 vol.) was added. Solvent was removed (250 mL). This warm solution was diluted with ethanol to 890 mL, 17.8 vol. (25 vol. assuming 100% conversion to free base). After heating to reflux the solution was cooled slowly. At 5° C. a seed of title compound was added. Crystallisation began and the mixture was stirred at 5° C. for 30 minutes. The product was collected by filtration and washed with ethanol (2×50 mL, 2×1 vol.). The product was then dried in a vacuum oven at 40° C. for 60 hours to give an off-white powder (26.3 g; 74%).

$^1$H NMR (400 MHz, CDCl$_3$): δ 7.86–7.82 (2H, m), 7.39–7.32 (3H, m), 7.30–7.26 (2H, m), 6.47 (2H, m), 4.11–4.07 (4H, m), 3.70 (2H, s), 3.36–3.33 (4H, m), 3.26 (2H, t), 3.12 (2H, d), 2.90 (2H, d), 2.28–2.21 (2H, m), 1.06 (9H, s) $^{13}$C NMR (CDCl$_3$): δ 24.07, 26.38, 41.52, 43.52, 56.17, 56.47, 63.17, 68.46, 96.61, 111.64, 121.03, 133.43. MS (ES): m/z=385.1 (M+H)$^+$

Method II

A mixture of 4-{[3-(9-oxa-3,7-diazabicyclo[3.3.1]non-3-yl)propyl]amino}-benzonitrile (see Preparation B(I)(vi) below; 5.73 g, 0.02 mol), K$_2$CO$_3$ (11.05 g, 0.08 mol) in MeCN (300 mL) was treated with 1-chloropinacolone (4.44 g, 0.032 mol). The mixture was stirred at 50° C. overnight before DCM was added and the mixture filtered. The filter cake was then washed with a mixture of DCM and MeCN before the solvent was evaporated from the filtrate. The resulting residue was purified by chromatography on silica, eluting with a gradient of ethyl acetate:methanol:ammoniacal methanol (95:5:0 to 95:0:5), to give the-title compound (5.8 g, 73.9%).

PREPARATION B(I)

Preparation of Compound B (Method I)

(i) tert-Butyl 2-bromoethylcarbamate

Sodium bicarbonate (6.15 g, 0.073 mol) and di-t-butyl dicarbonate (11.18 g, 0.051 mol) were dissolved in a mixture of H$_2$O (50 mL) and dichloromethane (150 mL), then cooled to 0° C. 2-Bromoethylamine hydrobromide (10.0 g, 0.049 mol) was added slowly as a solid, and the reaction was stirred overnight at 25° C. The dichloromethane layer was separated, washed with H$_2$O (200 mL) and washed with a solution of potassium hydrogensulphate (150 mL, pH 3.5). The organic layer was dried (Na$_2$SO$_4$) and concentrated in vacuo. The crude oil was chromatographed on silica gel, eluting with dichloromethane to afford 7.87 g (72%) of the sub-title compound as a clear, colorless oil.

$^1$H NMR (300 MHz, CDCl$_3$) δ 4.98 (bs, 1H), 3.45–3.57 (m, 4H), 1.47 (s, 9H) API-MS: (M+1-C$_5$H$_8$O$_2$) 126 m/z (ii) 3-Benzyl-9-oxa-3,7-diazabicyclo[3.3.1]nonane×2 HCl This is an alternative preparation to that described in Preparation A(vi) above. A 3 L, three-necked flask was equipped with a magnetic stirrer, a thermometer and a reflux condenser. Aqueous hydrobromic acid (48%, 0.76 L, 4.51 mol) was added to solid 3-benzyl-7-(phenylsulphonyl)-9-oxa-3,7-diazabicyclo[3.3.1]nonane (190 g, 0.53 mol, see Preparation A(v) above) and the mixture was heated to reflux under nitrogen. The solid dissolved at 90° C. After heating the mixture for 12 hours, GC analysis showed that the reaction was complete. The contents were cooled to room temperature. Toluene (0.6 L) was added and the mixture was stirred for a few minutes. The phases were separated. The aqueous phase was returned to the original reaction vessel and aqueous sodium hydroxide (10 M, 0.85 L, 8.5 mol) was added in one portion. The internal temperature rose to 80° C. and the mixture was strongly basic. Toluene (0.8 L) was added when the internal temperature dropped to 55° C. After stirring vigorously for 30 minutes, the toluene phase was separated and returned to the original reaction vessel. 2-Propanol (1.9 L) was added and the internal temperature was adjusted to between 40° C. and 50° C. Concentrated hydrochloric acid was added (until acidic) at such a rate to maintain the temperature between 40° C. and 50° C. A white precipitate formed. The mixture was stirred for 30 minutes and then cooled to 7° C. The white powder was collected by filtration, washed with 2-propanol (0.4 L), dried by pulling air through the sample for ten minutes, and then further dried in a vacuum oven at 40° C. Yield: 130 g (84%).

(iii) tert-Butyl 7-benzyl-9-oxa-3,7-diazabicyclo[3.3.1]nonane-3-carboxylate hydrochloride A 5 L, three-necked flask was equipped with an overhead stirrer, a thermometer and a nitrogen bubbler. Water (1.4 L), dichloromethane (1.4 L), sodium bicarbonate (150 g, 1.79 mol) and 3-benzyl-9-oxa-3,7-diazabicyclo[3.3.1]nonane×2 HCl (130 g, 0447 mol, from step (ii) above) were all charged in order. The mixture was stirred rapidly for ten minutes and then di-tert-butyl dicarbonate (0.113 L, 0.491 mol) was added slowly. The mixture was stirred rapidly for three hours at room temperature. The organic layer was separated, dried with magnesium sulfate, filtered and concentrated to afford 160 g of an off-white solid. The off-white solid was charged into a 3L, three-necked flask equipped with an overhead stirrer, a thermometer and an addition funnel. Ethyl acetate (0.6 L) was charged and the clear solution was cooled to −10° C. A solution of HCl in dioxane (4 M) was added dropwise until the pH was less than 4. The hydrochloride salt precipitated and the mixture was stirred for an additional hour. The product was collected by filtration, washed with ethyl acetate (0.1 L), and dried overnight in a vacuum oven. The white crystalline product weighed 146 g (92% yield).

(iv) tert-Butyl 9-oxa-3,7-diazabicyclo[3.3.1]nonane-3-carboxylate hydrochloride Hydrochloride salt from step (iii) above (146 g, 0.411 mol) and 20% Pd(OH)$_2$-C (7.5 g) were charged to a Parr hydrogenator bottle. Methanol (0.5 L) was added and the bottle was shaken vigorously under an atmosphere of hydrogen at 3.5 bar. The reaction was monitored by GC analysis and was found to be complete after one hour. The catalyst was filtered and the filtrate was concentrated to afford an off-white crystalline product. The crude product was dissolved in hot acetonitrile (1.2 L), and then filtered while hot. The filtrate was diluted with ethyl acetate (1.2 L). The clear solution was allowed to stand overnight at room temperature. The first crop of crystals was collected and dried under vacuum to afford 52 g of sub-title compound as a white solid. The filtrate was concentrated to near dryness, then dissolved in hot acetonitrile (0.4 L), and diluted with ethyl acetate (0.4 L). A second crop of crystals (38 g) was obtained after cooling the solution to 10° C. Both crops were found to be comparable by GC analysis and $^1$H NMR analyses. Combined yield: 90 g (83%).

(v) tert-Butyl 7-[3-(4-cyanoanilino)propyl]-9-oxa-3,7-diazabicyclo[3.3.1]-nonane-3-carboxylate The hydrochloride salt of tert-butyl 9-oxa-3,7-diazabicyclo[3.3.1]nonane-3-carboxylate (see step (iv) above; 1.1 g, 4.15 mmol) was mixed with MeCN (46 mL), water (2.5 mL) and K$_2$CO$_3$ (3.5 g, 25 mmol). The mixture was stirred for 4 h before CHCl$_3$ was added and the mixture was filtered through Celite®. The filtrate was concentrated in vacuo to give 0.933 g of the free base. This was then mixed with 3-(4-cyanoanilino)propyl 4-methylbenzenesulphonate (see Preparation A(ii) above; 2.1 g, 6.2 mmol) and K$_2$CO$_3$ (0.86 g, 6.2 mmol) in MeCN (18 mL). The resulting mixture was stirred overnight at 60° C. before being concentrated in vacuo. The residue was treated with DCM (250 mL) and 1 M NaOH (50 mL). The layers were separated and the DCM layer washed twice with aqueous NaHCO$_3$, before being dried (Na$_2$SO$_4$) and concentrated in vacuo. The product was purified by flash chromatography, eluting with a gradient of toluene:ethyl acetate:triethylamine (2:1:0 to 1000:1000:1), to give 1.47 g (91%) of the sub-title compound.

(vi) 4-{[3-(9-Oxa-3,7-diazabicyclo[3.3.1]non-3-yl)propyl]amino}benzonitrile

The sub-title compound was obtained in 96% yield using an analogous procedure to those described in Preparations C(v) and D(iii) below, using tert-butyl 7-[3-(4-cyanoanilino)propyl]-9-oxa-3,7-diazabicyclo[3.3.1]-nonane-3-carboxylate (from step (v) above).

(vii) Compound B

To a solution of tert-butyl 2-bromoethylcarbamate (4.21 g, 0.019 mol; see step (i) above) in DMF (65 mL) was added 4-{[3-(9-oxa-3,7-diazabicyclo[3.3.1]non-3-yl)propyl]amino}benzonitrile (see step (vi) above, 4.48 g, 0.016 mol) and triethylamine (3.27 mL, 0.024 mol). The mixture was stirred overnight at 35° C. and then concentrated in vacuo. The residue was dissolved in dichloromethane (80 mL) and washed with saturated sodium chloride. The aqueous layer was extracted with dichloromethane (1×150 mL). The combined organic extracts were dried (Na$_2$SO$_4$) and concentrated in vacuo. The crude red-brown oil was chromatographed (×2) on silica gel eluting with chloroform:methanol:conc. NH$_4$OH (9:1:0.02) to afford 3.75 g (56%) of the title compound.

$^1$H NMR (300 MHz, CD$_3$OD) δ 7.37–7.40 (d, J=8.8 Hz, 2H), 6.64–6.67 (d, J=8.8 Hz, 2H), 3.94 (bs, 2H), 3.21–3.31 (m, 4H), 3.01 (bs, 4H), 2.47–2.59 (m, 8H), 1.90 (bs, 2H), 1.39 (s, 9H) $^{13}$C NMR (75 MHz, CD$_3$OD) δ 158.5, 134.7, 121.9, 113.2, 97.7, 80.3, 69.2, 58.8, 58.1, 57.5, 57.3, 41.9, 38.3, 28.9, 26.2. API-MS: (M+1)=430 m/z

PREPARATION B(II)

Preparation of Compound B (Method II)

(i) [2-(7-Benzyl-9-oxa-3,7-diazabicyclo[3.3.1]non-3-yl)ethyl]carbamic acid tert-butyl ester Alternative 1

(a) 2-(tert-Butyloxycarbonylamino)ethyl tosylate

A solution of p-toluenesulfonyl chloride (28.40 g, 148 mmol) in dichloromethane (100 mL) was added dropwise over 30 minutes at 0° C. to a mixture of tert-butyl N-(2-hydroxyethyl)carbamate (20 g, 120 mmol), triethylamine (18.80 g, 186 mmol) and trimethylammonium chloride (1.18 g, 12.4 mmol) in dichloromethane (120 mL). The mixture was stirred at 0° C. for 1 hour then filtered, washing with dichloromethane (100 mL). The filtrate was washed with 10% citric acid (3×100 mL) and brine (100 mL). The organic layer was dried with magnesium sulfate and then filtered. The filtrate was concentrated under reduced pressure to give an oil. The oil was dissolved in ethyl acetate (40 mL) and then iso-hexane (160 mL) was added slowly. The resultant slurry was stirred at room temperature for 17 hours and then filtered. The collected solid was washed with iso-hexane (240 mL) to yield the sub-title compound as a colourless powder (25 g, 64%).

m.p. 64–66° C. $^1$H-NMR (300 MHz, CDCl$_3$) δ 1.40 (9H, s), 2.45 (3H, s), 3.38 (2H, q), 4.07 (2H, t), 4.83 (1H, bs) 7.34 (2H, d), 7.87 (2H, d). MS: m/z=216 (MH$^+$(316)—Boc).

(b) [2-(7-Benzyl-9-oxa-3,7-diazabicyclo[3.3.1]non-3-yl)ethyl]carbamic acid tert-butyl ester A solution of 3-benzyl-9-oxa-3,7-diazabicyclo[3.3.1]nonane dihydrochloride (see Preparation A(vi) above; 10 g, 34 mmol) in water (25 mL) was added slowly to a solution of sodium bicarbonate (10 g, 119 mmol) in water 10 mL). More water (5 mL) was added and the mixture was stirred at room temperature for 10 minutes. A solution of 2-(tert-butyloxycarbonylamino)ethyl tosylate (see step (a) above; 11.92 g, 37 mmol) in toluene (40 mL) was added. This mixture was then heated at 65–70° C. for 7 hours before stirring at room temperature overnight. The reaction was reheated to 50° C. and the phases were separated. The aqueous layer was extracted with toluene (40 mL) at 50° C. The combined organic layers were washed with saturated sodium bicarbonate (25 mL). The solvents were evaporated under reduced pressure to yield a mixture of oil and solid (13 g, >100%). Ethyl acetate (50 mL) and citric acid (10%, 25 mL) were added to a portion of the oily solid (5 g, 138 mmol). The aqueous layer was separated and the organic layer washed again with citric acid (10%, 20 mL). The aqueous layers were combined and treated with solid sodium bicarbonate until neutral. The aqueous phase was extracted with ethyl acetate (2×50 mL), dried over magnesium sulfate and filtered. The filtrate was evaporated to dryness under reduced pressure to give the sub-title compound as a colourless semi-solid, which solidified fully when stored in the refrigerator (4.68 g, 93%).

m.p. 58–60° C.

$^1$H-NMR (300 MHz, CDCl$_3$) δ 1.46 (9H, s), 2.38–2.57 (4H, m), 2.6–2.68 (2H, m) 2.75–2.85 (4H, m), 3.22 (2H, q), 3.26 (2H, s), 3.83 (2H, bs), 6.17 (1H, bs) 7.2–7.4 (5H, m). MS: m/z=362 (MH$^+$).

Alternative 2

(a) 3-(7-Benzyl-9-oxa-3,7-diazabicyclo[3.3.1]non-3-yl)ethyl]propionamide

Triethylamine (3.60 g, 35.7 mmol) was added slowly to a solution of 3-benzyl-9-oxa-3,7-diazabicyclo[3.3.1]nonane dihydrochloride (see Preparation A(vi) above; 5 g, 17 mmol) in ethanol (50 mL). Acrylamide (1.34 g, 18 mmol) was added to this mixture, which was then heated at reflux for 7 hours. The reaction mixture was then concentrated under reduced pressure. Water (50 mL) and sodium hydroxide (1 M, 150 mL) were added to the residue and the mixture extracted with ethyl acetate (2×200 mL). The combined organic extracts were dried over magnesium sulfate, filtered and concentrated under reduced pressure to give a colourless solid. This was recrystallised from ethyl acetate (50 mL) to give the sub-title compound (3.80 g, 76%).

m.p. 157–159° C. $^1$H-NMR (300 MHz, CDCl$_3$) δ 2.39 (2H, t), 2.42–2.61 (6H, m), 2.82–2.95 (4H, m), 3.39 (2H, s), 3.91 (2H, bs), 5.07 (1H, bs), 7.18–7.21 (2H, m), 7.25–7.39 (3H, m), 9.5 (1H, bs). MS: m/z=290 (MH$^+$).

(b) [2-(7-Benzyl-9-oxa-3,7-diazabicyclo[3.3.1]non-3-yl)ethyl]carbamic acid tert-butyl ester N-Bromosuccinimide (6.0 g, 33 mmol) was added in portions over 1 minute to a solution of 3-(7-benzyl-9-oxa-3,7-diazabicyclo[3.3.1]non-3-yl)ethyl]-propionamide (see step (a) above; 5 g, 12 mmol) in potassium tert-butoxide in tert-butanol (1 M, 81 mL) and tert-butanol (20 mL). The mixture was then heated at 60–65° C. for 30 minutes. The reaction was allowed to come to room temperature and then water (100 mL) was added. The mixture was extracted with ethyl acetate (2×50 mL). The combined organic extracts were washed with brine (50 mL), dried over magnesium sulfate, filtered (washing the filter cake with ethyl acetate (50 mL)) and then the filtrate concentrated under reduced pressure to give the sub-title compound as a brown oil (6.5 g, >100%).

$^1$H-NMR (300 MHz, CDCl$_3$) δ 1.46 (9H, s), 2.4–2.58 (4H, m), 2.58–2.7 (2H, m) 2.75–2.91 (4H, m), 3.22 (2H, q), 3.28 (2H, s), 3.83 (2H, bs), 6.19 (1H, bs) 7.2–7.42 (5H, m). MS: m/z=316 (M$^+$).

Alternative 3

(a) 3-Benzyl-9-oxa-3,7-diazabicyclo[3.3.1]nonane

All volumes and equivalents are measured with respect to the amount of 3-benzyl-9-oxa-3,7-diazabicyclo[3.3.1]nonane dihydrochloride (see Preparation A(vi) above) used. Toluene (420 mL, 7 vols) and aqueous sodium hydroxide solution (2 M, 420 mL, 7 vols, 4.0 eq) were added to 3-benzyl-9-oxa-3,7-diazabicyclo[3.3.1]nonane dihydrochloride (60.07 g, 206.03 mmole, 1.0 eq., see Preparation A(vi) above). The mixture was stirred under nitrogen, heated to 60° C. and held at this temperature for 30 minutes by which time two clear layers had formed. The lower, aqueous layer was removed, and the toluene solution of sub-title compound (free base) was azeodried at atmospheric pressure (total volume of solvent removed=430 mL; total volume of toluene added=430 mL), then concentrated to a volume of 240 mL (4 vols). Karl Fischer analysis at this stage showed 0.06% water in the solution. The dried solution of sub-title compound (theoretically 44.98 g, 206.03 mmole, 1.0 eq) was used as such in a subsequent step.

(b) 2-(tert-Butyloxycarbonylamino)ethyl 2,4,6-trimethylbenzenesulfonate

Triethylamine (65 mL, 465.3 mmole, 1.5 eq) was added in one portion to a solution of tert-butyl N-(2-hydroxyethyl) carbamate (50.11 g, 310.2 mmole, 1.0 eq.) in dichloromethane (250 mL, 5 vols). The solution was cooled to −10° C. and trimethylamine hydrochloride (14.84 g, 155.1 mmole, 0.5 eq.) was added in one portion. The resultant mixture was cooled further to −15° C., stirred for 5 minutes, then treated with a solution of mesitylenesulfonyl chloride (74.74 g, 341.2 mmole, 1.1 eq) in dichloromethane (250 mL, 5 vols), over 28 minutes such that the internal temperature remained below −10° C. Once the addition was complete a precipitate had formed and the mixture was stirred at −10° C. for a further 30 minutes. Water (400 mL, 8 vols) was added and all of the precipitate dissolved. The mixture was stirred rapidly for 5 minutes, and then the two layers were separated. A solvent swap from dichloromethane to isopropanol was carried out by distillation at reduced pressure. Solvent was removed (450 mL) and replaced with iso-propanol (450 mL (initial pressure was 450 mbar, b.p. 24° C.; final pressure was 110 mbar, b.p. 36° C.). At the end of the distillation, solvent (150 mL) was removed to bring the volume down to 350 mL (7 vols with respect to the amount of tert-butyl N-(2-hydroxyethyl)carbamate used). The solution was cooled to 25° C., then water (175 mL) was added slowly with stirring, causing the solution gradually to turn cloudy. No solid had precipitated at this stage. More water (125 mL) was added, and a solid precipitate started to form after about 75 mL had been added. The internal temperature rose from 25° C. to 31° C. The mixture was stirred slowly and cooled to 7° C. The solid was collected by filtration, washed with iso-propanol:water (1:1, 150 mL) and dried in vacuo at 40° C. for 21 hours to give the sub-title compound as a white crystalline solid (92.54 g, 87%).

m.p. 73.5° C. $^1$H-NMR (300 MHz, CDCl$_3$) δ 1.42 (9H, s), 2.31 (3H, s), 2.62 (6H, s) 3.40 (2H, q), 4.01 (2H, t), 4.83 (1H, bs), 6.98 (2H, s)

(c) [2-(7-Benzyl-9-oxa-3,7-diazabicyclo[3.3.1]non-3-yl)ethyl]carbamic acid tert-butyl ester, 2,4,6-trimethylbenzenesulfonic acid salt A warm (28° C.) solution of 2-(tert-butyloxycarbonylamino)ethyl 2,4,6-trimethylbenzenesulfonate (70.93 g, 206.03 mmole, 1.0 eq, see step (b) above) in toluene (240 mL, 4 vols) was added to a solution of 3-benzyl-9-oxa-3,7-diazabicyclo[3.3.1]nonane (44.98 g, 206.03 mmole, 1.0 eq.) in toluene (240 mL, 4 vols) (see step (a) above). The resultant solution was stirred rapidly under nitrogen, with heating at 68° C. for 8 hours. The reaction was left to stir at ambient temperature for 84 hours. A thick, white solid precipitate had formed in a pale yellow solution. The mixture was cooled to +9° C., and sub-title compound was collected by filtration. The reaction vessel was washed with toluene (100 mL) and added to the filter. The filter cake was washed with toluene (150 mL). The white solid product was suction dried for 15 minutes, then dried to constant weight in vacuo at 40° C. for 23 hours. The yield of sub-title compound obtained was 79.61 g, 141.7 mmole, 69%. The combined filtrate and washings (670 mL) were washed with aqueous sodium hydroxide solution (2 M, 200 mL, 3.3 vols). The mixture was heated to 60° C., and held at this temperature for 20 minutes with rapid stirring. The two layers were then separated. The toluene solution was concentrated to 200 mL by vacuum distillation (bp 50–54° C. at 650–700 mbar; bp 46° C. at 120 mbar at the end). As the distillation progressed, the solution became cloudy due to the formation of sub-title compound. It was assumed that 20% of the original amount of 3-benzyl-9-oxa-3,7-diazabicyclo[3.3.1]nonane remained in the filtrate, and so extra 2-(tert-butyloxycarbonylamino)ethyl 2,4,6-trimethylbenzenesulfonate (14.20 g, 41.21 mmole, 0.2 eq) was added in one portion (charged as a solid rather than as a solution in toluene). The cloudy solution was heated at 67° C. for 8 hours with rapid stirring, and then left to stir at ambient temperature for 11 hours. The mixture was cooled to +8° C., and sub-title compound was collected by filtration. The reaction vessel was washed with more toluene (2×30 mL), and added to the filter. The white solid product was suction dried for 15 minutes, then dried to constant weight in vacuo at 40° C. for 7 hours. The yield of sub-title compound was 23.25 g, 41.39 mmole, 20%. The combined yield of sub-title compound (a white solid) was 102.86 g, 183.11 mmole, 89%.

m.p. 190–190.5° C. 1H-NMR (300 MHz, CDCl$_3$) δ 1.43 (9H, s), 2.17 (3H, s), 2.51 (6H, s), 2.73–2.80 (2H, m), 2.90–2.94 (4H, m), 3.14–3.22 (4H, m), 3.37 (2H, bm), 3.89 (2H, bs), 4.13 (2H, bs), 6.74 (2H, s), 7.12 (1H, bt), 7.42–7.46 (5H, m)

(ii) [2-(9-Oxa-3,7-diazabicyclo[3.3.1]non-3-yl)ethyl]carbamic acid tert-butyl ester Method 1: Sodium bicarbonate (0.058 g, 0.069 mmol) and 5% Pd/C (0.250 g, Johnson Matthey Type 440 paste) were added to a solution of [2-(7-benzyl-9-oxa-3,7-diazabicyclo[3.3.1]non-3-yl)ethyl]carbamic acid tert-butyl ester (see step (i), Alternative 1 above; 1 g, 2.77 mmol) in ethanol (10 mL). The mixture was then hydrogenated at 500 kPa (5 bar) for 18 hours. The reaction mixture was filtered through Celite® and then washed with ethanol (20 mL). The solution was concentrated under reduced pressure to give an oil. This was dissolved in dichloromethane (20 mL) and washed with sodium hydroxide (1 M, 10 mL). The organic phase was separated, dried over magnesium sulfate and then filtered. The filtrate was concentrated under reduced pressure to give the sub-title compound as a yellow solid (0.67 g, 87%).

m.p. 91–93° C. $^1$H-NMR (300 MHz, CDCl$_3$) δ 1.46 (9H, s), 2.25 (2H, t), 2.58–2.65 (2H, m) 2.95–3.06 (4H, m), 3.2–3.38 (4H, m), 3.64 (2H, bs), 4.65 (1H, bs). MS: m/z=272 (MH$^+$).

Method 2: [2-(7-Benzyl-9-oxa-3,7-diazabicyclo[3.3.1]non-3-yl)ethyl]-carbamic acid tert-butyl ester 2,4,6-trimethylbenzenesulfonic acid salt (320 g, 1.0 mol eq, 1.0 rel vol/wt, see step (i), Alternative 3 above), toluene (640 mL, 2.0 vol) and aqueous sodium hydroxide (1 M, 1.6 L, 5.0 vol) were stirred together for 15 minutes and the layers were then separated. The organic layer, containing [2-(7-benzyl-9-oxa-3,7-diazabicyclo[3.3.1]non-3-yl)ethyl]carbamic acid tert-butyl ester, was diluted with ethanol (690 mL, 2.16 vol) and water (130 mL, 0.4 vol). Citric acid (32.83g, 0.3 mol eq) and 5% Pd/C (20.8 g, 0.065 wt eq of 61% water wet catalyst, Johnson Matthey type 440L) were added. The combined mixture was then hydrogenated under 4 bar of hydrogen pressure for 24 hours. The reaction was monitored by TLC, using a silica plate with mobile phase X:DCM (1:1 v/v; X is chloroform:methanol:concentrated ammonia 80:18:2 v/v). Visualisation was by UV light (254 nm) and by staining with aqueous potassium permanganate. This showed the complete disappearance of starting material and the appearance of the sub-title compound. The reaction mixture was filtered through kieselguhr and was washed with ethanol (590 mL, 1.84 vol). The resulting solution of sub-title compound (assumed 154.85 g, 100%) was used directly in a subsequent reaction.

Method 3: [2-(7-Benzyl-9-oxa-3,7-diazabicyclo[3.3.1]non-3-yl)ethyl]-carbamic acid tert-butyl ester 2,4,6-trimethylbenzenesulfonic acid salt (50 g, 1.0 mol eq., 1.0 rel vol/wt, see step (i), Alternative 3 above), toluene (100 mL, 2.0 vol) and aqueous sodium hydroxide (1 M, 100 L, 2.0 vol) were stirred together for 20 minutes, then at 30° C. for 10 minutes, and the layers were then separated. The organic layer, containing [2-(7-benzyl-9-oxa-3,7-diazabicyclo[3.3.1]non-3-yl)ethyl]carbamic acid tert-butyl ester, was diluted with ethanol (100 mL, 2.0 vol.). To this was added a solution of citric acid (5.14 g, 0.3 mol eq) in water (5 mL, 0.1 vol), followed by 5% Pd/C (1.50 g, 0.03 wt eq of 61% water wet catalyst, Johnson Matthey type 440 L). The combined mixture was then hydrogenated under 4 bar of hydrogen pressure lo for 24 hours. The reaction was monitored by TLC, using a silica plate with mobile phase X:DCM 1:1 v/v, (X is chloroform:methanol:concentrated ammonia 80:18:2 v/v). Visualisation was by UV light (254 nm) and by staining with aqueous potassium permanganate. This showed the complete disappearance of starting material and the appearance of the sub-title compound. The reaction mixture was basified with aqueous sodium hydroxide (10 M, 8 mL, 0.9 mol eq), then filtered through kieselguhr. The filter-cake was washed with ethanol (100 mL, 2.0 vol). The resulting solution of sub-title compound (assumed 24.15 g, 100%) was used directly in a subsequent reaction.

(iii) Compound B

Method I 3-(4-Cyanoanilino)propyl-4-methylbenzenesulfonate (see Preparation A(ii) above; 0.30 g, 0.92 mmol) and potassium carbonate (0.2 g, 1.38 mmol) were added to a solution of [2-(9-oxa-3,7-diazabicyclo[3.3.1]non-3-yl)ethyl]carbamic acid tert-butyl ester (see step (ii), Method 1 above; 0.250 g, 0.92 mmol) in ethanol (5 mL). The reaction mixture was heated to 70° C. for 10 hours before concentrating the mixture under reduced pressure. The residue was partitioned between ethyl acetate (20 mL) and sodium hydroxide (1 M, 10 mL). The aqueous phase was re-extracted with ethyl acetate (20 mL). The combined organic phases were concentrated under reduced pressure to give a yellow solid (0.290 g). The solid was dissolved in ethyl acetate (10 mL) and this solution washed with a solution of citric acid (0.250 g) in water (10 mL). The aqueous phase was separated, basified with sodium hydroxide (1 M, 10 mL) and extracted with ethyl acetate (2×10 mL). All organic phases were combined, dried over magnesium sulfate and then filtered (washing filtered solids with ethyl acetate (10 mL)). The filtrate was concentrated under reduced pressure to give a yellow solid (0.160 g). This was slurried in ethyl acetate (0.2 mL) and then filtered to give title compound (0.050 g, 12%).

m.p 113–115° C. $^1$H-NMR (400 MHz, DMSO-D$_6$) δ 1.32 (9H, s), 1.7 (2H, qt), 2.20 (2H, t), 2.22–2.3 (4H, m), 2.38–3.1

(2H, m) 2.8–2.85 (4H, m), 3.05 (2H, q), 3.19 (2H), q), 3.79 (2H, bs), 6.47 (1H, t), 6.66 (2H, d), 6.69 (1H, t), 7.41 (2H, d). MS: m/z=430 (MH+).

Method II

To the solution of [2-(9-oxa-3,7-diazabicyclo[3.3.1]non-3-yl)ethyl]carbamic acid tert-butyl ester generated in step (ii) (Method 3) above (assumed 24.15 g, 1.0 mol eq., 1.0 wt./vol.) in a mixture of toluene (approx. 100 mL), ethanol (approx. 200 mL) and water (approx. 14 mL), was added anhydrous potassium carbonate (18.58 g, 1.5 mol eq.). Solid 3-(4-cyanoanilino)propyl benzenesulfonate (28.17 g, 1.0 mol eq., see Preparation A(ix), Method 2, step (a) above) was added and the combined mixture was heated to 70° C. for six hours. The reaction was monitored by TLC using a silica plate with mobile phase X:DCM 1:1 v/v (in which X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was cooled, and the solvent was concentrated in vacuo. The residue was partitioned between toluene (200 mL) and water (200 mL). The layers were separated, and the organic phase was concentrated in vacuo to afford a yellow solid (38.6 g).

PREPARATION C

Preparation of Compound C (i) 4-(4-Cyanophenyl)but-3-yn-1-ol

Potassium carbonate (376.7 g, 2.5 mol eq.) was dissolved in a mixture of 1,2-dimethoxyethane (DME, 1.2 L, 6 vol) and water (1.2 L, 6 vol). Palladium on charcoal (20 g, 0.01 mol eq., 10% Johnson Matthey type 87L, 60% water), triphenylphosphine (11.5 g, 0.04 mol eq.) and copper(I) iodide (4.2 g, 0.02 mol eq.) were added. 4-Bromobenzonitrile (200 g, 1 mol eq.) was then added, washing in with a mixture of DME (200 mL, 1 vol) and water (200 mL, 1 vol). This mixture was stirred rapidly under nitrogen for a minimum of thirty minutes. A solution of but-3-yn-1-ol (92.1 mL, 1.1 mol eq) in DME (200 mL, 1 vol) and water (200 mL, 1 vol) was added dropwise over five minutes. The combined mixture was then heated to 80° C. for three hours. The reaction was monitored by HPLC for the disappearance of arylbromide and the formation of sub-title compound. Once all of the starting material had been consumed, the reaction was cooled to 25° C. and filtered through kieselguhr. The filter cake was washed separately with toluene (1.6 L, 8 vol). The DME:water mixture was partially concentrated in vacuo to remove the majority of the DME. This was then partitioned with the toluene wash. The toluene layer was concentrated in vacuo to give sub-title alkyne as a yellow solid, which was dried in a vacuum oven overnight at 40° C. Yield 182.88 g, 97%.

$^1$H NMR (300 MHz, CDCl$_3$) δ 7.599–7.575 (d, J=7.2 Hz, 2H, CH), 7.501–7.476 (d, J=7.5 Hz, 2H, CH), 3.880–3.813 (q, 2H, CH$_2$), 2.751–2.705 (t, 2H, CH$_2$), 1.791–1.746 (t, 1H, OH) mp 79.6–80.5° C.

(ii) 4-(4-Hydroxybutyl)benzonitrile 4-(4-Cyanophenyl)but-3-yn-1-ol (40 g, 1 wt eq, see step (i) above) in ethanol (200 mL, 5 vol) and palladium on charcoal (20 g, 0.5 wt eq, 10% Johnson Matthey type 487, 60% water) were stirred rapidly under five bar hydrogen pressure for five hours. The reaction was monitored by HPLC for the disappearance of the starting material, and the formation of sub-title compound. The reaction was filtered through kieselguhr and washed with ethanol (80 mL, 2 vol). The ethanol solution was concentrated in vacuo to give sub-title alcohol as a yellow-brown oil. Yield 36.2g, 88.5%.

$^1$H NMR (300 MHz, CDCl$_3$) δ 7.550–7.578 (d, J=8.4 Hz, 2H), 7.271–7.298 (d, J=8.1 Hz, 2H), 3.646–3.688 (t, 2H), 2.683–2.733 (t, 2H), 1.553–1.752 (m, 4H) $^{13}$C NMR (300 MHz, CDCl$_3$) δ 148.04 (C), 132.16 (C), 119.1(C), 109.64 (C), 62.46 (C), 35.77 (C), 32.08 (C), 27.12 (C).

(iii) 4-(4-Cyanophenyl)butyl toluenesulphonate

The sub-title compound was prepared by addition of toluenesulphonyl chloride to 4-(4-hydroxybutyl)benzonitrile (see step (ii) above).

(iv) tert-Butyl 7-[4-(4-cyanophenyl)butyl]-9-oxa-3,7-diazabicyclo[3.3.1]-nonane-3-carboxylate A 2 L three-necked flask was equipped with a magnetic stirrer, a thermometer and a reflux condenser. The flask was charged with a solution of 4-(4-cyanophenyl)butyl toluenesulphonate (72 g, 0.218 mol, see step (iii) above) in dimethylformamide (0.55 L). tert-Butyl 9-oxa-3,7-diazabicyclo[3.3.1]nonane-3-carboxylate hydrochloride (48.2, 0.182 mol, see Preparation B(I)(iv) above) was added, followed by potassium carbonate (62.9 g, 0.455 mol). The heterogeneous mixture was stirred for 22 hours at 85° C. TLC analysis indicated complete consumption of starting material. The reaction mixture was cooled to room temperature and diluted with water (0.5 L). The mixture was extracted with ethyl acetate (3×0.4 L) and the organic fractions were combined. After washing with Water (2×200 mL) and brine (200 mL), the organic layer was dried with magnesium sulfate, filtered and concentrated under vacuum. The crude brown oil was purified by chromatography on silica gel, eluting with 3:2 hexanes/ethyl acetate affording 34 g (48% yield) of sub-title compound as an off-white solid.

(v) 4-[4-(9-Oxa-3,7-diazabicyclo[3.3.1]non-3-yl) butyl]benzonitrile

A 2 L three-necked flask was equipped with a magnetic stirrer, a thermometer and an addition funnel. The flask was charged with tert-butyl 7-[4-(4-cyanophenyl)butyl]-9-oxa-3, 7-diazabicyclo[3.3.1]-nonane-3-carboxylate (34 g, 88 mmol, from step (iv) above) and dichloromethane (440 mL). Trifluoroacetic acid (132 mL) was added slowly at room temperature. The solution was stirred for three hours at which point TLC analysis showed complete consumption of starting material. The contents were transferred to a single-necked flask and concentrated under vacuum. The residue was dissolved in dichloromethane (500 mL) and washed with saturated sodium bicarbonate solution. The aqueous layer was separated and extracted with dichloromethane (2×200 mL). The combined organic layers were washed with brine (200 mL), dried over magnesium sulfate and concentrated under vacuum to afford 25.8 g (100% yield) of sub-title compound as an off-white solid. The crude material was used in the next step without farther purification.

(vi) Compound C

A 3 L three-necked flask was equipped with a magnetic stirrer, a thermometer and a reflux condenser. The flask was charged with unpurified 4-[4-(9-oxa-3,7-diazabicyclo[3.3.1]

non-3-yl)butyl]benzonitrile (25.8 g, 88 mmol, from step (v) above), dichloromethane (0.88 L) and tert-butyl 2-bromoethylcarbamate (see Preparation B(I)(i) above, 27.7 g, 123 mmol). Triethylamine (0.0197 L, 0.141 mol) was then added. The clear solution was refluxed for 12 hours under a nitrogen atmosphere and then cooled to room temperature. The progress of the reaction was monitored by TLC analysis and it was found to be complete at this point. The reaction mixture was transferred to a separating funnel and washed sequentially with water (200 mL), 15% aqueous sodium hydroxide (200 mL), water (200 mL), and brine (200 mL). The organic-layer was dried over magnesium sulfate and concentrated under vacuum. The resulting yellow viscous oil was chromatographed on silica gel, eluting first with 9:1 dichloromethane/methanol, then with 9:1:0.02 dichloromethane/methanol/28% aqueous ammonium hydroxide to afford the title compound (25.1 g, 66% yield) as an off-white solid. The earlier fractions (5.1 g) from chromatography were found to contain a small amount of a less polar impurity (by TLC analysis) eluting with 9:1:0.05 dichloromethane/methanol/28% aqueous ammonium hydroxide) while the later factions (20 g) were one spot by TLC analysis. The earlier fractions (5.1 g) were combined with another lot of title compound (7.1 g, containing a slight impurity) and chromatographed on silica gel, eluting first with 19:1 dichloromethane/methanol, and then with 9:1 dichloromethane/methanol to afford a pale yellow powder (5.5 g). The powder was dissolved in dichloromethane (200 mL). The resulting solution was washed sequentially with 25% aqueous sodium hydroxide (50 mL), water (50 mL), and brine (40 mL). The material was then dried over magnesium sulfate and concentrated under vacuum to afford title compound as an off-white powder (5 g). The 20 g fraction was dissolved in dichloromethane (500 mL). The organic layer was washed sequentially with 25% aqueous sodium hydroxide (100 mL), water (100 mL), and brine (100 mL). The material was then dried over magnesium sulfate and concentrated under vacuum to afford title compound as an off-white powder (19 g). The lots were blended together.

PREPARATION D

Preparation of Compound D (i) 4-[(2S)-Oxiranylmethoxy]benzonitrile

Potassium carbonate (414 g) and (R)-(−)-epichlorohydrin (800 mL) were added to a stirred solution of p-cyanophenol (238 g) in 2.0 L MeCN and the reaction mixture was refluxed under an inert atmosphere for 2 h. The hot solution was filtered and the filtrate concentrated, giving a clear oil which was crystallised from di-iso-propyl ether giving the product in 90% yield.

(ii) tert-Butyl 7-[(2S)-3-(4-cyanophenoxy)-2-hydroxypropyl]-9-oxa-3,7-diazabicyclo[3.3.1]nonane-3-carboxylate A 3 L, three-necked flask equipped with a magnetic stirrer and a thermometer was charged with tert-butyl 9-oxa-3,7-diazabicyclo[3.3.1]nonane-3-carboxylate as its free base (53.7 g, 0.235 mol, obtained from the hydrochloride salt, see Preparation B(I)(iv) above), 4-[(2S)-oxiranylmethoxy]benzonitrile (41.2 g, 0.235 mol, see step (i) above), and a 10:1 (v/v) solution of 2-propanol/water (0.94 L). The mixture was stirred at 60° C. for 20 hours, during which time the starting materials were gradually consumed (assay by TLC analysis). The mixture was cooled and concentrated under vacuum to afford 100 g (>100% yield) of sub-title compound as white solid. The unpurified material was used in the next step.

(iii) 4-{[(2S)-2-Hydroxy-3-(9-oxa-3,7-diazabicyclo[3.3.1]non-3-yl)propyl]-oxy}benzonitrile A 3 L, three-necked flask equipped with a magnetic stirrer, a thermometer and an addition funnel was charged with unpurified tert-butyl 7-[(2S)-3-(4-cyanophenoxy)-2-hydroxypropyl]-9-oxa-3,7-diazabicyclo[3.3.1]nonane-3-carboxylate (100 g, from step (ii) above) and dichloromethane (1.15 L). Trifluoroacetic acid (0.352 L) was added slowly at room temperature and the resulting solution was stirred for three hours, at which point TLC analysis showed complete reaction. The contents were transferred to a single-necked flask and concentrated under vacuum. The residue was dissolved in dichloromethane (1.2 L) and washed with saturated sodium bicarbonate. The aqueous layer was separated and extracted with dichloromethane (2×0.2 L). The combined organic layers were washed with brine (0.25 L), dried over magnesium sulfate and concentrated under vacuum to afford 73 g (>100% yield) of sub-title compound as an off-white solid. The unpurified material was used in the next step.

(iv) Compound D

Method I A 2 L, three-necked flask was equipped with a magnetic stirrer, a thermometer and a reflux condenser. The flask was charged with unpurified 4-{[(2S)-2-hydroxy-3-(9-oxa-3,7-diazabicyclo[3.3.1]non-3-yl)propyl]-oxy}benzonitrile (73 g, from step (iii) above), dichloromethane (0.7 L) and tert-butyl 2-bromoethylcarbamate (see Preparation B(I)(i) above, 74 g, 0.330 mol). Triethylamine (52 mL, 0.359 mol) was then added. The clear solution was refluxed for 16 hours and then cooled to room temperature. The reaction mixture was transferred to a separating funnel and washed sequentially with water (100 mL) and brine (100 mL). The organic layer was dried over magnesium sulfate, filtered and concentrated under vacuum. The resulting yellow viscous oil was purified by chromatography on silica gel, eluting first with 9:1 dichloromethane/methanol, then with 9:1:0.02 dichloromethane/methanol/28% aqueous ammonium hydroxide to afford an off-white foamy solid (40 g). The solid was dissolved in dichloromethane (200 mL) and washed sequentially with 20% aqueous sodium hydroxide (100 mL) and water (100 mL). The organic layer was dried over magnesium sulfate and concentrated under vacuum to afford title compound as an off-white solid (35.4 g, 67% yield in three steps).

Method II iso-Propanol (5 mL) and water (0.5 mL) were added to [2-(9-oxa-3,7-diazabicyclo[3.3.1]non-3-yl)ethyl] carbamic acid tert-butyl ester (see Preparation B(II)(ii), Method I above; 0.43 g, 1.6 mmol) and 4-[(2S)-oxiranylmethoxy]benzonitrile (0.280 g, 1.6 mmol, see step (i) above) was added. The mixture was heated at 66° C. for 19 hours (reaction was complete in 2 hours). The solvent was evaporated to dryness under reduced pressure to give the title compound as an off-white solid (0.71 g, 100%).

$^1$H-NMR (300 MHz, CDCl$_3$) δ 1.41 (9H, s), 2.3–2.75 (6H, m), 2.75–3.0 (5H, m), 3.1–3.38 (3H, m), 3.88 (2H, s), 3.95–4.19 (3H, m), 5.85 (1H, bs), 6.99 (2H, d), 7.6 (2H, d). $^1$H-NMR (300 MHz, DMSO-D$_6$) δ 1.35 (9H, s), 2.12–2.59 (7H, m), 2.63–2.78 (1H, m), 2.78–2.9 (4H, m), 3.2 (2H, q), 3.78 (2H, m), 4–4.1 (2H, m), 4.12–4.19 (1H, m), 5.3 (1H, bs), 6.61 (1H, t), 7.15 (2H, d), 7.76 (2H, d). MS: m/z=447 (MH$^+$).

Method III: The solution of [2-(9-oxa-3,7-diazabicyclo[3.3.1]non-3-yl)ethyl]carbamic acid tert-butyl ester generated in Preparation B(II)(ii), Method 2 above (assumed 154.85 g, 1.0 mol eq, 1.0 wt/vol) in a mixture of toluene (approx 640 mL), ethanol (approx 1280 mL) and water (approx 130 mL), was basified with aqueous sodium hydroxide (10 M, 51 mL, 0.9 mol eq.). Solid 4-[(2S)-oxiranylmethoxy]benzonitrile (99.80 g, 1.0 mol eq.; see step (i) above) was added and the combined mixture was heated to 70° C. for four hours. The reaction was monitored by TLC using a silica plate with mobile phase X:DCM 1:1 v/v (in which X is chloroform:methanol:concentrated ammonia 80:18:2 v/v). Visualisation was by UV light (254 nm) and by staining with aqueous potassium permanganate. This showed the complete disappearance of starting material and the appearance of the title compound. The reaction mixture was cooled, filtered through kieselguhr and washed through with ethanol (620 mL, 4.0 vol). This gave a solution of title compound (assumed 254.38 g, 100% th, 2.4 L, 1.0 wt/vol for reaction work up). This solution was charged into a flask that was set up for reduced pressure distillation. A graduation line was marked onto the side of this flask. Solvent (1250 mL) was removed at between 50° C. and 35° C., 320 mbar and 100 mbar. Then 4-methylpentan-2-ol (1500 mL) was added in order to reach the graduated line. Solvent (1250 mL) was removed at between 35° C. and 80° C., 220 mbar and 40 mbar. More 4-methylpentan-2-ol (1500 mL) was added in order to reach the graduated line. Solvent (1250 mL) was removed at between 62° C. and 76° C., 100 mbar and 90 mbar. The combined mixture was cooled to less than 25° C. and aqueous sodium hydroxide (2 M, 1.27 L, 5.0 vol) was added. The layers were separated and the organic layer was filtered through kieselguhr to give a clear solution (1.2 L). This solution was charged into a clean flask, which was set up for reduced pressure distillation. Solvent (450 mL) was removed at between 52° C. and 55° C., 90 mbar and 35 mbar. Theoretically, the product was now left in 2 volumes of 4-methylpentan-2-ol. Di-n-butyl ether (1.27 L, 5 vol) was added and the solution was allowed to cool slowly to room temperature, which caused a precipitate to form. The mixture was cooled from room temperature to approximately 10° C. The product was collected by filtration and was washed with a pre-mixed solution of di-n-butyl ether (320 mL, 1.25 vol) and 4-methylpentan-2-ol (130 mL, 0.50 vol). The damp product was dried in vacuo at 55° C. to constant weight to give the title compound as a white solid (193.6 g, 76%).

m.p. 99–101° C. $^1$H-NMR (300 MHz, CDCl$_3$) δ 1.41 (9H, s), 2.3–2.75 (6H, m), 2.75–3.0 (5H, m), 3.1–3.38(3H, m), 3.88 (2H, s), 3.95–4.19 (3H, m), 5.85 (1H, bs), 6.99 (2H, d), 7.6 (2H, d).

EXAMPLE 1

Crystallisation of Compound A
(Method (I); B Form)

Compound A (246.58 g; prepared analogously to procedures described in Preparation A above, though, on this occasion material was re-combined with mother liquors, base washed with NaOH, and then evaporated to give solid) was slurried in ethyl acetate (500 mL) and then heated to dissolve the solid. A clear solution was obtained. Ethyl acetate (80 mL) was removed by distillation in order to dry azeotropically the compound (leaving 1.7 volumes of ethyl acetate). The solution was then transferred hot to a pre-warmed 1 L flange flask (temperature at transfer was 68° C.). The solution was then left to cool naturally (heat source completely removed) under nitrogen, with overhead air stirring. After 40 minutes cooling, crystallisation began (internal temperature was 38° C.). The solution temperature was between 38–40° C. for the next 1.5 hours. The solution was then cooled to 20° C. with a water/ice bath and left for 1 hour. The product was filtered, washed with cold (0° C.) ethyl acetate (330 mL), and then dried overnight in vacuo at 40° C. to give 126.83 g (yield 51%, assuming input material was dry).

The crystals were analyzed by XRPD and the results are tabulated below (Table 1) and are shown in FIG. 1.

TABLE 1

| d value (Å) | Intensity (%) |
|---|---|
| 11.0 | 81 |
| 8.3 | 2 |
| 7.8 | 5 |
| 7.0 | 24 |
| 6.7 | 2 |
| 5.9 | 3 |
| 5.7 | 16 |
| 5.5 | 4 |
| 5.4 | 8 |
| 5.1 | 44 |
| 4.94 | 7 |
| 4.71 | 4 |
| 4.62 | 5 |
| 4.54 | 33 |
| 4.44 | 100 |
| 4.34 | 12 |
| 4.20 | 7 |
| 4.12 | 2 |
| 3.92 | 5 |
| 3.65 | 15 |
| 3.51 | 9 |
| 3.47 | 2 |
| 3.41 | 4 |
| 3.34 | 5 |
| 3.31 | 0.8 |
| 3.26 | 2 |
| 3.04 | 2 |
| 2.89 | 4 |
| 2.82 | 3 |
| 2.77 | 2 |
| 2.70 | 2 |
| 2.58 | 2 |
| 2.44 | 1 |
| 2.34 | 4 |
| 2.18 | 3 |
| 2.06 | 3 |

A unit cell was determined from single crystal X-ray data. It was orthorhombic, with space group P2$_1$2$_1$2$_1$ and the following dimensions: a=9.096 Å, b=11.077 Å, c=22.136 Å, α=β=γ=90°, and V=2230.3 Å$^3$.

DSC showed two endotherms with extrapolated onset temperatures of ca. 121° C. and 126° C. TGA showed a decrease in mass of ca. 0.1% (w/w) between 110 and 130° C.

EXAMPLE 2

Crystallisation of Compound A
(Method (II); A Form)

Ethyl acetate (250 mL) was added to Compound A (188.10 g, prepared analogously to the processes described in Preparation A above) and the mixture was heated. The hot solution obtained was filtered (there was no residue). During filtration, some solid precipitated from the solution being filtered. This was re-dissolved in ethyl acetate (50 mL) and filtered. The combined filtrates were concentrated by removing ethyl acetate (120 mL). The remaining solution was allowed to cool to room temperature (crystallisation started at 40° C.). The slurry was then cooled to 10° C. for 1 hour.

The solid product was filtered, washed with cold ethyl acetate (100 mL) and then dried in vacuo at 40° C. to give 126.7 g (68 %).

Figure 2:
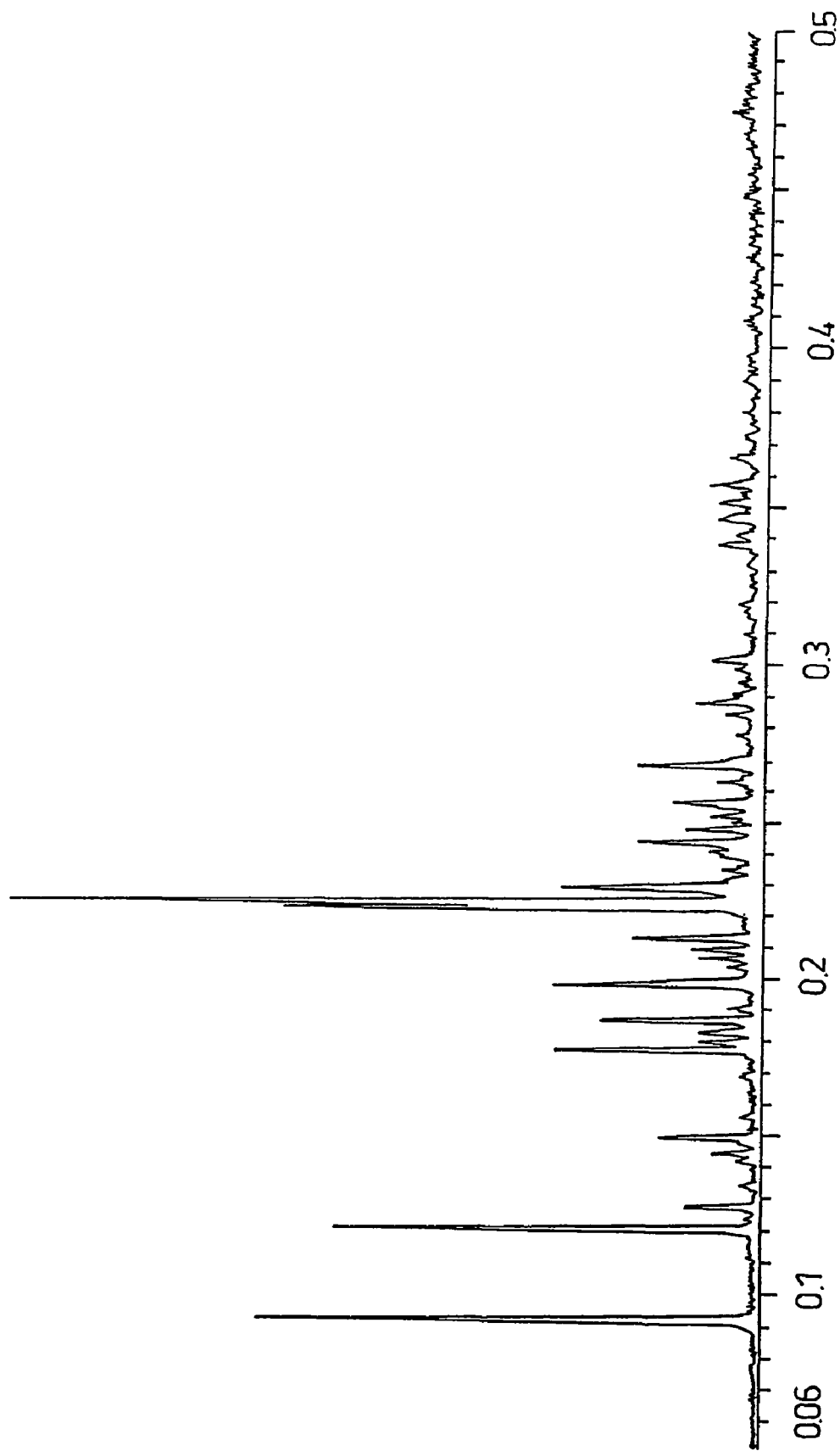
FIG. 2 shows an X-ray powder diffractogram for the crystalline form of Compound A (A Form), obtained by way of Example 2.

The crystals were analyzed by XRPD and the results are tabulated below (Table 2) and are shown in FIG. 2.

TABLE 2

| d value (Å) | Intensity (%) |
|---|---|
| 10.9 | 65 |
| 8.3 | 54 |
| 7.8 | 9 |
| 7.5 | 3 |
| 7.0 | 3 |
| 6.9 | 6 |
| 6.8 | 2 |
| 6.7 | 12 |
| 6.4 | 2 |
| 5.9 | 2 |
| 5.6 (5.64) | 26 |
| 5.6 (5.56) | 8 |
| 5.5 | 7 |
| 5.4 | 20 |
| 5.3 | 3 |
| 5.1 | 27 |
| 5.0 | 14 |
| 4.90 | 3 |
| 4.84 | 8 |
| 4.78 | 8 |
| 4.70 | 16 |
| 4.49 | 64 |
| 4.45 | 100 |
| 4.36 | 26 |
| 4.25 | 4 |
| 4.15 | 6 |
| 4.10 | 15 |
| 4.03 | 9 |
| 3.97 | 6 |
| 3.90 | 11 |
| 3.80 | 5 |
| 3.73 | 15 |
| 3.60 | 2 |
| 3.52 | 4 |
| 3.47 | 8 |
| 3.44 | 3 |
| 3.39 | 2 |
| 3.35 | 2 |
| 3.31 | 6 |
| 3.23 | 1 |
| 3.13 | 2 |
| 3.01 | 1 |
| 2.95 | 5 |
| 2.93 | 3 |
| 2.89 | 5 |
| 2.85 | 5 |
| 2.80 | 6 |
| 2.74 | 3 |
| 2.69 | 2 |
| 2.63 | 2 |
| 2.56 | 2 |

DSC showed an endotherm with an extrapolated onset temperature of ca. 125° C. TGA showed a decrease in mass of ca. 0.1% (w/w) between 120 and 130° C.

EXAMPLE 3

Crystallisation of Compound A
(Method (I); C Form)

Compound A, benzenesulphonic acid salt monohydrate (4.5 kg, prepared analogously to the processes described in Preparation A above) was added to dichloromethane (89.7 kg). Aqueous sodium hydroxide (1 M, 46.9 kg) was added and the reaction mixture was stirred for 45 minutes. The final temperature of the contents was 16.9° C. The two phases were left for 68 minutes to separate and the aqueous layer (48.8 kg) was discarded. The organic layer was filtered into a clean vessel and filtered. Ethanol (72 kg) was added. Solvent (101.1 kg) was distilled off (3 hours 20 min.). The final temperature of the contents was 76.0° C. Ethanol (25.4 kg) was added and a further 11.6 kg of solvent was distilled off (1 hour 30 min.), the final temperature of the contents was 79.3° C. The solution was cooled to −17° C. overnight but no crystallisation was observed. A further 32.7 kg of solvent was distilled off and the reaction mixture was cooled to 15° C. overnight, during which time the product crystallised. The reaction mixture was cooled to 0° C. and stirred for 30 minutes. The product was filtered off and washed with ethanol (7.3 kg) to give a damp solid (2.7 kg). The product was dried at room temperature for 2 hours 16 min (33 mm Hg), then at 40–45° C. for 15 hours 24 minutes (29 mm Hg) to leave 2.18 kg of product, which was 99.76% pure by area, 0.3% w/w ethanol.

Figure 3:
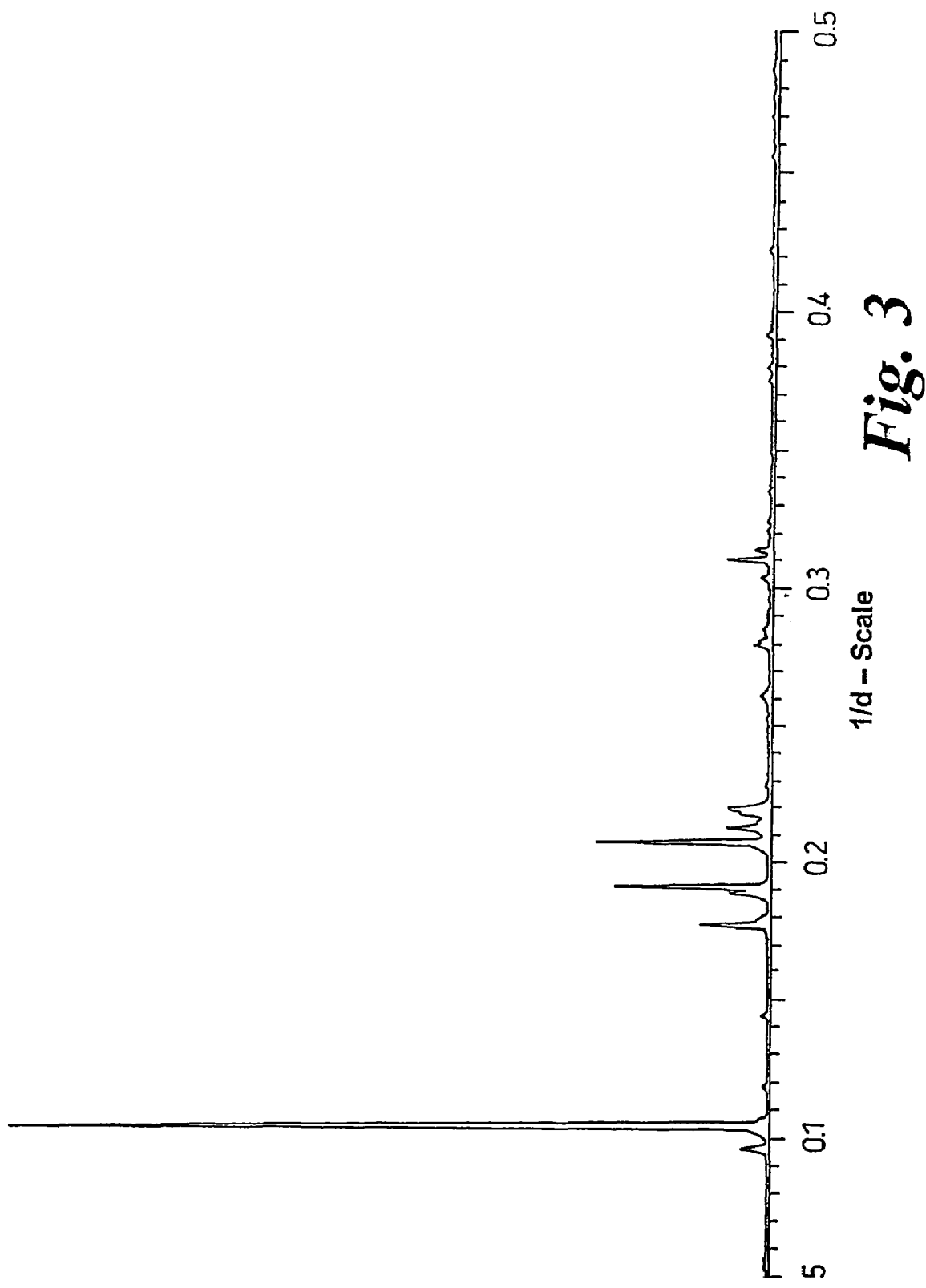
FIG. 3 shows an X-ray powder diffractogram for the crystalline form of Compound A (C Form), obtained by way of Example 3.

The crystals were analyzed by XRPD and the results are tabulated below (Table 3) and are shown in FIG. 3.

TABLE 3

| d value (Å) | Intensity (%) |
|---|---|
| 10.4 | 4 |
| 9.6 | 100 |
| 8.5 | 0.6 |
| 7.0 | 0.9 |
| 5.7 | 9 |
| 5.3 | 6 |
| 5.2 | 20 |
| 4.83 | 22 |
| 4.71 | 6 |
| 4.55 | 6 |
| 4.39 | 0.6 |
| 3.96 | 0.5 |
| 3.83 | 1 |
| 3.58 | 2 |
| 3.50 | 1 |
| 3.43 | 0.4 |
| 3.29 | 1 |
| 3.22 | 6 |
| 3.19 | 2 |
| 3.12 | 0.3 |
| 3.08 | 0.5 |
| 2.99 | 0.3 |
| 2.86 | 0.3 |
| 2.66 | 0.6 |
| 2.63 | 0.8 |
| 2.55 | 0.9 |
| 2.37 | 0.7 |
| 2.31 | 0.4 |
| 2.19 | 0.6 |
| 2.13 | 0.4 |
| 2.10 | 0.3 |

A unit cell was determined from single crystal X-ray data. It was orthorhombic, with space group C2cb and the following dimensions: a=10.685 Å, b=19.391 Å, c=21.07 Å, $\alpha=\beta=\gamma=90°$, and V=4365.8 Å$^3$.

DSC showed an endotherm with an extrapolated onset temperature of ca. 122° C. TGA showed a decrease in mass of ca. 0.3% (w/w) between 25 and 140° C.

EXAMPLE 4

Crystallisation of Compound A, benzenesulphonic acid salt monohydrate 1.88 g (4.9 mmol) of Compound A (prepared analogously to procedures described in Preparation A above) was dissolved in 23 mL ethyl acetate. 0.807 g (5.1 mmol) of benzenesulphonic acid was dissolved in 4.5 mL methanol. The benzenesulphonic acid solution was added to the stirred solution of Compound A. The benzenesulphonate salt precipitated after ca. 10 minutes. The precipitate was kept at 4° C. overnight. The crystals were filtered off, washed with ethyl acetate and dried in vacuo overnight. Yield 1.6 g (60%). The product was recrystallised from EtOH:H$_2$O (1:1)

Figure 4:
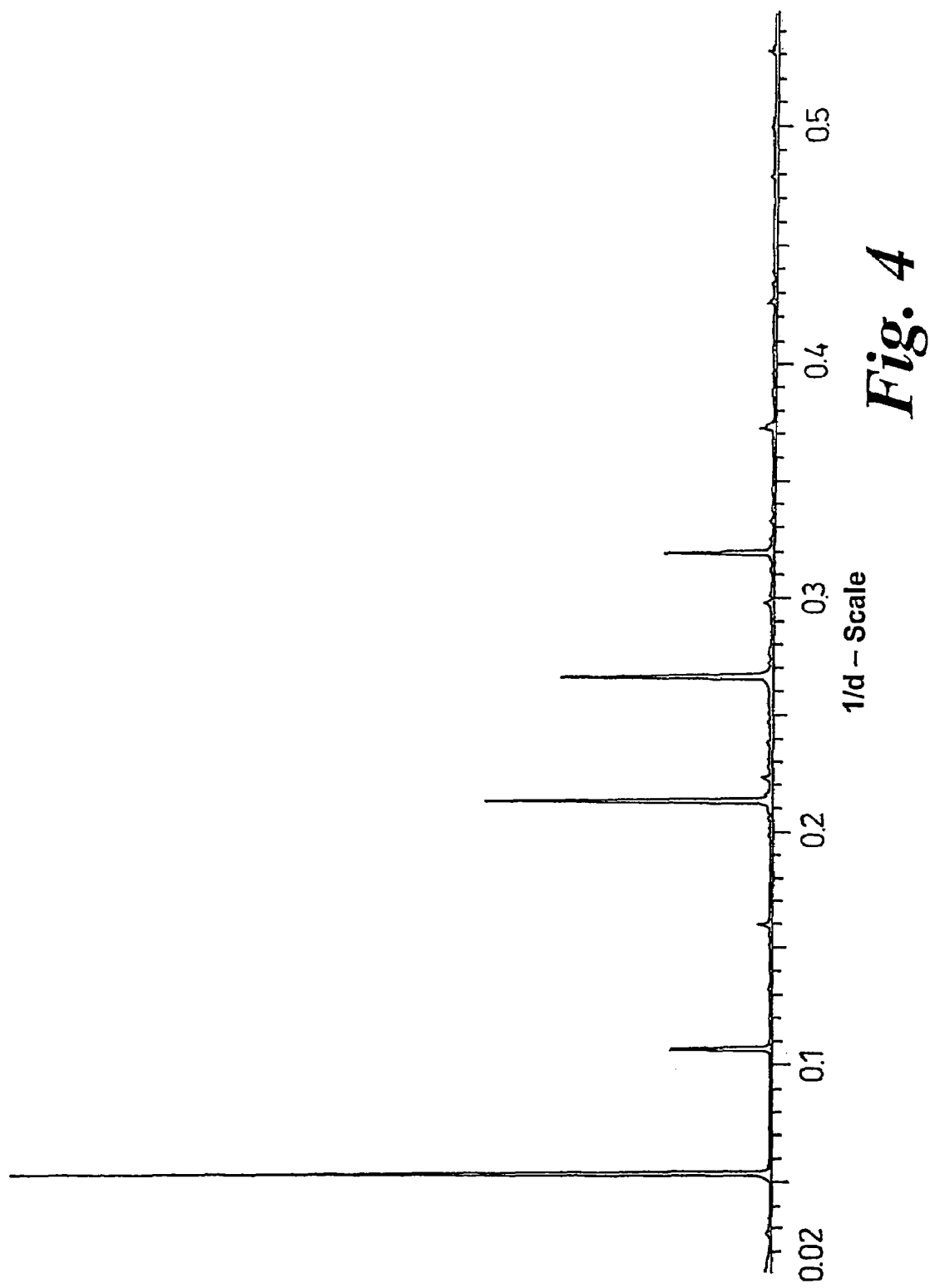
FIG. 4 shows an X-ray powder diffractogram for the crystalline form of Compound A, benzenesulphonic acid salt, obtained by way of Example 4.

The crystals were analyzed by XRPD and the results are tabulated below (Table 4) and are shown in FIG. 4.

TABLE 4

| d value (Å) | Intensity (%) |
| --- | --- |
| 18.7 | 100 |
| 9.4 | 13 |
| 7.5 | 0.3 |
| 6.6 | 0.2 |
| 6.4 | 0.2 |
| 6.3 | 2 |
| 5.1 | 0.3 |
| 4.85 | 0.3 |
| 4.77 | 0.3 |
| 4.69 | 37 |
| 4.63 | 0.7 |
| 4.48 | 1 |
| 4.40 | 0.2 |
| 4.19 | 0.6 |
| 4.13 | 0.2 |
| 4.05 | 0.3 |
| 3.92 | 0.2 |
| 3.89 | 0.3 |
| 3.76 | 28 |
| 3.61 | 0.2 |
| 3.35 | 1 |
| 3.31 | 0.3 |
| 3.21 | 0.2 |
| 3.13 | 14 |
| 3.07 | 0.2 |
| 3.00 | 0.4 |
| 2.68 | 2 |
| 2.35 | 1 |
| 2.31 | 0.3 |
| 2.09 | 0.6 |
| 2.00 | 0.4 |
| 1.88 | 1 |

A unit cell was determined from single crystal X-ray data. It was monoclinic, with space group P2$_1$/c and the following dimensions: a=18.833 Å, b=9.293 Å, c=16.271 Å, α=90°, β=94.94°, γ=90°, and V=2837.1 Å$^3$.

The product is a monohydrate without a well defined melting point. DSC showed an endotherm with an extrapolated onset temperature in the range ca. 85–110° C. TGA showed a decrease in mass of ca. 3% (w/w) between 60 and 160° C.

EXAMPLE 5

Crystallisation of Compound A, para-toluenesulphonic acid salt (A and B Forms)

Compound A (1.14 g, 2.96 mmol, prepared analogously to procedures described in Preparation A above (e.g. prior to addition of benzenesulphonic acid in the procedure described therein for formation of Compound A, benzenesulphonic acid salt)) was dissolved in ethyl acetate (20 mL). A solution of para-toluenesulphonic acid (PTSA) (0.57 g, 2.99 mmol) in methanol (0.3 mL) was added dropwise. The PTSA washing in 0.1 mL methanol, and an additional 5 mL of ethyl acetate were added. A white slurry formed in few minutes. This was stirred for 1 h. The solid was filtered off and washed with 5 mL of ethyl acetate. Yield 1.4 g (84.8%). The solid (1.40 g) toluenesulphonic acid salt was mixed with 15 mL of ethyl acetate and heated to reflux. To the slurry was added 0.85 mL methanol. Within a few seconds, all of the solid had gone into solution. This was allowed to cool and, within a few minutes, crystallization was observed. Soon, this became a set solid. To this was added more ethyl acetate (10 mL) and methanol (0.15 mL). The thick slurry was then stirred at 0° C. for 30 minutes. The solids were filtered off and washed with ethyl acetate (5 mL). These were allowed to dry on suction. Yield 1.10 g (66.6%). A portion of this (500 mg) was dried at 50° C. under reduced pressure, giving 0.440 g.

Figure 5B:
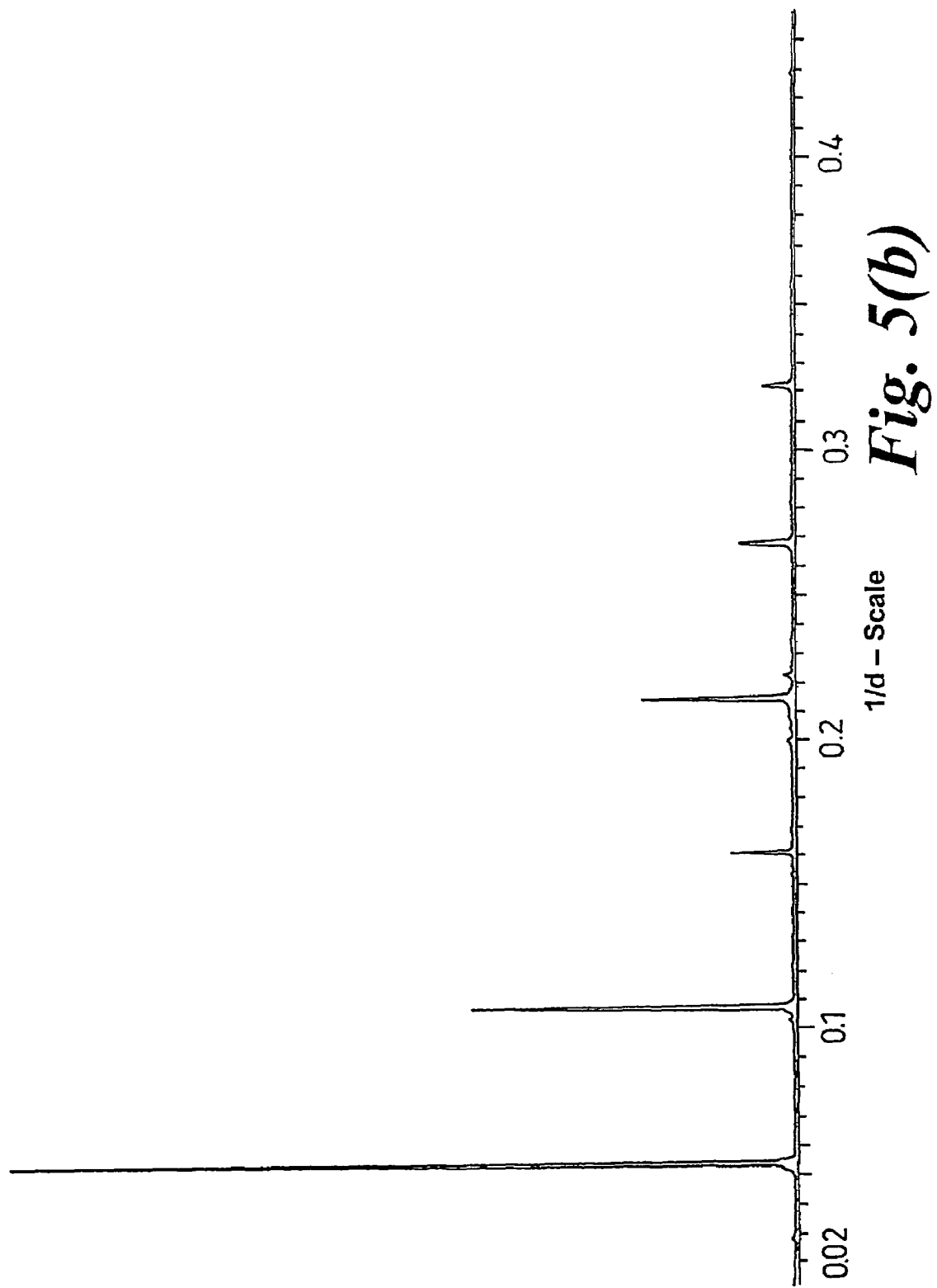
FIG. 5(*a*) shows an X-ray powder diffractogram for the crystalline form of Compound A, para-toluenesulphonic acid salt (A Form), obtained by way of Example 5.

A portion of toluenesulphonic acid salt was recrystallised from acetone. The crystals (A Form) were analyzed by XRPD and the results are tabulated below (Table 5(a)) and are shown in FIG. 5(*a*). A portion of toluenesulphonic acid salt was suspended in a phosphate buffer (ionic strength 0.1 M at pH 3), followed by decantation. The crystals (B Form) were analyzed by XRPD and the results are tabulated below (Table 5(b)) and are shown in FIG. 5(*b*).

TABLE 5(a)

| d value (Å) | Intensity (%) |
| --- | --- |
| 19.9 | 100 |
| 10.0 | 30 |
| 8.7 | 0.5 |
| 7.6 | 1 |
| 7.0 | 0.9 |
| 6.6 | 0.7 |
| 6.4 | 1 |
| 6.0 | 4 |
| 5.7 | 1 |
| 5.5 | 0.8 |
| 5.2 | 1 |
| 4.99 | 33 |
| 4.86 | 4 |
| 4.49 | 2 |
| 4.38 | 4 |
| 4.36 | 8 |
| 4.19 | 5 |
| 3.99 | 5 |
| 3.93 | 1 |
| 3.77 | 1 |
| 3.59 | 2 |
| 3.40 | 1 |
| 3.33 | 5 |
| 3.29 | 1 |
| 3.19 | 0.7 |
| 3.08 | 1 |
| 2.86 | 0.7 |
| 2.22 | 0.7 |
| 2.11 | 0.6 |
| 2.09 | 0.7 |
| 2.00 | 1 |

For the A form, DSC showed an endotherm with an extrapolated onset temperature of ca. 145° C. TGA showed a decrease in mass of ca. 3.3% (w/w) between 20 and 120° C.

TABLE 5(b)

| d value (Å) | Intensity (%) |
| --- | --- |
| 18.6 | 100 |
| 9.7 | 0.6 |
| 9.3 | 43 |
| 7.6 | 0.4 |
| 6.2 | 8 |
| 5.0 | 0.9 |
| 4.66 | 20 |

TABLE 5(b)-continued

| d value (Å) | Intensity (%) |
|---|---|
| 4.49 | 2 |
| 3.73 | 8 |
| 3.11 | 4 |
| 2.33 | 0.6 |

For the B form, DSC showed an endotherm with an extrapolated onset temperature of ca. 153° C. TGA showed a decrease in mass of ca. 4.4% (w/w) between 25 and 120° C.

EXAMPLE 6

Crystallisation of Compound A, 1-hydroxy-2-naphthoic acid salt

To Compound A (0.60 g, 1.56 mmol, prepared analogously to procedures described in Preparation A above (e.g. prior to addition of benzenesulphonic acid in the procedure described therein for formation of Compound A, benzenesulphonic acid salt)) in ethyl acetate (10 mL) was added 1-hydroxy-2-naphthoic acid (0.323 g, 1.7 mmol) in methanol (1 mL). A solution was not formed. The mixture was stirred at room temperature for 30 minutes. No crystallization was noticed. The solution was then cooled for 30 minutes. Small amounts of crystals were observed. The solvents were evaporated to dryness, the solids were taken up in ethyl acetate (5 mL) and heated to reflux. To the partial solution was added methanol (0.2 mL). The resultant slurry was cooled with ice/water, filtered and washed with ethyl acetate (2 mL). The solid was then dried in an oven at 50° C. under reduced pressure for 24 h. Yield 0.510 g (57%).

Figure 6:
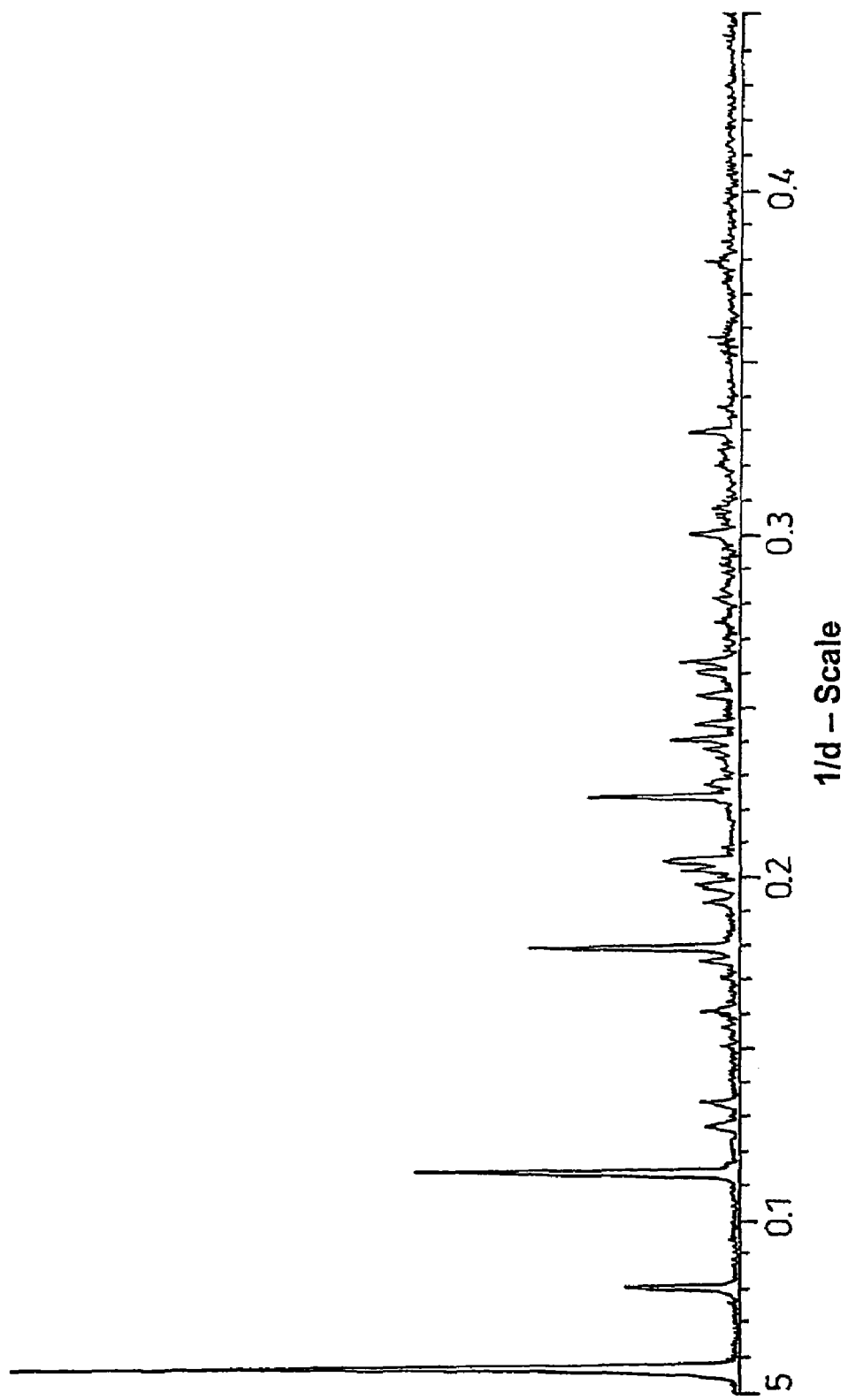
FIG. 6 shows an X-ray powder diffractogram for the crystalline form of Compound A, 1-hydroxy-2-naphthoic acid salt, obtained by way of Example 6.

The crystals were analyzed by XRPD and the results are tabulated below (Table 6) and are shown in FIG. 6.

TABLE 6

| d value (Å) | Intensity (%) |
|---|---|
| 17.6 | 100 |
| 12.4 | 16 |
| 8.8 | 44 |
| 7.9 | 4 |
| 7.5 | 5 |
| 6.6 | 2 |
| 6.4 | 2 |
| 6.2 | 5 |
| 5.7 | 5 |
| 5.6 | 29 |
| 5.2 | 4 |
| 5.1 | 6 |
| 4.95 | 7 |
| 4.88 | 9 |
| 4.47 | 20 |
| 4.40 | 4 |
| 4.21 | 4 |
| 4.16 | 8 |
| 4.08 | 6 |
| 3.95 | 5 |
| 3.84 | 5 |
| 3.80 | 8 |
| 3.64 | 3 |
| 3.55 | 3 |
| 3.33 | 6 |
| 3.03 | 7 |
| 2.96 | 2 |
| 2.63 | 4 |

EXAMPLE 7

Crystallisation of Compound A, 1,5-naphthalenesulphonic acid salt

Compound A (0.490 g, 1.27 mmol, prepared analogously to procedures described in Preparation A above (e.g. prior to addition of benzenesulphonic acid in the procedure described therein for formation of Compound A, benzenesulphonic acid salt)) was dissolved in ethyl acetate (10 mL). A solution of 1,5-naphthalenesulphonic acid in methanol (0.5 mL) was added. In few minutes, white solid appeared. This was stirred at room temperature for 30 minutes and then cooled with ice/water. Some chunks of white solid where noticed in the slurry. The solids were filtered to give 0.34 g of white solid. This was taken up in methanol (50 mL) and water (100 mL) and heated to reflux, until an almost clear solution was obtained. The solution was allowed to attain room temperature, and was then cooled with ice/water for 30 minutes. The solids were filtered to give a white powder (0.150 g). The solid was dried in an oven at 50° C. under reduced pressure for 5 h.

$^1$H-NMR demonstrated a 1:2 ratio of acid to base.

Figure 7:
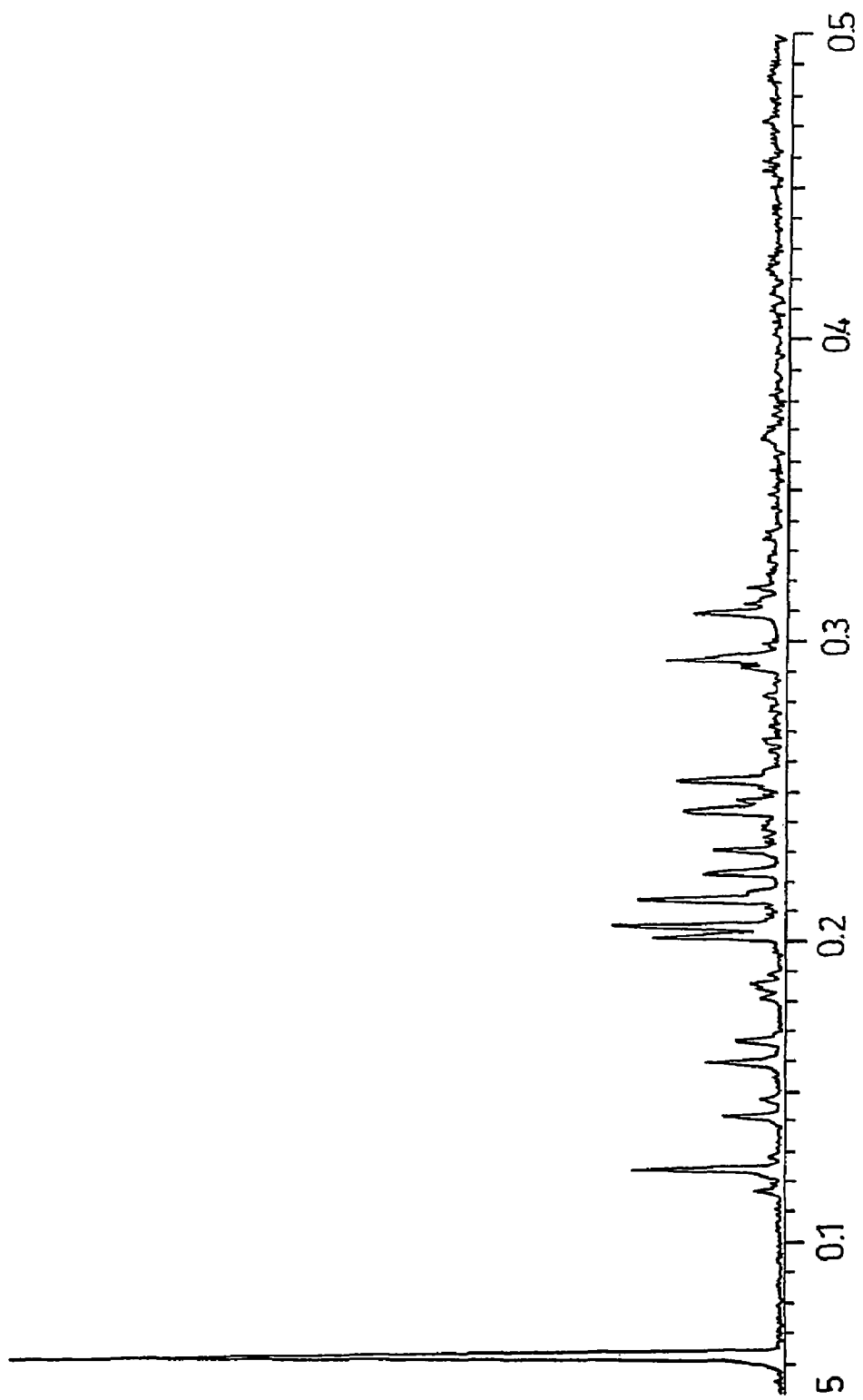
FIG. 7 shows an X-ray powder diffractogram for the crystalline form of Compound A, 1,5-naphthalenesulphonic acid salt, obtained by way of Example 7.

The crystals were analyzed by XRPD and the results are tabulated below (Table 7) and are shown in FIG. 7.

TABLE 7

| d value (Å) | Intensity (%) |
|---|---|
| 16.1 | 100 |
| 8.6 | 4 |
| 8.1 | 19 |
| 7.8 | 2 |
| 7.1 | 7 |
| 6.8 | 3 |
| 6.3 | 10 |
| 6.0 | 6 |
| 5.5 | 3 |
| 5.4 (5.43) | 3 |
| 5.4 (5.39) | 4 |
| 5.3 | 2 |
| 4.96 | 17 |
| 4.88 | 22 |
| 4.68 | 18 |
| 4.62 | 4 |
| 4.49 | 9 |
| 4.34 | 8 |
| 4.10 | 12 |
| 4.04 | 6 |
| 3.94 | 13 |
| 3.55 | 2 |
| 3.44 | 5 |
| 3.40 | 15 |
| 3.23 | 11 |
| 3.20 | 5 |
| 3.15 | 4 |
| 2.87 | 2 |
| 2.72 | 3 |
| 2.19 | 3 |
| 2.18 | 3 |

EXAMPLE 8

Crystallisation of Compound A, 2-mesitylenesulphonic acid salt

A solution of 2-mesitylenesulphonic acid (0.276 g) in methanol (0.3 mL) was added to a stirred solution of Compound A (0.45 g, prepared analogously to procedures described in Preparation A above (e.g. prior to addition of benzenesulphonic acid in the procedure described therein for formation of Compound A, benzenesulphonic acid salt)) in ethyl acetate (10 mL). Precipitation occurred immediately. The slurry was stirred at room temperature for 30 minutes and then cooled with ice/water. The product was filtered off and washed with ethyl acetate (3 mL) to give the title compound (0.60 g, 88%). The salt produced was dissolved in ethyl acetate (10 mL) and heated to reflux. Methanol (3 mL) was added to give a clear solution. The solution was allowed to cool to room temperature and then stirred at 0–5° C. for 1 hour. The slurry was filtered to give a colourless solid (0.370 g, 54% over two steps).

Figure 8:
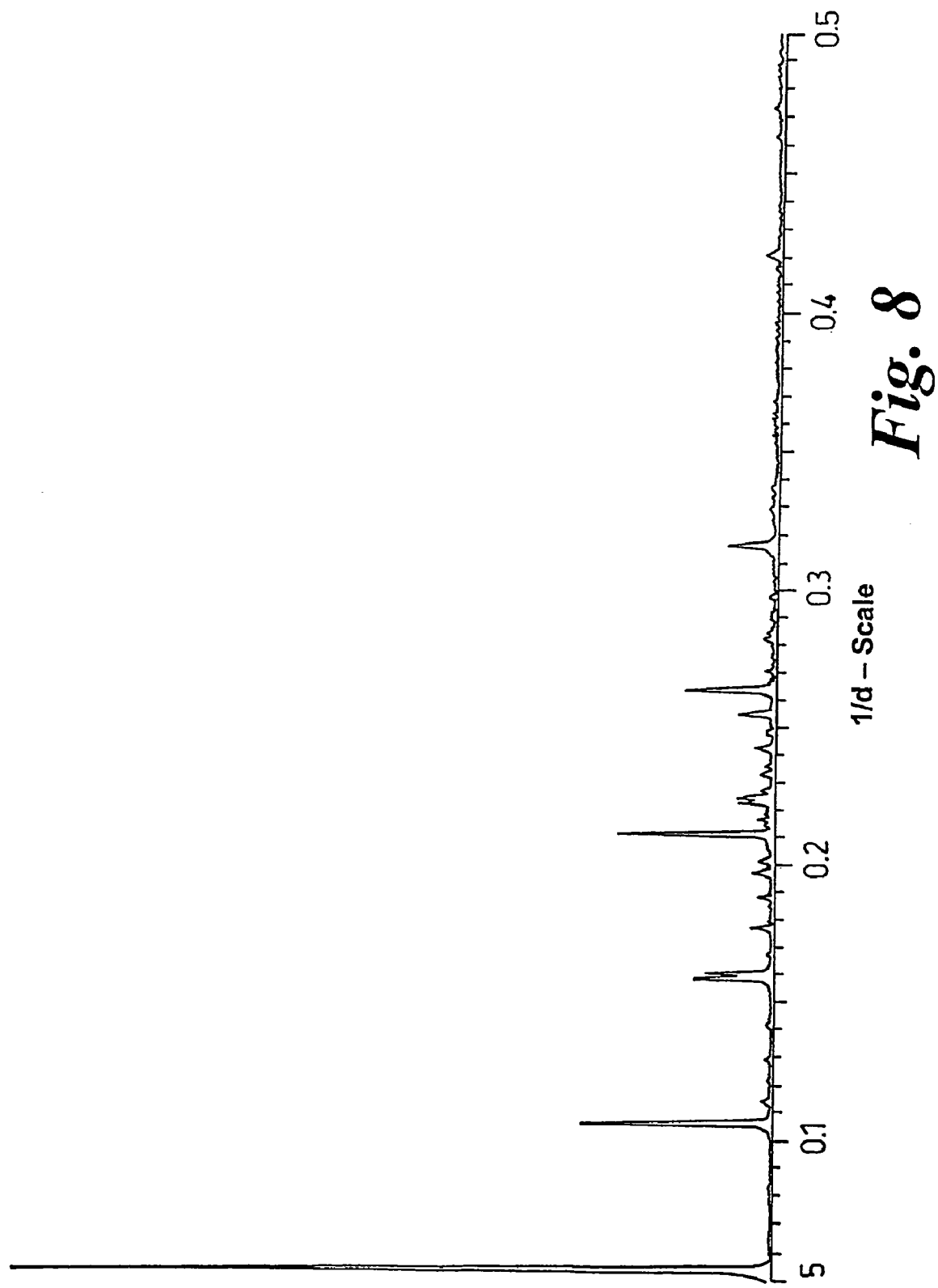
FIG. 8 shows an X-ray powder diffractogram for the crystalline form of Compound A, 2-mesitylenesulphonic acid salt, obtained by way of Example 8.

The crystals were analyzed by XRPD and the results are tabulated below (Table 8) and are shown in FIG. 8.

TABLE 8

| d value (Å) | Intensity (%) |
|---|---|
| 18.9 | 100 |
| 9.5 | 25 |
| 8.8 | 1 |
| 7.8 | 1 |
| 6.3 (6.33) | 10 |
| 6.3 (6.26) | 9 |
| 5.7 | 3 |
| 5.3 | 2 |
| 5.1 | 3 |
| 4.98 | 2 |
| 4.75 | 20 |
| 4.62 | 2 |
| 4.50 | 4 |
| 4.46 | 5 |
| 4.41 | 2 |
| 4.29 | 1 |
| 4.24 | 1 |
| 4.13 | 2 |
| 3.92 | 5 |
| 3.80 | 12 |
| 3.69 | 1 |
| 3.54 | 2 |
| 3.36 | 1 |
| 3.17 | 6 |
| 3.04 | 1 |
| 2.38 | 2 |
| 2.11 | 1 |

EXAMPLE 9

Crystallisation of Compound D

Method I: Compound D (prepared analogously to the procedures described hereinbefore) was first purified by column chromatography on silica gel using 9:1:0.05 dichloromethane/methanol/28% aqueous ammonia as eluent. The resultant light yellow powder (203 g) was dissolved in dichloromethane (400 mL) and then the yellow solution was diluted with n-heptane (2 L) until the mixture became turbid. The mixture was stirred vigorously at room temperature and seeded with crystals of Compound D (prepared by slow evaporation of solvent from a small portion of a solution of title compound, prepared in analogous fashion to this procedure). A great deal of product had precipitated after stirring for two hours. The resulting slurry was filtered and then dried under vacuum at 40° C. to afford 179 g of title compound as an off-white powder. A second portion (44 g) of column purified material gave an additional 25 g of title compound after similar recrystallization.

Method II: A mixture of Compound D (prepared analogously to the procedures described hereinbefore (see especially Preparation D(iv), Method III above); 14.29 g), iso-propanol (28 mL) and di-iso-propyl ether (140 mL) was heated to 80° C. The solution was filtered hot to clarify it and then reheated to 80° C. The solution was then allowed to cool to room temperature whereupon a precipitate started to form. After stirring for two hours the precipitate was collected by filtration, washed with iso-propanol:di-iso-propyl ether (1:6, 70 mL) and then sucked dry on the filter. The damp product was dried in vacuo at 70° C. overnight to give the title compound as a white solid (10.1 g, 70%).

$^1$H-NMR (300 MHz, CDCl$_3$) δ 1.41 (9H, s), 2.3–2.75 (6H, m), 2.75–3.0 (5H, m), 3.1–3.38(3H, m), 3.88 (2H, s), 3.95–4.19 (3H, m), 5.85 (1H, bs), 6.99 (2H, d), 7.6 (2H, d)

Method III: Compound D (prepared analogously to the procedures described hereinbefore; 1.0 g) was dissolved in hot methyl iso-butyl ketone (10 mL). iso-Hexane (30 mL) was added and the solution decanted, from a small amount of undissolved material, into a clean flask. The solution was cooled overnight in a fridge which caused a granular precipitate to form. The solution was allowed to warm to room temperature and then the solid collected by filtration. The solid was sucked dry on the filter then dried in vacuo at 40° C. to give an off-white solid (0.73 g).

Method IV: Compound D (prepared analogously to the procedures described hereinbefore; 1.0 g) was dissolved in hot iso-propyl acetate (10 mL). iso-Octane (20 mL) was added and the solution decanted, from a small amount of undissolved material, into a clean flask. The solution was cooled overnight in a fridge which caused a granular precipitate to form. The solution was allowed to warm to room temperature and then the solid collected by filtration. The solid was sucked dry on the filter then dried in vacuo at 40° C. to give an off-white solid (0.82 g).

Method V: Compound D (prepared analogously to the procedures described hereinbefore; 1.0 g) was dissolved in hot aqueous ethanol (50%, 20 mL). The solution was cooled over a weekend in a fridge, which caused needle-shaped crystals to form. The crystals were collected by filtration and sucked dry on the filter. Drying in vacuo at 40° C. gave a colourless solid (0.48 g).

Method VI: Compound D (prepared analogously to the procedures described hereinbefore; 100 mg) was dissolved in toluene (1 mL). iso-Octane (2 mL) was added and the cloudy solution was cooled over a weekend in a fridge which caused a fine granular precipitate to form. The solution was allowed to warm to room temperature and then the solid collected by filtration. The solid was sucked dry on the filter then dried in vacuo at 40° C. to give an off white solid (62 mg).

Figure 9:
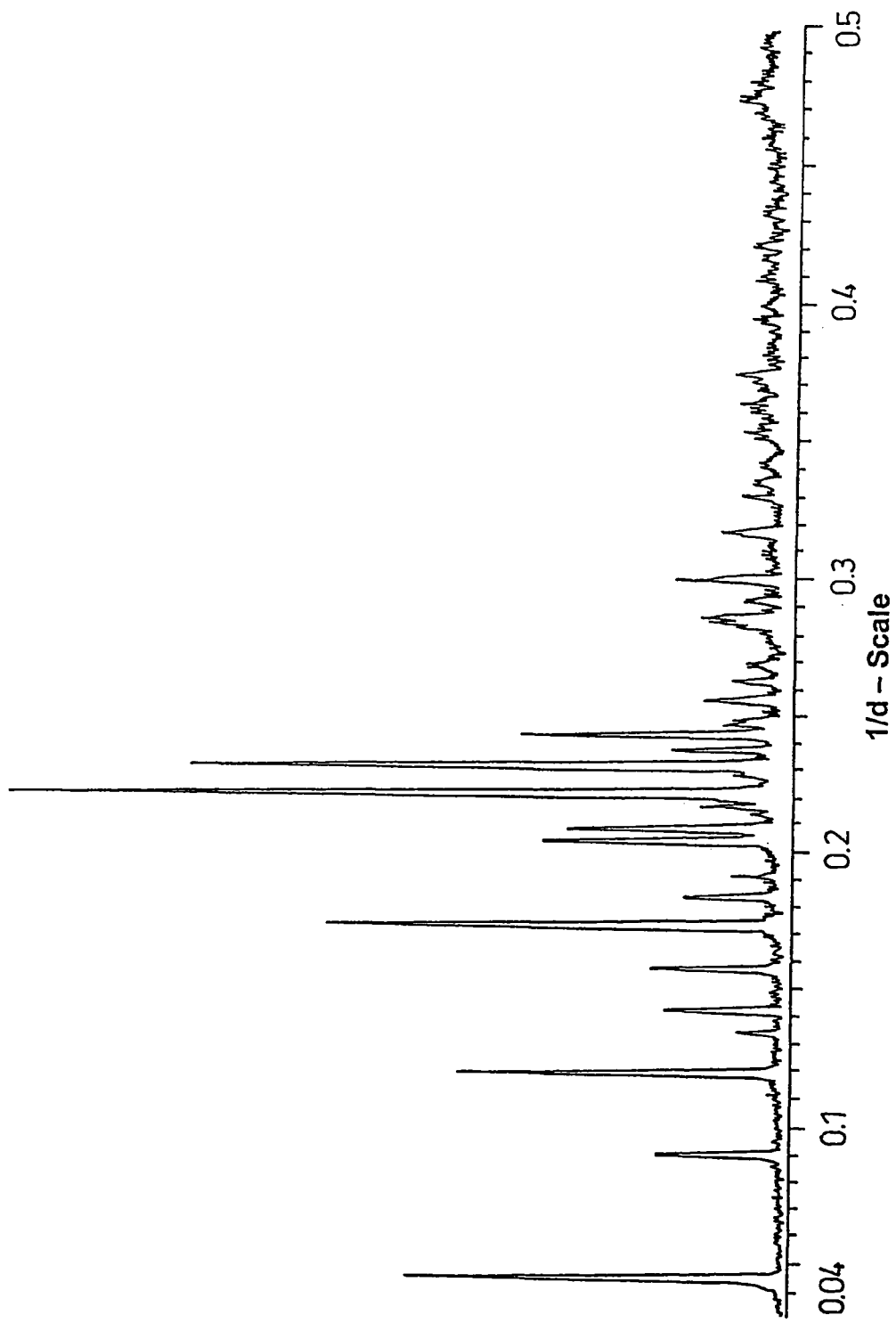
FIG. 9 shows an X-ray powder diffractogram for the crystalline form of Compound D, obtained by way of Example 9.

The crystals (from Methods I to VI) were analyzed by XRPD and the results are tabulated below (Table 9) and are shown in FIG. 9.

TABLE 9

| d value (Å) | Intensity (%) |
|---|---|
| 22.3 | 45 |
| 11.2 | 16 |
| 8.4 | 41 |
| 7.5 | 5 |
| 7.1 | 14 |
| 6.4 | 17 |
| 5.8 | 60 |
| 5.5 | 13 |
| 5.2 | 7 |

TABLE 9-continued

| d value (Å) | Intensity (%) |
|---|---|
| 4.91 | 31 |
| 4.81 | 28 |
| 4.69 | 4 |
| 4.62 | 10 |
| 4.52 | 100 |
| 4.32 | 77 |
| 4.22 | 14 |
| 4.12 | 35 |
| 4.06 | 7 |
| 3.91 | 9 |
| 3.81 | 7 |
| 3.72 | 4 |
| 3.53 | 5 |
| 3.50 | 9 |
| 3.42 | 5 |
| 3.34 | 12 |
| 3.15 | 8 |
| 3.03 | 5 |
| 2.98 | 3 |
| 2.92 | 3 |
| 2.83 | 4 |
| 2.77 | 4 |
| 2.75 | 5 |
| 2.67 | 6 |
| 2.37 | 3 |
| 2.11 | 5 |

A unit cell was determined from single crystal X-ray data. It was orthorhombic, with space group $P2_12_12_1$ and the following dimensions: a=5.870 Å, b=9.098 Å, c=45.101 Å, $\alpha=\beta=\gamma=90°$, and V=2408.6 Å$^3$.

DSC showed an endotherm with an extrapolated onset temperature of ca. 100–102° C. TGA showed a decrease in mass of ca. 0.4% (w/w) between 90 and 110° C.

EXAMPLE 10

Crystallisation of Compound D, methanesulphonic acid salt

Method I: Compound D (250 mg, prepared analogously to the processes described in Preparation D above) was dissolved in methanol (10 mL). Methanesulphonic acid (56 mg, 38 μL) was added to the solution. The methanol was removed under reduced pressure and the remaining gum was re-dissolved in the minimum amount of hot ethyl acetate possible. The solution was seeded with previously prepared crystals of salt (prepared by slow evaporation of solvent from a small portion of a solution of title compound, prepared in analogous fashion to this procedure) and were left in the fridge for several days to crystallise. The resulting crystals were collected by filtration and washed with a small amount of cold ethyl acetate (recovered 280 mg, 91%).

Method II: Compound D (4.00 g, prepared analogously to the processes described in Preparation D above) was dissolved in ethyl acetate (40 mL). A solution of methanesulfonic acid (0.87 g) in ethyl acetate (40 mL) was added. After 3 minutes the solution was seeded with previously prepared salt (14 mg, from Method I above) which caused the immediate formation of a precipitate. After 5 minutes the solid was collected by filtration and washed with ethyl acetate before being sucked dry on the filter. Drying in vacuo at 40° C. for 3.5 hours gave a white crystalline solid (4;71 g, 97%).

m.p. 170–2° C. (dec.)

Method III: Compound D, methanesulphonic acid salt (0.8 g; prepared according to the method described in Method II above) was heated in acetonitrile (8 mL, 10 vol). At 70° C., a solution had formed. This was allowed to cool to ambient temperature. The product was collected by filtration, and washed with a small volume of cold acetonitrile. This was initially dried in vacuo at 40° C. (melting point 169.4 to 69.9° C. (decomposed), residual solvent acetonitrile 0.08% w/w (GC)). This was further dried in vacuo at 80° C., residual solvent acetonitrile less than 0.02% w/w (GC). Purity 99.92% HPLC area.

Method IV: A mixture of Compound D, methanesulphonic acid salt (2.0 g, 1.0 mol eq., prepared according to the method described in Method II above) and acetonitrile (20 mL, 10 rel vol.) was heated to 80° C. At this temperature a solution had formed. The solution was allowed to cool to 25° C.±5° C. and then cooled further to 5° C.±5° C. The product was collected by filtration and washed with cold acetonitrile (4 mL, 2 rel vol.). The damp solid was dried in vacuo at 80° C. This gave the title compound (0.15 g, 7.5%) as an off-white solid. 99.97% HPLC area. Residual solvent acetonitrile less than 0.02% w/w (GC).

Method V: A mixture of Compound D, methanesulphonic acid salt (10.0 g, 1.0 mol eq.; prepared analogously to the method described in Method II above, except that, in this case, butyl acetate cf. ethyl acetate was used as solvent) and pentan-2-ol (100 mL, 10 rel vol.) was heated to 85° C. to give a solution. The solution was allowed to cool to 25° C.±5° C. and then cooled further to 5° C.±5° C. The product was collected by filtration and washed with cold pentan-2-ol (20 mL, 2 rel vol.). The damp solid was dried in vacuo at 40° C. for twenty hours. This gave the title compound (6.72 g, 67.2%) as an off-white solid. 99.47% HPLC area.

Method VI: A mixture of Compound D, methanesulphonic acid salt (3.0 g, 1.0 mol eq.; prepared according to the method described in Method V above) and 3-methylbutan-1-ol (15 mL, 5 rel vol.) was heated to 90° C. to give a solution. The solution was allowed to cool to 25° C.±5° C. and then further cooled to 5° C.±5° C. The product was collected by filtration and washed with cold 3-methylbutan-1-ol (6 mL, 2 rel vol.). The damp solid was dried in vacuo at 40° C. This gave the title compound as an off-white solid (2.43 g, 81%).

Method VII: A mixture of Compound D, methanesulphonic acid salt (2.0 g, 1.0 mol eq.; prepared according to the method described in Method V above) and hexan-1-ol (15 mL, 5 rel vol.) was heated to 80° C. to give a solution. The mixture was allowed to cool to. 25° C.±5° C. and then further cooled to 5° C.±5° C. The product was collected by filtration and washed with cold hexan-1-ol (6 mL, 2 rel vol.). The damp solid was dried in vacuo at 40° C. This gave the title compound as an off white solid (2.43 g, 81%).

Figure 10:
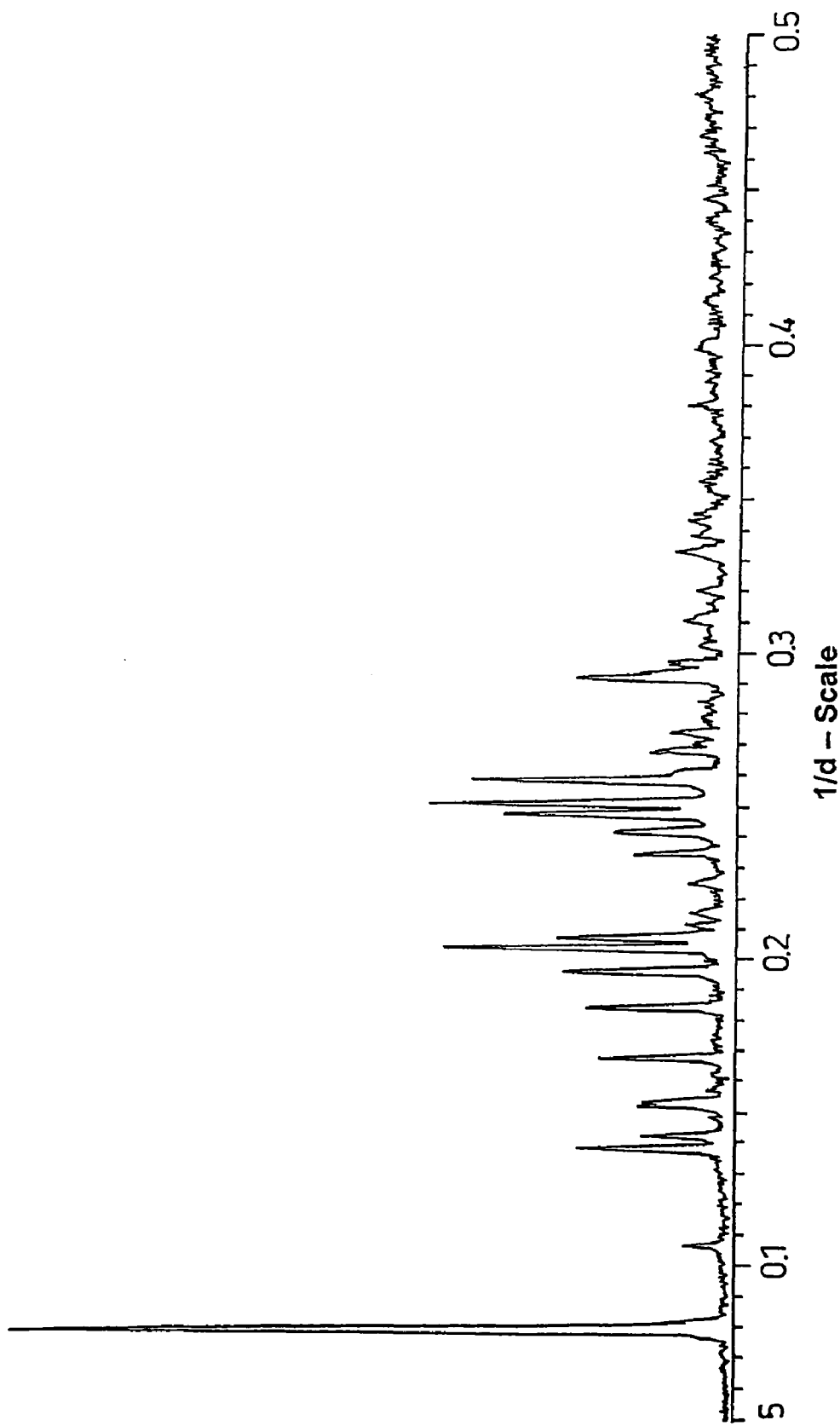
FIG. 10 shows an X-ray powder diffractogram for the crystalline form of Compound D, methanesulphonic acid salt, obtained by way of Example 10.

The crystals (Methods I to VII) were analyzed by XRPD and the results are tabulated below (Table 10) and are shown in FIG. 10.

TABLE 10

| d value (Å) | Intensity (%) |
|---|---|
| 12.7 | 100 |
| 9.4 | 6 |
| 7.3 | 20 |
| 7.1 | 11 |
| 6.8 | 3 |
| 6.6 | 11 |
| 6.4 | 3 |
| 6.0 | 17 |
| 5.4 | 18 |
| 5.1 | 21 |

TABLE 10-continued

| d value (Å) | Intensity (%) |
|---|---|
| 4.92 | 38 |
| 4.83 | 22 |
| 4.74 | 5 |
| 4.66 | 4 |
| 4.45 | 4 |
| 4.27 | 11 |
| 4.14 | 14 |
| 4.05 | 30 |
| 3.99 | 38 |
| 3.87 | 33 |
| 3.73 | 9 |
| 3.65 | 7 |
| 3.42 | 19 |
| 3.37 | 6 |
| 3.31 | 3 |
| 3.22 | 5 |
| 3.12 | 4 |
| 3.00 | 6 |
| 2.96 | 5 |
| 2.92 | 5 |
| 2.89 | 4 |
| 2.81 | 3 |
| 2.71 | 2 |
| 2.63 | 5 |
| 2.57 | 2 |
| 2.50 | 3 |
| 2.41 | 3 |

A unit cell was determined from single crystal X-ray data. It was orthorhombic, with space group $P2_12_12_1$ and the following dimensions: a=7.772 Å, b=14.250 Å, c=25.75 Å, $\alpha=\beta=\gamma=90°$, and V=1717.2 Å$^3$.

DSC showed an endotherm with an extrapolated onset temperature of ca. 167° C. TGA showed a decrease in mass of ca. 1.2% (w/w) between 25 and 100° C.

EXAMPLE 11

Crystallisation of Compound D, hippuric acid salt

A solution of hippuric acid (0.8 g) in methanol (20 mL) was added to a solution of Compound D (2.00 g, prepared analogously to the processes described in Example 9 above) in methanol (5 mL). Then, the solution was is concentrated in vacuo, to give an oil. Diethyl ether (20 mL) was added and the mixture was re-concentrated to give a foam. Stirring in ether (100 mL) overnight and filtering yielded 2.22 g of title compound (79 %). The salt was dried in vacuo at 34° C., yielding 2.19 g (78%).

The presence of the hippuric acid salt was confirmed by NMR.

Figure 11:
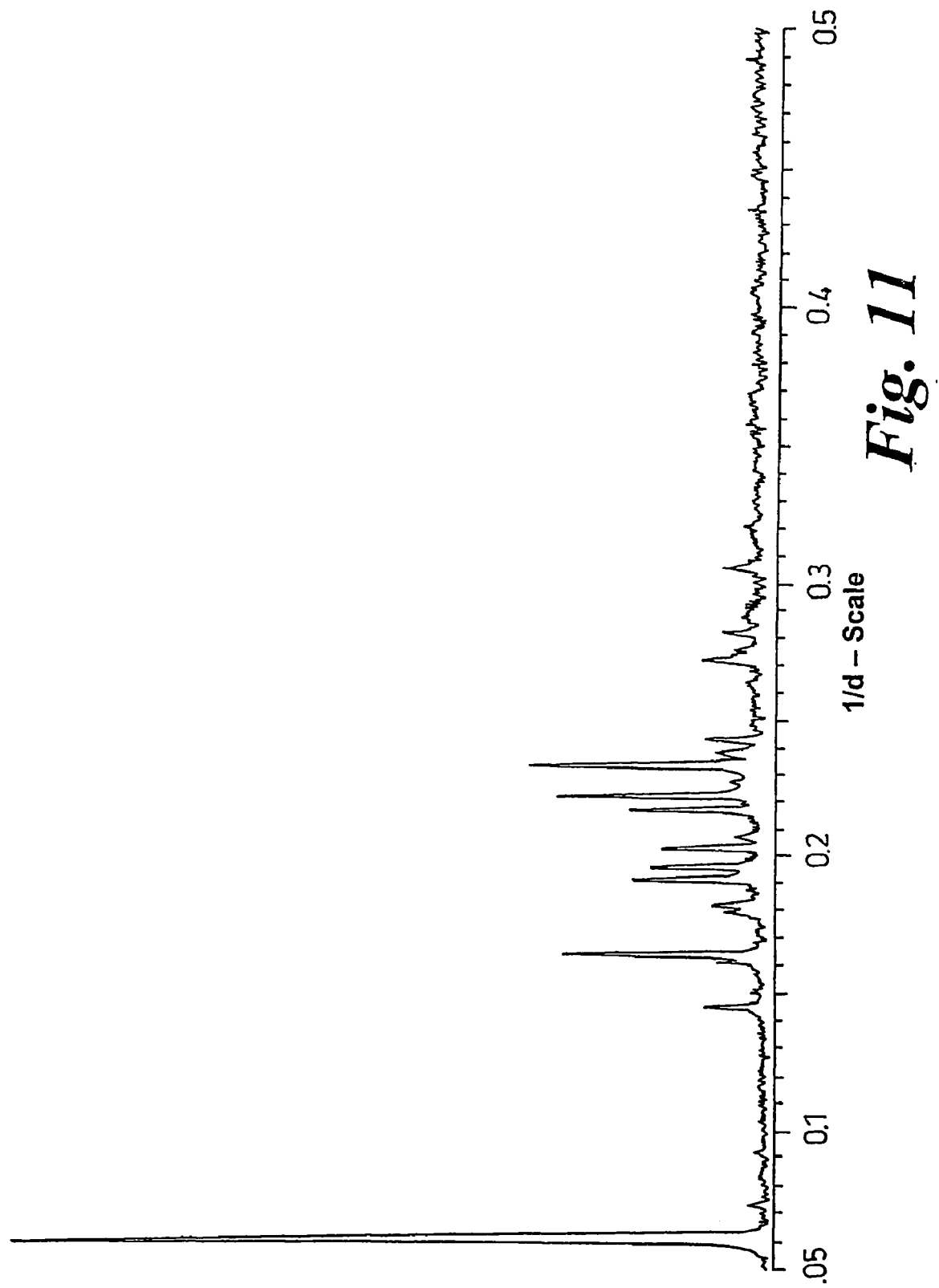
FIG. 11 shows an X-ray powder diffractogram for the crystalline form of Compound D, hippuric acid salt, obtained by way of Example 11.

The crystals were analyzed by XRPD and the results are tabulated below (Table 11) and are shown in FIG. 11.

TABLE 11

| d value (Å) | Intensity (%) |
|---|---|
| 16.4 | 100 |
| 13.8 | 3 |
| 6.9 | 8 |
| 6.2 | 6 |
| 6.1 | 25 |
| 5.6 | 5 |
| 5.5 | 7 |
| 5.2 | 17 |
| 5.1 | 15 |
| 4.93 | 13 |
| 4.82 | 4 |

TABLE 11-continued

| d value (Å) | Intensity (%) |
|---|---|
| 4.61 | 18 |
| 4.50 | 26 |
| 4.28 | 30 |
| 4.20 | 6 |
| 4.11 | 8 |
| 3.68 | 8 |
| 3.54 | 5 |
| 3.27 | 5 |

EXAMPLE 12

Crystallisation of Compound C (i) Compound C was prepared analogously to the procedure described in preparation C above, except that the following final process step was undertaken: A 3 L, three-neck flask was equipped with a magnetic stirrer, a thermometer and a reflux condenser. The flask was charged with unpurified 4-[4-(9-oxa-3,7-diazabicyclo[3.3.1]non-3-yl)butyl]benzonitrile (see Preparation C(v) above, 25.8 g, 88 mmol), dichloromethane (0.88 L) and tert-butyl 2-bromoethylcarbamate (see Preparation B(I)(i) above, 27.7 g, 123 mmol). Triethylamine (0.0197 L, 0.141 mol) was then added. The clear solution was refluxed for 12 hours under a nitrogen atmosphere and then cooled to room temperature. The progress of the reaction was monitored by TLC analysis and it was found to be complete at this point.

(ii) The reaction mixture was transferred to a separating funnel and washed sequentially with water (200 mL), 15% aqueous sodium hydroxide (200 mL), water (200 mL), and brine (200 mL). The organic layer was dried over magnesium sulphate and concentrated under vacuum. The resulting yellow viscous oil was chromatographed on silica gel, eluting first with 9:1 dichloromethane/methanol, then with 9:1:0.02 dichloromethane/methanol/28% aqueous ammonium hydroxide to afford crude Compound C (25.1 g, 66 % yield) as an off-white solid. The earlier fractions (5.1 g) from chromatography were found to contain a small amount of a less polar impurity (by TLC analysis, eluting with 9:1:0.05 dichloromethane/methanol/28% aqueous ammonium hydroxide) while the later fractions (20 g) gave one spot by TLC analysis. The earlier fractions (5.1 g) were combined with a previously prepared batch of Compound C (7.1 g, containing a slight impurity) and chromatographed on silica gel, eluting first with 19:1 dichloromethane/methanol, and then with 9:1 dichloromethane/methanol to afford a pale yellow powder (5.5 g). The powder was dissolved in dichloromethane (200 mL). The resulting solution was washed sequentially with 25% aqueous sodium hydroxide (50 mL), water (50 mL), and brine (40 mL). The material was then dried over magnesium sulphate and concentrated under vacuum to afford crude title compound as an off-white powder (5 g). The 20 g fraction was dissolved in dichloromethane (500 mL). The organic layer was washed sequentially with 25% aqueous sodium hydroxide (100 ml), water (100 ml), and brine (100 mL). The material was then dried over magnesium sulphate and concentrated under vacuum to afford as an off-white powder (19 g). The lots were blended together.

Figure 12:
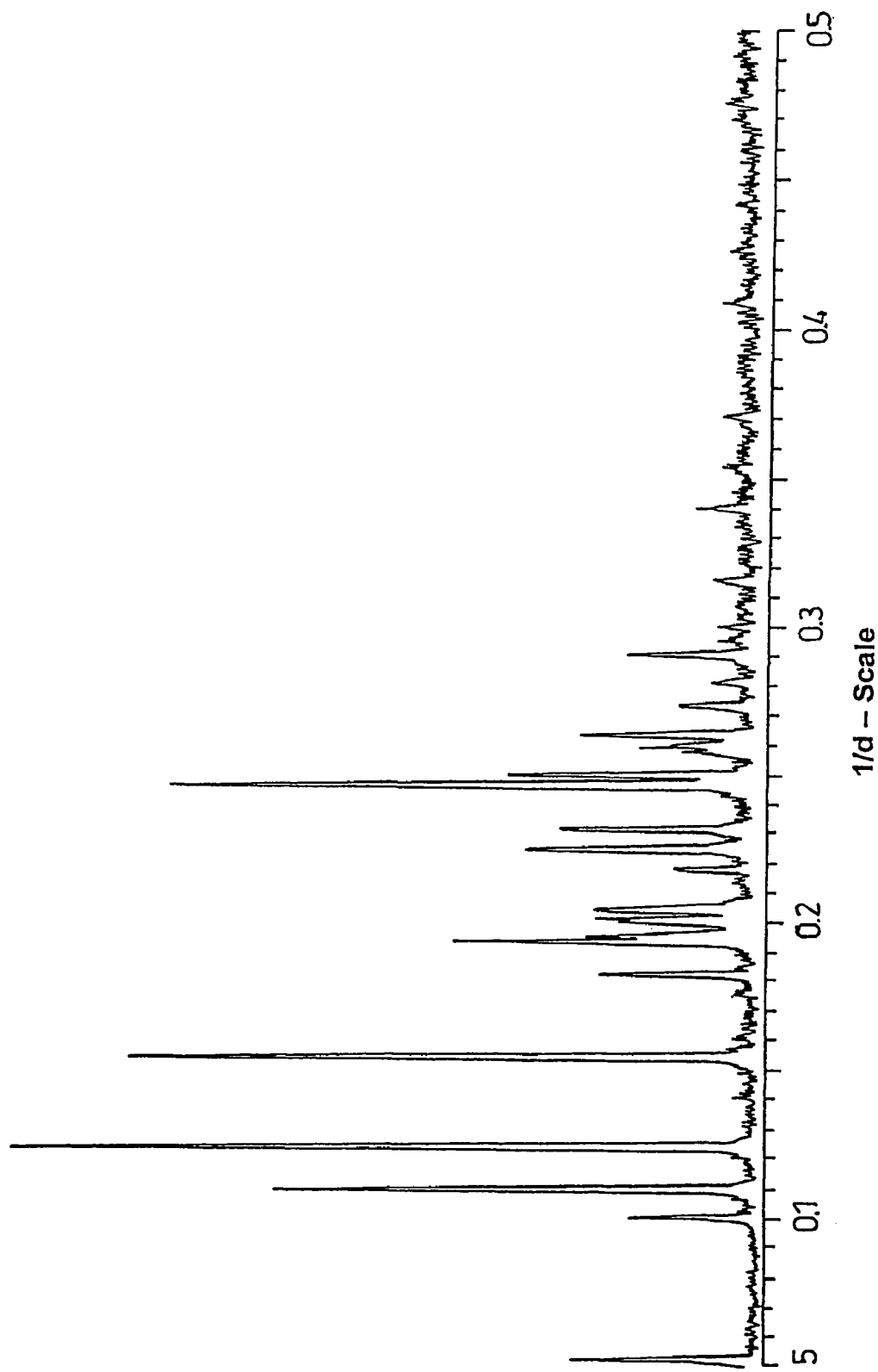
FIG. 12 shows an X-ray powder diffractogram for the crystalline form of Compound C, obtained by way of Example 12.

The crystals were analyzed by XRPD and the results are tabulated below (Table 12) and are shown in FIG. 12.

TABLE 12

| d value (Å) | Intensity (%) |
|---|---|
| 19.4 | 24 |
| 10.0 | 16 |
| 9.1 | 64 |
| 8.1 | 100 |
| 6.5 | 84 |
| 5.5 | 19 |
| 5.2 | 41 |
| 5.1 | 21 |
| 4.99 | 20 |
| 4.90 | 21 |
| 4.60 | 9 |
| 4.46 | 30 |
| 4.32 | 25 |
| 4.06 | 78 |
| 4.00 | 33 |
| 3.85 | 15 |
| 3.80 | 23 |
| 3.66 | 10 |
| 3.56 | 5 |
| 3.44 | 17 |
| 3.33 | 4 |
| 3.16 | 5 |
| 2.94 | 8 |
| 2.82 | 4 |
| 2.69 | 4 |
| 2.44 | 5 |

DSC showed an endothermic peak with an extrapolated onset temperature of ca. 97° C. TGA showed a decrease in mass of ca. 0.6% (w/w) between 25 and 120° C.

EXAMPLE 13

Crystallisation of Compound C, methanesulphonic acid salt

Compound C (250 mg, prepared in analogous fashion to the process described in Example 12 above) was dissolved in methanol (10 mL). Methanesulphonic acid (56 mg, 38 μL) was added to the solution. The methanol was removed under reduced pressure and the remaining gum was re-dissolved in the minimum amount of hot iso-propanol possible. The solution was seeded with previously prepared salt (prepared by slow evaporation of solvent from a small portion of a solution of title compound, prepared in analogous fashion to this procedure) and left in the fridge for several days to crystallise. The resulting crystals were collected by filtration and washed with a small amount of cold iso-propanol (recovered 220 mg, 72%).

Figure 13:
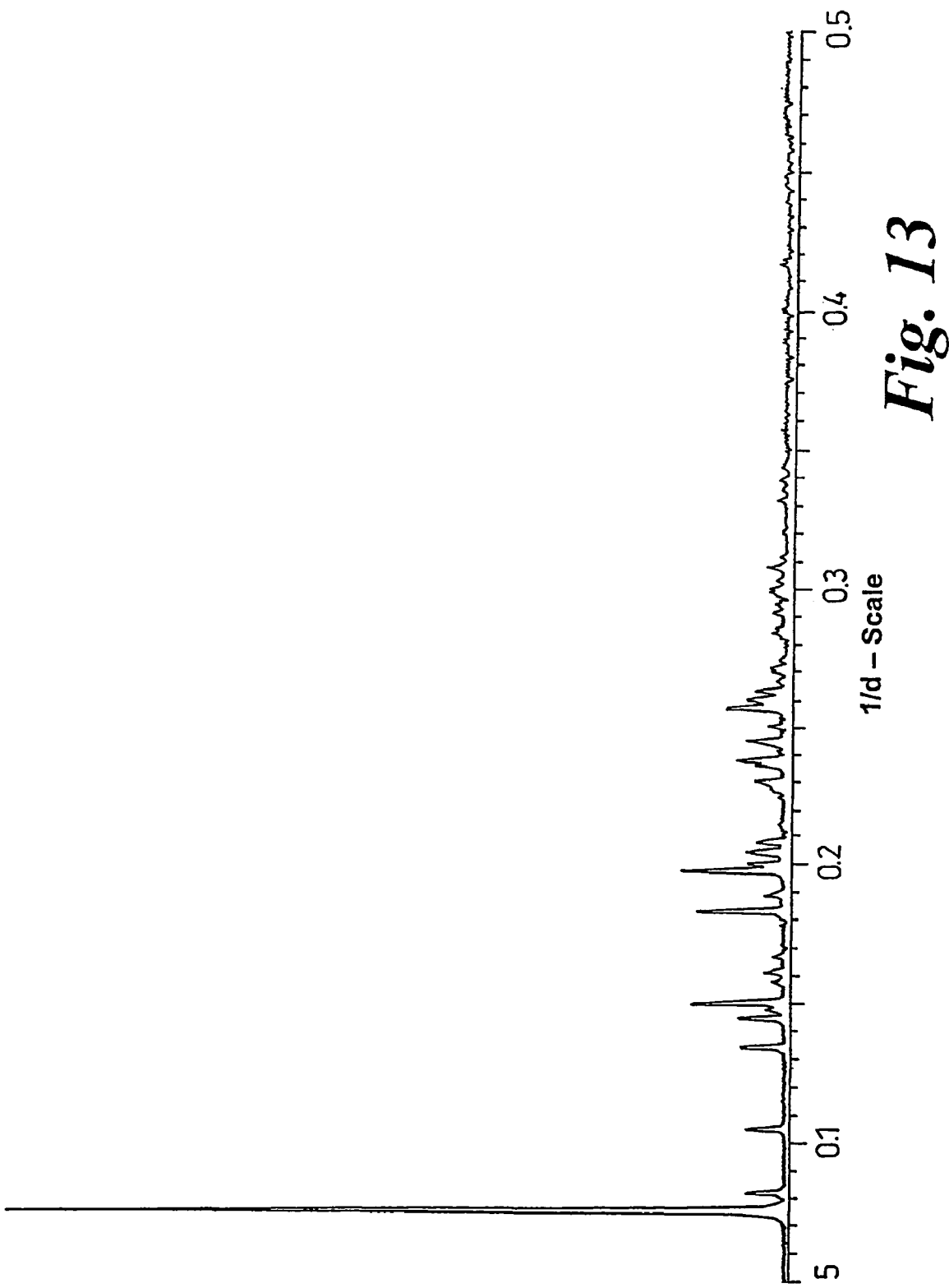
FIG. 13 shows an X-ray powder diffractogram for the crystalline form of Compound C, methanesulphonic acid salt, obtained by way of Example 13.

The crystals were analyzed by XRPD and the results are tabulated below (Table 13) and are shown in FIG. 13.

TABLE 13

| d value (Å) | Intensity (%) |
|---|---|
| 13.3 | 100 |
| 12.3 | 5 |
| 9.6 | 5 |
| 7.5 | 6 |
| 6.9 | 6 |
| 6.8 | 3 |
| 6.7 | 12 |
| 6.4 | 2 |
| 6.2 | 2 |
| 6.0 | 2 |
| 5.5 | 12 |
| 5.3 | 2 |
| 5.1 | 13 |

TABLE 13-continued

| d value (Å) | Intensity (%) |
|---|---|
| 5.0 | 5 |
| 4.89 | 5 |
| 4.81 | 4 |
| 4.34 | 4 |
| 4.23 | 4 |
| 4.20 | 6 |
| 4.08 | 5 |
| 3.99 | 2 |
| 3.89 | 8 |
| 3.85 | 5 |
| 3.80 | 4 |
| 3.68 | 2 |
| 3.52 | 2 |
| 3.49 | 2 |
| 3.43 | 2 |
| 3.39 | 2 |
| 3.33 | 2 |
| 3.25 | 3 |
| 3.01 | 2 |
| 2.94 | 2 |
| 2.90 | 1 |
| 2.80 | 1 |
| 2.49 | 1 |
| 2.40 | 2 |

DSC showed endothermic peaks with extrapolated onset temperatures of ca. 145° C. (minor) and 170° C. (major). TGA showed a decrease in mass of ca. 0.9% (w/w) between 25 and 105° C.

EXAMPLE 14

Crystallisation of Compound C, para-toluenesulphonic acid salt

Compound C (250 mg, prepared in analogous fashion to the process described in Example 12 above) was dissolved in methanol (10 mL). Toluenesulphonic acid (110 mg) was added to the solution. The methanol was removed under reduced pressure and the remaining gum was re-dissolved in the minimum amount of hot ethyl acetate possible. The solution was seeded with previously prepared salt (prepared by slow evaporation of solvent from a small portion of a solution of title compound, prepared in analogous fashion to this procedure) and left in the fridge for several days to crystallise. The resulting crystals were collected by filtration and washed with a small amount of cold ethyl acetate (recovered 280 mg, 78%).

Figure 14:
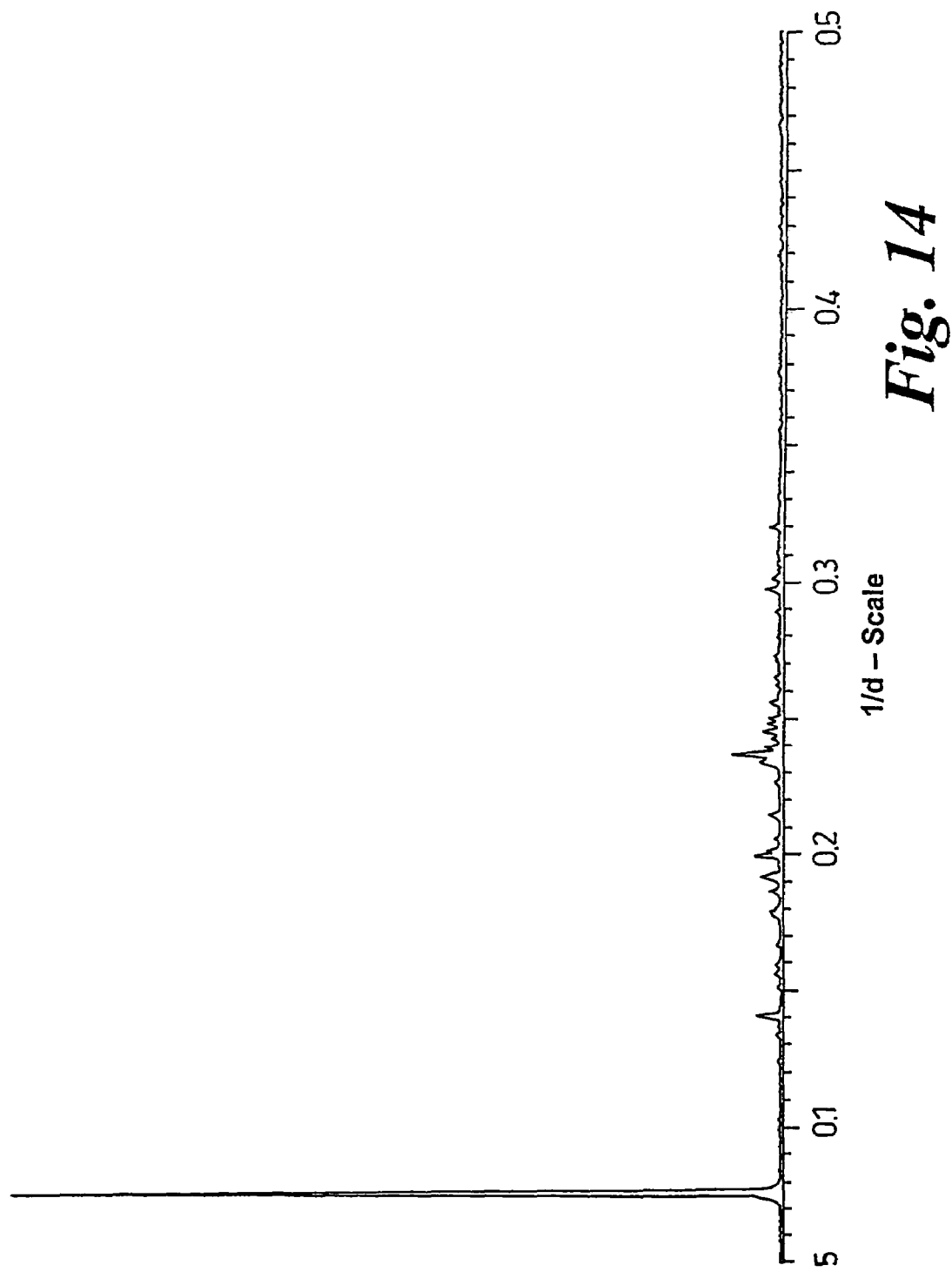
FIG. 14 shows an X-ray powder diffractogram for the crystalline form of Compound C, para-toluenesulphonic acid salt, obtained by way of Example 14.

The crystals were analyzed by XRPD and the results are tabulated below (Table 14) and are shown in FIG. 14.

TABLE 14

| d value (Å) | Intensity (%) |
|---|---|
| 13.2 | 100 |
| 8.1 | 0.5 |
| 7.5 | 0.7 |
| 7.1 | 3 |
| 6.6 | 0.7 |
| 6.4 | 0.9 |
| 6.3 | 0.7 |
| 6.0 | 0.8 |
| 5.6 | 1 |
| 5.4 | 2 |
| 5.2 | 3 |
| 5.0 | 4 |
| 4.97 | 2 |
| 4.86 | 0.8 |

TABLE 14-continued

| d value (Å) | Intensity (%) |
|---|---|
| 4.67 | 2 |
| 4.42 | 0.7 |
| 4.28 | 3 |
| 4.24 | 7 |
| 4.19 | 2 |
| 4.12 | 1 |
| 4.08 | 2 |
| 4.03 | 2 |
| 4.01 | 1 |
| 3.92 | 1 |
| 3.82 | 0.7 |
| 3.78 | 0.8 |
| 3.66 | 0.8 |
| 3.57 | 0.5 |
| 3.46 | 1 |
| 3.36 | 2 |
| 3.32 | 1 |
| 3.12 | 2 |

DSC showed an endothermic peak with an extrapolated onset temperature of ca. 138° C. TGA showed a decrease in mass of ca. 0.2% (w/w) between 25 and 150° C.

EXAMPLE 15

Compound D, [(biphenyl-4-carbonyl)amino]acetic acid salt (a) [(Biphenyl-4-carbonyl)amino]acetic acid methyl ester Dichloromethane (50 mL) and then triethylamine (11.2 mL, 79.6 mmol, 2.0 eq) were added to glycine methyl ester hydrochloride (5.0 g, 39.8 mmol, 1.0 eq). The mixture was stirred and cooled to −5° C. using an ice/methanol bath. A suspension of biphenyl-4-carbonyl chloride (8.26 g, 39.8 mmol, 1.0 eq) in dichloromethane (25 mL) was added over 22 minutes. The mixture was stirred for 3 hours at −5° C., and then left to stir at room temperature overnight (16 hours). Water (75 mL) was added and the mixture was stirred rapidly for 30 minutes at room temperature. The layers were separated. The organic layer was washed with water (75 mL), then evaporated to dryness using a rotary evaporator to give an off-white solid (6.58 g, 62%).

$^1$H-NMR (300 MHz, CDCl$_3$) δ 3.82 (s, 3H), 4.29 (d, J=5.1 Hz, 2H), 6.68 (s, 1H), 7.3–7.5 (m, 3H), 7.62 (d, J=4.8 Hz, 2H), 7.68 (d, J=8.1 Hz, 2H), 7.90 (d, J=8.4 Hz, 2H) m.p. 127–128° C.

(b) [(Biphenyl-4-carbonyl)amino]acetic acid

[(Biphenyl-4-carbonyl)amino]acetic acid methyl ester (6.58 g, 25 mmol, 1.0 eq., from step (a) above) was added to the flask followed by aqueous sodium hydroxide (1 M, 84 mL, 50 mmol, 2.0 eq). The mixture was heated to 50° C. using an oil bath for 5 hours. The solution was then stirred overnight (16 hours) at room temperature. On cooling, a white precipitate formed. The mixture was cooled further to 5° C. using an ice/water bath. Concentrated hydrochloric acid (8 mL) was added very slowly to the cooled solution, ensuring that the temperature did not rise above 10° C. The mixture was stirred for 15 minutes and was then filtered. The white solid was air dried for 30 minutes and then dried in vacuo at 40° C. for 16 hours to give an off-white solid (5.75 g, 93%).

$^1$H-NMR (300 MHz, DMSO-d$_6$) δ 3.95 (d, J=5.7 Hz, 2H), 7.35–7.5 (m, 3H), 7.7–7.8 (m, 4H), 7.97 (d, J=6.9 Hz, 2H), 8.89 (t, J=6.0 Hz, 1H), 12.58 (s, 1H) mp 217–217.5° C.

(c) Recrystallisation of [(biphenyl-4-carbonyl)amino]acetic Acid

Methanol (100 mL, 20 vols) was added to [(biphenyl-4-carbonyl)amino]-acetic acid (5.0 g, from step (b) above). The mixture was heated to 62° C. using an oil bath whilst being stirred. The resulting pale orange solution was held at this temperature for 10 minutes. The solution was allowed to cool to room temperature, and then was cooled further to 5° C. using an ice/water bath. Crystallisation began at approximately 30° C. The precipitate was collected by filtration, air dried for 15 minutes, then dried in vacuo at 40° C. for 26 hours to give colourless crystals (2.9 g, 58%).

$^1$H-NMR (300 MHz, DMSO-d$_6$) δ 3.95 (d, J=5.7 Hz, 2H), 7.35–7.5 (m, 3H), 7.7–7.8 (m, 4H), 7.97 (d, J=6.9 Hz, 2H), 8.89 (t, J=6.0 Hz, 2H), 12.58 (s, 1H)

(d) Compound D, [(biphenyl-4-carbonyl)amino]acetic Acid Salt

[(Biphenyl-4-carbonyl)amino]acetic acid (1.14 g, see steps (b) or (c) above) and Compound D (2 g, prepared analogously to methods described hereinbefore) were dissolved in hot iso-propanol (40 mL). On cooling to room temperature a crystalline precipitate formed which was filtered, washed with iso-propanol (2×20 mL) and sucked dry on the filter. Drying for 6 hours in vacuo at 40° C. gave the salt as a colourless, crystalline solid (2.50 g, 80%).

$^1$H-NMR (300 MHz, DMSO-d$_{6+}$) δ 1.34 (9H, s), 2.25 (2H, t), 2.3–2.5 (4H, m), 2.6–2.7 (1H, m), 2.7–2.8 (1H, m), 2.85–3.0 (4H, m), 3.0–3.1 (2H, m), 3.82 (2H, s), 3.88 (2H, d), 3.95–4.05 (2H, m), 4.1–4.2 (1H, m), 6.65 (1H, t), 7.14 (2H, d), 7.35–7.55 (3H, m), 7.7–7.85 (6H, m), 7.96 (2H, d), 8.75 (1H, t) mp 143–143.5° C.

Figure 15:
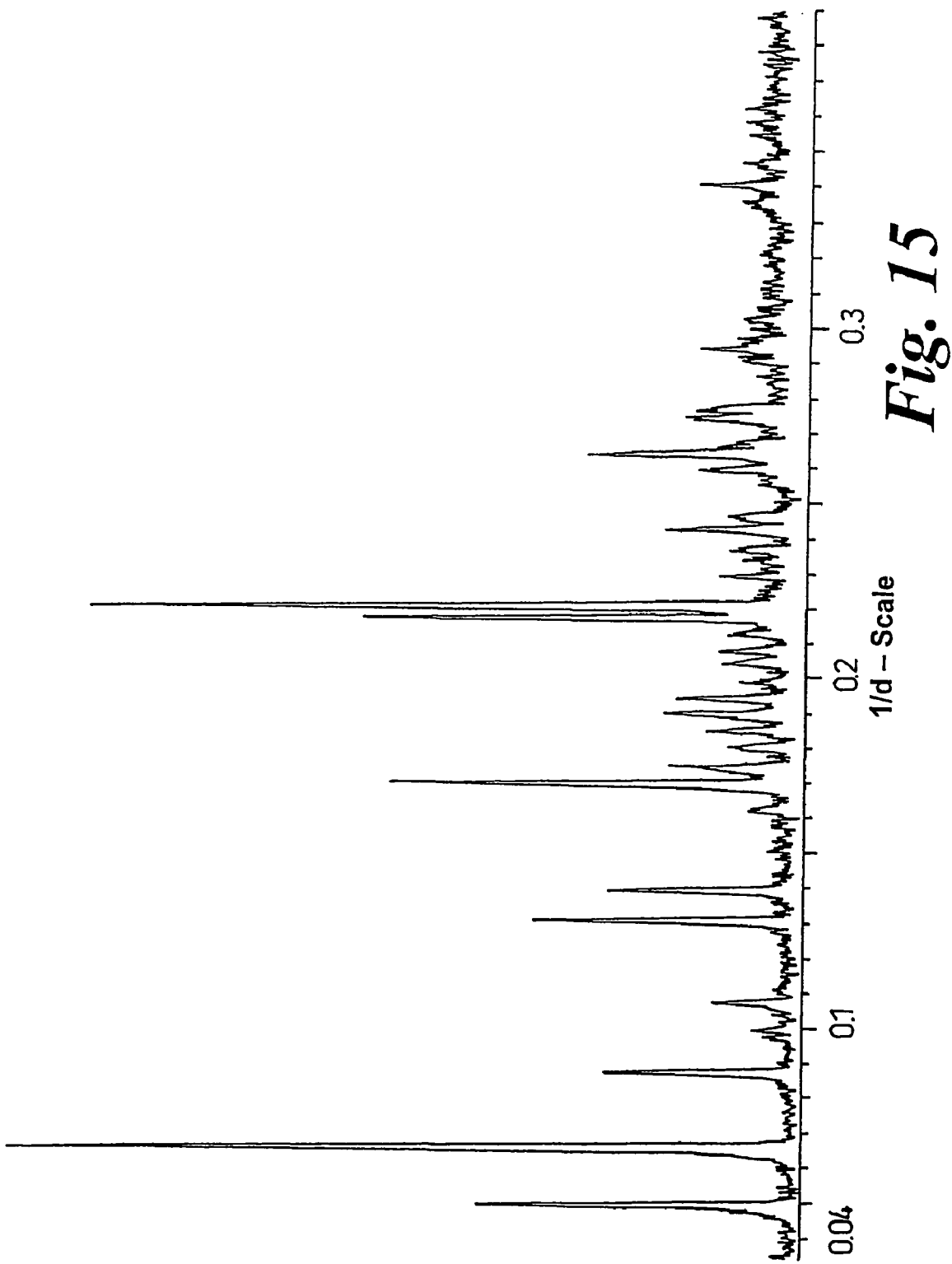
FIG. 15 shows an X-ray powder diffractogram for the crystalline form of Compound D, [(biphenyl-4-carbonyl)amino]acetic acid salt, obtained by way of Example 15.

The crystals were analyzed by XRPD and the results are tabulated below (Table 15) and are shown in FIG. 15.

TABLE 15

| d value (Å) | Intensity (%) |
|---|---|
| 20.4 | 45 |
| 15.3 | 100 |
| 11.5 | 24 |
| 10.3 | 4 |
| 10.0 | 6 |
| 9.4 | 11 |
| 7.7 | 34 |
| 7.2 | 23 |
| 6.2 | 5 |
| 5.9 | 49 |
| 5.7 | 15 |
| 5.6 | 6 |
| 5.4 | 11 |
| 5.3 | 13 |
| 5.2 | 14 |
| 5.0 | 6 |
| 4.89 | 8 |
| 4.81 | 9 |
| 4.70 | 6 |
| 4.60 | 57 |
| 4.54 | 89 |
| 4.36 | 9 |
| 4.22 | 7 |
| 4.13 | 18 |
| 4.06 | 8 |
| 3.85 | 13 |
| 3.79 | 27 |

TABLE 15-continued

| d value (Å) | Intensity (%) |
| --- | --- |
| 3.64 | 12 |
| 3.61 | 11 |
| 3.40 | 11 |
| 3.31 | 6 |
| 2.98 | 6 |
| 2.94 | 12 |
| 2.88 | 6 |

EXAMPLE 16

Compound D, hemisuccinic acid salt

A hot solution of Compound D (5.35 g; prepared analogously to procedures described hereinbefore) and succinic acid (0.71 g) in iso-propanol (20 mL) was seeded with Compound D, hemisuccinic acid salt (prepared by slow evaporation of solvent from a small portion of a solution of title compound, prepared in analogous fashion to this procedure), and then left to stand in the fridge. The following day, the precipitated solid was collected by filtration and washed with iso-propanol (20 mL). The solid was sucked dry on the filter and then dried in vacuo at 40° C. for 2 hours to give the title compound as a white solid. The filtrate was allowed to evaporate totally by being left open to the atmosphere. This left a solid that was slurried in iso-propanol (20 mL) and then filtered, washing on the filter with iso-propanol (70 mL). The solid was sucked dry on the filter and then dried in vacuo at 40° C. for 90 minutes to give the title compound as a white solid (2.8 g).

mp 112–114° C.

Figure 16:
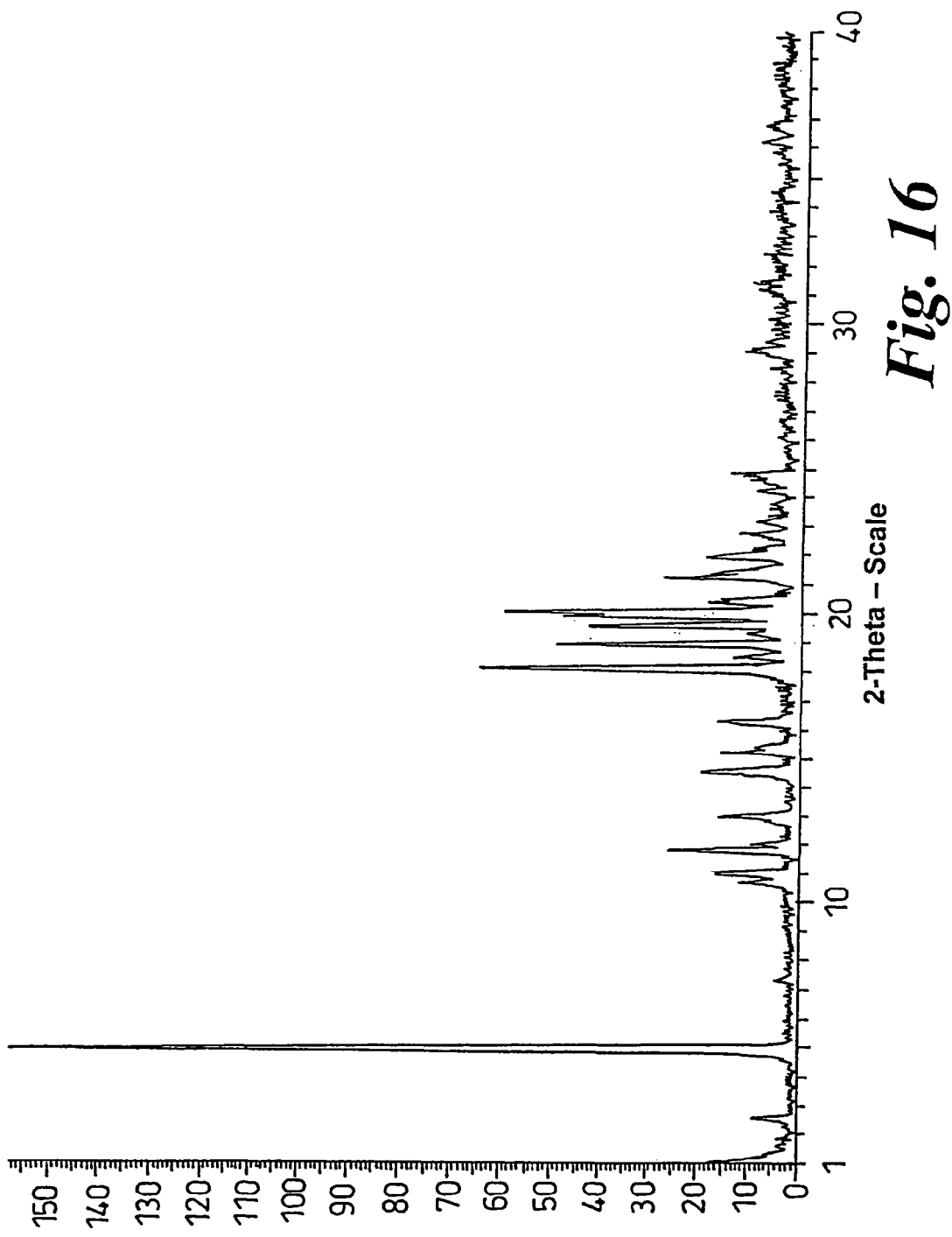
FIG. 16 shows an X-ray powder diffractogram for the crystalline form of Compound D, hemisuccinic acid salt, obtained by way of Example 16.

The crystals were analyzed by XRPD and the results are tabulated below (Table 16) and are shown in FIG. 16.

TABLE 16

| d value (Å) | Intensity (%) |
| --- | --- |
| 35.4 | 5 |
| 18.0 | 100 |
| 12.1 | 2 |
| 8.3 | 7 |
| 8.0 | 12 |
| 7.5 | 15 |
| 7.3 | 5 |
| 6.8 | 10 |
| 6.1 | 12 |
| 5.8 | 9 |
| 5.4 | 9 |
| 4.89 | 41 |
| 4.79 | 7 |
| 4.68 | 28 |
| 4.59 | 5 |
| 4.54 | 26 |
| 4.43 | 37 |
| 4.35 | 10 |
| 4.18 | 16 |
| 4.04 | 10 |
| 3.99 | 4 |
| 3.90 | 5 |
| 3.83 | 4 |
| 3.67 | 4 |
| 3.58 | 8 |
| 3.13 | 2 |
| 3.07 | 6 |
| 3.03 | 3 |
| 2.47 | 4 |
| 2.44 | 3 |

EXAMPLE 17

Compound D, (3,4-dichlorobenzoylamino)acetic acid salt (a) (3,4Dichlorobenzoylamino)acetic acid methyl ester Dichloromethane (150 mL) and then triethylamine (33.0 mL, 234 mmol, 2.0 eq.) were added to glycine methyl ester hydrochloride (14.7 g, 117 mmol, 1.0 eq.). The mixture was stirred and cooled to 2° C. using an ice/water bath. A solution of 3,4-dichlorobenzoyl chloride (24.55 g, 117 mmol, 1.0 eq.) in dichloromethane (75 mL) was added over 7 minutes. The mixture was stirred for 1 hour at 2° C., then left to stir at room temperature overnight (16 hours). Water (225 mL) was added and the mixture was stirred rapidly for 30 minutes at room temperature. The layers were separated. The organic layer was washed with water (225 mL), then evaporated to dryness using a rotary evaporator to give an off-white solid. The isolated solid (26.18 g, 85%) was added to dichloromethane (300 mL, 10 vols.) with 1 M sodium hydroxide solution (300 mL, 10 vols). The lower organic layer was concentrated to dryness in vacuo (25.91 g, 84%).

m.p. 133.2–134.3° C. $\delta_H$ (300 MHz, CDCl$_3$) 3.66 (1H, s, CH$_3$), 4.03 (2H, d, J=6, CH$_2$), 7.78–7.87 (2H, m, CH), 8.100 (1H, s, CH), 9.18 (1H, t, J=5.7, NH).

(b) (3,4-Dichlorobenzoylamino)acetic acid (3,3-Dichlorobenzoylamino)acetic acid methyl ester (25.91 g, 100 mmol, 1.0 eq., see step (a) above) was added to the flask followed by aqueous sodium hydroxide (1 M, 198 mL, 200 mmol, 2.0 eq.). The mixture was heated to 50° C. using an oil bath for 2 hours. On cooling, a white precipitate formed. The mixture was cooled further to 5° C. using an ice/water bath. Concentrated hydrochloric acid (60 mL) was added very slowly to the cooled solution, ensuring that the temperature did not rise above 10° C. The mixture was stirred for 10 minutes and was then filtered. The white solid was air dried for 15 minutes and then dried in vacuo at 40° C. for 16 hours to give an off-white solid (19.15 g, 78%).

m.p. 140.0–140.3° C. $\delta_H$ (300 MHz, DMSO-D$_6$) 3.94 (2H, d, J=6, CH$_2$), 7.77–7.87 (2H, m, CH), 8.10 (1H, s, CH), 9.06 (1H, t, J=6), 12.66 (1H, bs, OH)

(c) Compound D, (3,4-dichlorobenzoylamino)acetic acid salt (3,4-Dichlorobenzoylamino)acetic acid (0.56 g, see step (b) above) and Compound D (1.02 g; prepared analogously to procedures described hereinbefore) were dissolved in hot ethyl acetate (4 mL). On cooling to room temperature, a crystalline precipitate formed which was filtered, washed with ethyl acetate (15 mL) and sucked dry on the filter. Drying overnight in vacuo at 40° C. gave the title salt as a colourless, crystalline solid (0.92 g, 58%).

m.p. 128.5–130.5° C. $^1$H-NMR (400 MHz, DMSO-D$_6$) δ 1.34 (9H, s), 2.26 (2H, t), 2.3–2.5 (3H, m), 2.5–2.6 (1H, m), 2.6–2.7 (1H, m), 2.7–2.8 (1H, m), 2.85–3.0 (4H, m), 3.0–3.1 (2H, m), 3.8–3.9 (4H, m), 4.01 (2H, d), 4.1–4.2 (1H, m), 6.69 (1H, t), 7.12 (2H, d), 7.7–7.8 (3H, m), 7.84 (1H, dd), 8.09 (1H, dd) 8.92 (1H, t)

Figure 17:
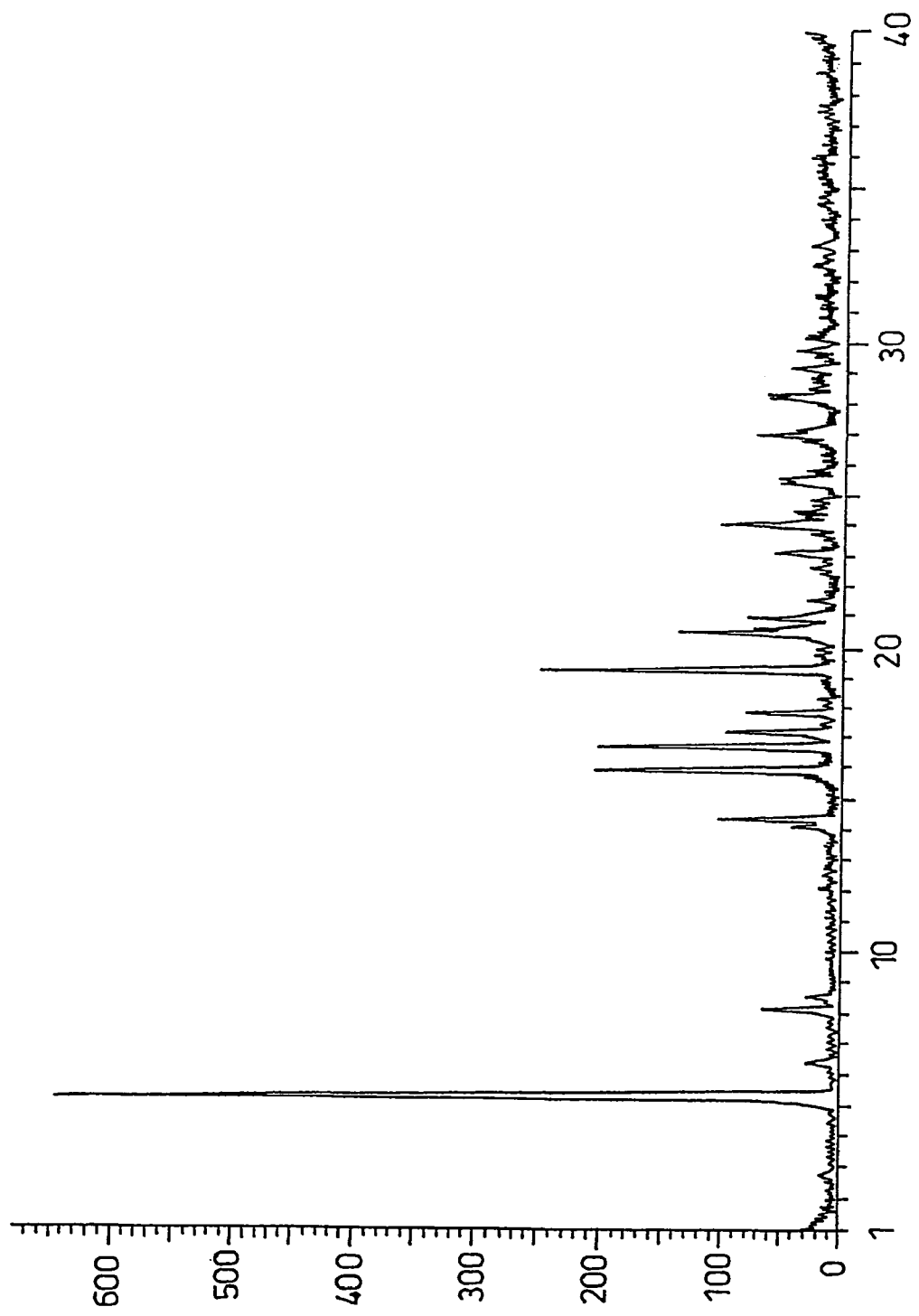
FIG. 17 shows an X-ray powder diffractogram for the crystalline form of Compound D, (3,4-dichlorobenzoylamino)acetic acid salt, obtained by way of Example 17.

The crystals were analyzed by XRPD and the results are tabulated below (Table 17) and are shown in FIG. 17.

TABLE 17

| d value (Å) | Intensity (%) |
| --- | --- |
| 16.6 | 100 |
| 13.8 | 4 |
| 10.9 | 10 |
| 10.3 | 3 |
| 6.3 | 6 |
| 6.2 | 15 |
| 5.5 | 31 |
| 5.3 | 30 |
| 5.1 | 14 |
| 5.0 | 12 |
| 4.60 | 38 |
| 4.33 | 20 |
| 4.30 | 11 |
| 4.22 | 11 |
| 4.11 | 3 |
| 3.85 | 8 |
| 3.70 | 13 |
| 3.50 | 6 |
| 3.30 | 10 |
| 3.16 | 7 |
| 3.06 | 6 |
| 2.99 | 5 |
| 2.95 | 3 |

EXAMPLE 18

Compound D,
[(naphthalene-2-carbonyl)amino]acetic acid salt (a) [(Naphthalene-2-carbonyl)amino]acetic acid methyl ester Dichloromethane (66 mL) and then triethylamine (14.6 mL, 105 mmol, 2.0 eq.) were added to glycine methyl ester hydrochloride (6.61 g, 52.5 mmol, 1.0 eq.). A white precipitate appeared on the addition of the triethylamine, and the solution became a lot thicker. The mixture was stirred and cooled to 2° C. using an ice/water bath. A solution of 2-naphthoyl chloride (10.07 g, 52.5 mmol, 1.0 eq.) in dichloromethane (33 mL) was added over 15 minutes. The pale brown mixture was stirred for 25 hours at 5° C. Water (100 mL) was added and the mixture was stirred rapidly for 30 minutes at room temperature. The layers were separated. The organic layer was washed with sodium hydroxide (1 M, 100 mL) and then evaporated to dryness using a rotary evaporator to give an off-white solid (1221 g, 96%).

m.p. 117.7–118.1° C. $\delta_H$ (400 MHz, DMSO-D$_6$) 3.68 (3H, s, CH$_3$), 4.08 (2H, d, J=4.5, CH$_2$), 7.59–7.66 (2H, m, CH), 7.935–8.015 (4H, m, CH), 8.491 (1H, s, CH), 9.124 (1H, t, J=45.6, NH)

(b) [(Naphthalene-2-carbonyl)amino]acetic acid

[(Naphthalene-2-carbonyl)amino]acetic acid methyl ester (10.03 g, 41 mmol, 1.0 eq., see step (a) above) was added to the flask followed by aqueous sodium hydroxide (1 M, 120 mL, 123 mmol, 3.0 eq.). The mixture was heated to 55° C. using an oil bath for 2 hours. The mixture was cooled to 5° C. using an ice/water bath. Concentrated hydrochloric acid (50 mL) was added very slowly to the cooled solution, ensuring that the temperature did not rise above 10° C. A dense yellow precipitate was formed. The mixture was stirred for 10 minutes and was then filtered. The yellow solid was air lo dried for 15 minutes and then dried in vacuo at 40° C. for 16 hours (8.73 g, 93%). Methanol (50 mL, 10 vols) and water (100 ml, 20 vols) were added to a portion of the sub-title compound (5.0 g, 22 mmol). The mixture was heated to 70° C. using an oil bath whilst being stirred. The solution was held at this temperature for 10 minutes, and then was allowed to cool further to 5° C. using an ice/water bath. Crystallisation began at approximately 30° C. The precipitate was collected by filtration, air dried for 15 minutes, then dried in vacuo at 40° C. for 2 hours (3.2 g, 64%). The isolated sub-title compound (3.2 g, 0.014 mol, 64%) was added to water (100 mL, 20 vols) and methanol (50 mL, 10 vols). The mixture was heated to 70° C. to dissolve the solid. The solution was allowed to cool to room temperature, crystallisation occurred on cooling. The mixture was cooled further to 2° C., and then was filtered using a sinter funnel. The solid was air dried for 10 minutes, then dried in vacuo at 40° C. for 16 hours (2.21 g, 44%).

m.p. 167.1–167.4° C. $\delta_H$ (400 MHz, DMSO-D$_6$) 3.98 (2H, d, J=5.6, CH$_2$), 7.58–7.65 (2H, m, CH), 7.95–8.05 (4H, m, CH), 8.49 (1H, s, CH), 8.99 (1H, t, J=5.6, NH), 12.63 (1H, bs, OH)

(c) Compound D,
[(naphthalene-2-carbonyl)amino]acetic acid salt

[(Naphthalene-2-carbonyl)amino]acetic acid (0.51 g, see step (b) above) and Compound D (1.01 g; prepared analogously to procedures described hereinbefore) were dissolved in methyl iso-butyl ketone (30 mL) at 100° C. On cooling to room temperature a crystalline precipitate formed which was filtered, washed with acetone (25 mL) and sucked dry on the filter. Drying over a weekend in vacuo at 40° C. gave the title salt as a colourless, crystalline solid (1.17 g, 77%).

m.p. 138.5–140° C. $^1$H-NMR (300 MHz, DMSO-D6) δ 1.34 (9H, s), 2.25 (2H, t), 2.3–2.5 (4H, m), 2.6–2.7 (1H, m), 2.7–2.8 (1H, m), 2.85–3.0 (4H, m), 3.0–3.1 (2H, m), 3.81 (2H, s), 3.92 (2H, d), 3.95–4.05 (2H, m), 4.1–4.2 (1H, m), 6.68 (1H, t), 7.11 (2H, d), 7.5–7.7 (2H, m), 7.7–7.8 (2H, m), 7.9–8.1 (4H, m), 8.47 (1H, d), 8.85 (1H, t).

Figure 18:
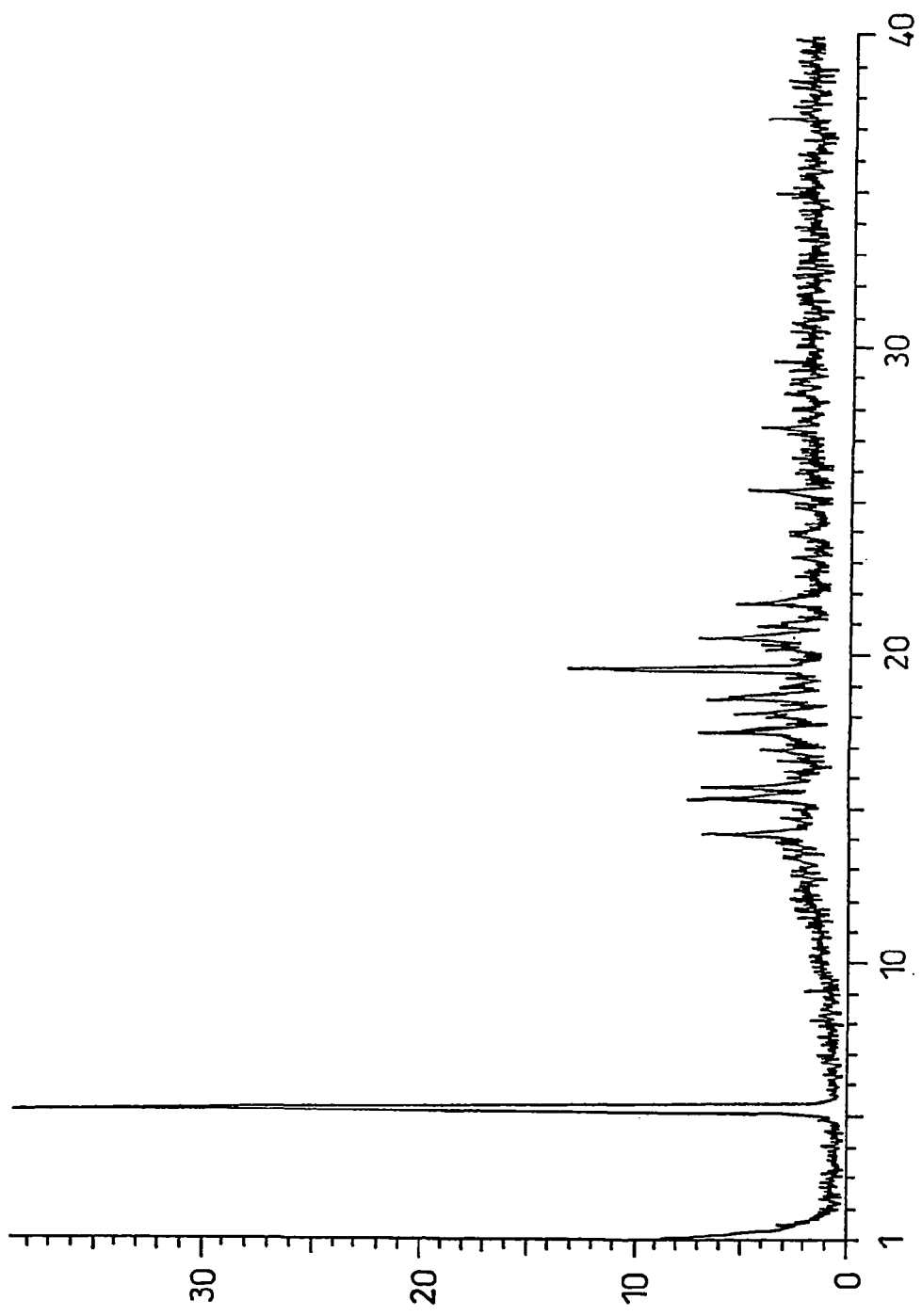
FIG. 18 shows an X-ray powder diffractogram for the crystalline form of Compound D, [(naphthalene-2-carbonyl)amino]acetic acid salt, obtained by way of Example 18.

The crystals were analyzed by XRPD and the results are tabulated below (Table 18) and are shown in FIG. 18.

TABLE 18

| d value (Å) | Intensity (%) |
| --- | --- |
| 16.8 | 100 |
| 6.2 | 15 |
| 5.8 | 11 |
| 5.6 | 15 |
| 5.2 | 6 |
| 5.1 | 15 |
| 4.90 | 10 |
| 4.76 | 14 |
| 4.66 | 4 |
| 4.53 | 31 |
| 4.37 | 7 |
| 4.31 | 15 |
| 4.23 | 7 |
| 4.08 | 10 |
| 3.70 | 3 |
| 3.51 | 9 |
| 3.25 | 7 |
| 3.12 | 5 |

EXAMPLE 19

Compound D, 2,2,3,3-tetramethyl-1,4-dibutanoic acid salt

Compound D (200 mg; prepared analogously to procedures described hereinbefore) was dissolved in ethyl acetate (10 mL). 2,2,3,3-Tetramethyl-1,4-dibutanoic acid (38.3 mg, 0.5 eq.) was dissolved in 1 mL of methanol and added to the solution of Compound D. The solvents were evaporated, ethyl acetate was added, and then this solvent was slowly evaporated by leaving the resultant in an open flask at room temperature for several days. The crystals formed were filtered off. NMR analyses showed that a 1:1 salt had been formed (~100 mg, 42%).

Figure 19:
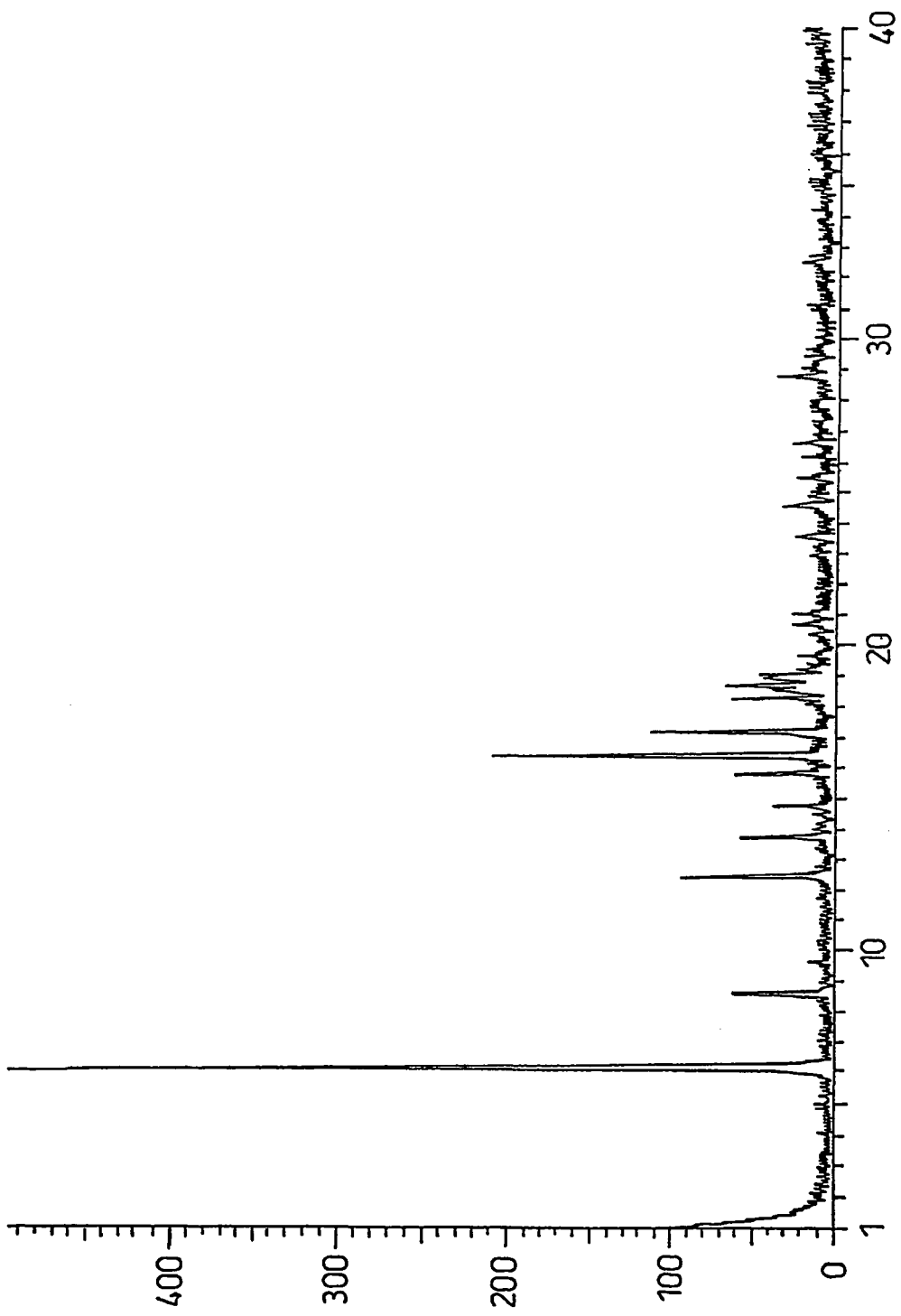
FIG. 19 shows an X-ray powder diffractogram for the crystalline form of Compound D, 2,2,3,3-tetramethyl-1,4-dibutanoic acid salt, obtained by way of Example 19.

The crystals were analyzed by XRPD and the results are tabulated below (Table 19) and are shown in FIG. 19.

TABLE 19

| d value (Å) | Intensity (%) |
|---|---|
| 14.2 | 100 |
| 10.3 | 12 |
| 7.1 | 18 |
| 6.4 | 11 |
| 6.0 | 5 |
| 5.6 | 10 |
| 5.4 | 41 |
| 5.1 | 22 |
| 4.84 | 12 |
| 4.77 | 6 |
| 4.73 | 13 |
| 4.66 | 7 |
| 4.50 | 4 |
| 4.29 | 3 |
| 4.22 | 5 |
| 3.87 | 3 |
| 3.78 | 4 |
| 3.62 | 5 |
| 3.49 | 4 |
| 3.35 | 4 |
| 3.09 | 6 |
| 2.75 | 3 |

EXAMPLE 20

Compound D, trans-D,L-1,2-cyclopentanedicarboxylic acid salt

Compound D (100 mg; prepared analogously to procedures described hereinbefore) was dissolved in ethyl acetate (5 mL). trans-D,L-1,2-Cyclopentanedicarboxylic acid (17.4 mg, 0.5 eq.) was dissolved in methanol and then added to the solution of Compound D. The solvents were evaporated, and then dissolved in the ethyl acetate. After a while a white precipitate was formed. The crystals were filtered. NMR-analysis showed that a 1:1 salt had been formed (~60 mg).

Figure 20:
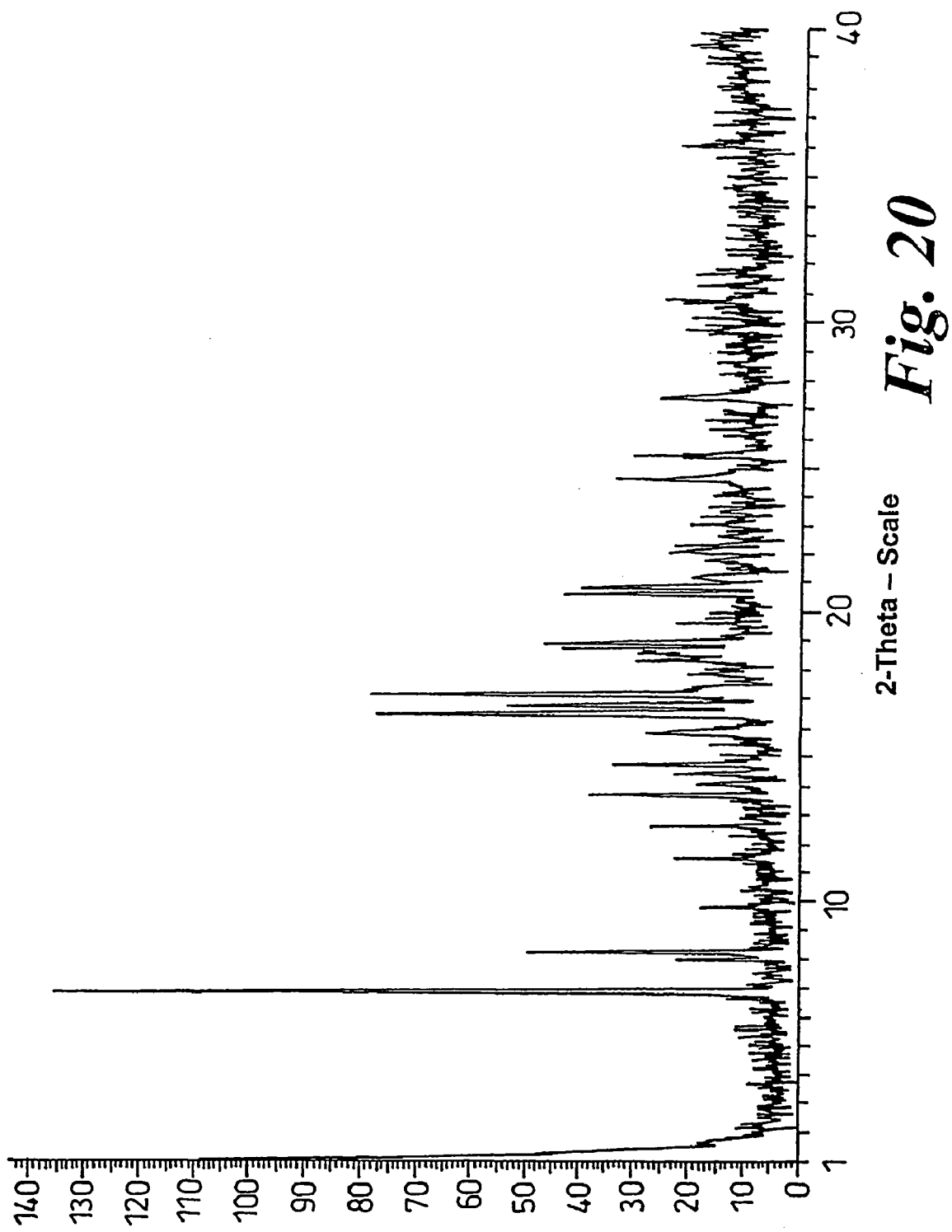
FIG. 20 shows an X-ray powder diffractogram for the crystalline form of Compound D, trans-D,L-1,2-cyclopentanedicarboxylic acid salt, obtained by way of Example 20.

The crystals were analyzed by XRPD and the results are tabulated below (Table 20) and are shown in FIG. 20.

TABLE 20

| d value (Å) | Intensity (%) |
|---|---|
| 12.9 | 100 |
| 11.1 | 14 |
| 10.7 | 35 |
| 9.0 | 10 |
| 7.7 | 14 |
| 7.0 | 15 |
| 6.5 | 18 |
| 6.3 | 10 |
| 6.1 | 14 |
| 6.0 | 21 |
| 5.6 | 17 |
| 5.4 | 55 |
| 5.3 | 37 |
| 5.2 | 55 |
| 4.73 | 29 |
| 4.68 | 32 |
| 4.31 | 29 |
| 4.26 | 26 |
| 4.02 | 13 |
| 3.86 | 12 |
| 3.61 | 22 |
| 3.50 | 19 |
| 3.24 | 16 |
| 2.90 | 15 |

EXAMPLE 21

Compound D, (+)-O,O'-dibenzoyl-D-tartaric acid salt

Compound D (100 mg; prepared analogously to procedures described hereinbefore) and 0.5 equivalents of (+)-O,O'-dibenzoyl-D-tartaric acid were mixed according to procedure described in Example 20 above. The salt was crystallised from ethyl acetate. NMR showed that a salt with a drug:acid ratio of 2:1 was formed in ~70% yield.

Figure 21:
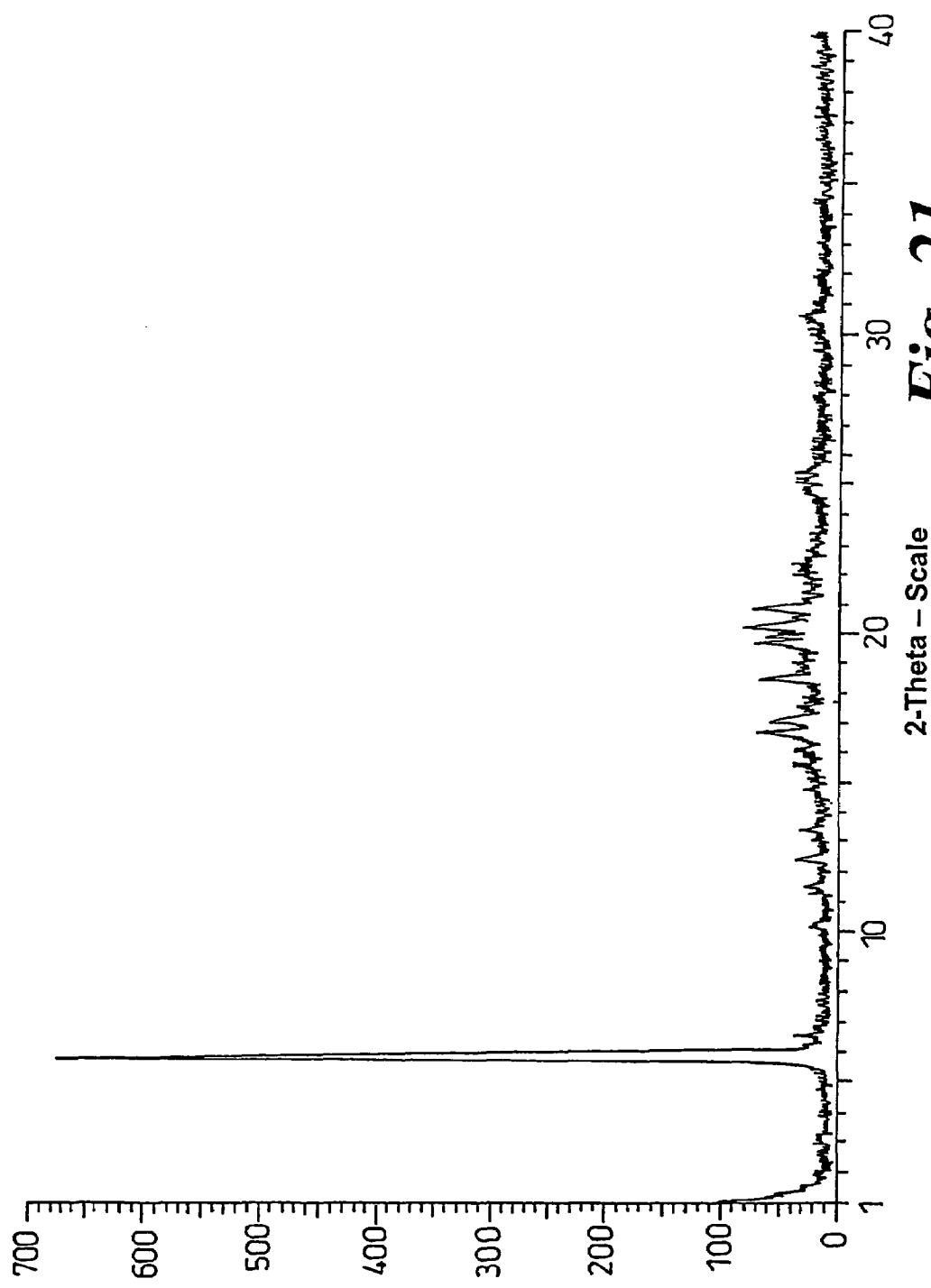
FIG. 21 shows an X-ray powder diffractogram for the crystalline form of Compound D, (+)-O,O'-dibenzoyl-D-tartaric acid salt, obtained by way of Example 21.

The crystals were analyzed by XRPD and the results are tabulated below (Table 21) and are shown in FIG. 21.

TABLE 21

| d value (Å) | Intensity (%) |
|---|---|
| 15.1 | 100 |
| 13.5 | 5 |
| 8.7 | 2 |
| 7.7 | 3 |
| 7.1 | 4 |
| 6.6 | 4 |
| 5.7 | 3 |
| 5.5 | 3 |
| 5.3 | 9 |
| 5.2 | 7 |
| 4.79 | 9 |
| 4.50 | 9 |
| 4.38 | 10 |
| 4.25 | 10 |
| 3.53 | 3 |
| 3.49 | 4 |
| 2.92 | 4 |

EXAMPLE 22

Compound D, (+)-O,O'-di-para-toluoyl-D-tartaric acid salt

Compound D (1.0 g; prepared analogously to procedures described hereinbefore) was dissolved in ethyl acetate (15 mL). (+)-O,O'-Di-para-toluoyl-D-tartaric acid (0.43 g) was dissolved in ethyl acetate (20 mL). The solutions were mixed. After a few minutes a white precipitate was formed. The mixture was stored at 4° C. overnight. The crystals were filtered off and dried under vacuum, yielding 1.1 g (76%) of a 2:1 salt (confirmed by NMR).

Figure 22:
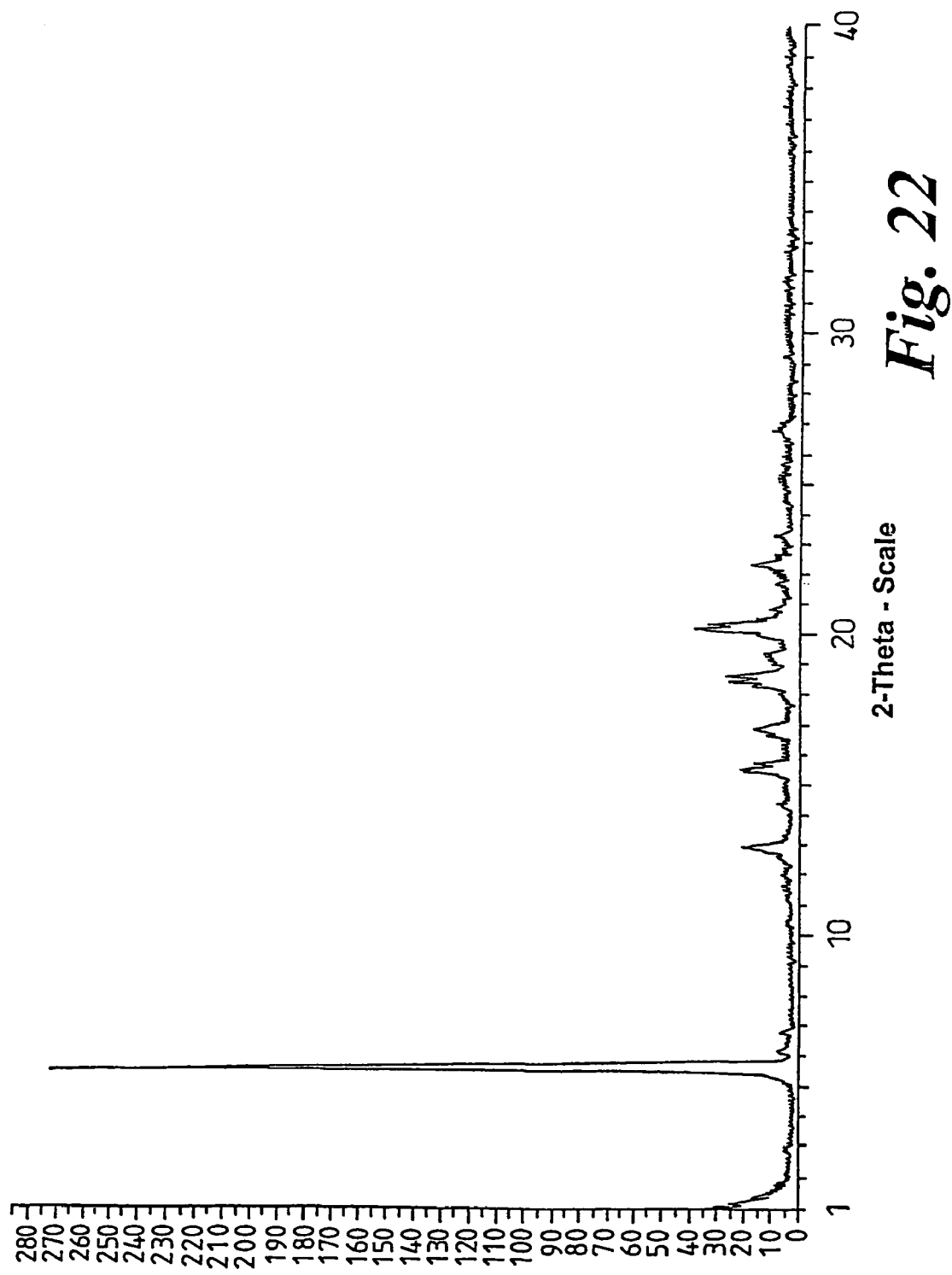
FIG. 22 shows an X-ray powder diffractogram for the crystalline form of Compound D, (+)-O,O'-di-para-toluoyl-D-tartaric acid salt, obtained by way of Example 22.

The crystals were analyzed by XRPD and the results are tabulated below (Table 22) and are shown in FIG. 22.

TABLE 22

| d value (Å) | Intensity (%) |
|---|---|
| 15.8 | 100 |
| 14.4 | 2 |
| 13.1 | 2 |
| 6.8 | 7 |
| 6.2 | 2 |
| 5.7 | 7 |
| 5.6 | 5 |
| 5.3 (5.32) | 3 |
| 5.3 (5.25) | 5 |
| 4.84 | 5 |
| 4.80 | 9 |
| 4.75 | 9 |
| 4.59 | 3 |
| 4.39 | 13 |
| 4.37 | 12 |
| 4.26 | 2 |
| 4.10 | 2 |
| 3.98 | 5 |
| 3.82 | 2 |
| 3.32 | 3 |
| 3.05 | 1 |

EXAMPLE 23

Crystallisation of Compound B

The crude material from Preparation B, Alternative II, step (iii), Method II was dissolved in iso-propanol (190 mL, 5.0 rel. vol.) at 60° C., and the hot solution was filtered. The filtrate was stirred, and left to cool to room temperature. A white solid crystallised. The mixture was cooled from room temperature to approximately 8° C. The product was collected by filtration and was washed with iso-propanol (50 mL, 2.0 vol.). The damp product was dried in vacuo at 40° C. to constant weight to give the title compound as a white crystalline solid (30.96 g, 81%).

m.p. 113.5° C. $^1$H-NMR (400 MHz, CD$_3$OD) δ 1.40 (9H, s), 1.81–1.90 (2H, m), 2.35–2.54 (8H, m), 2.93 (4H, t) 3.18–3.27 (4H, m), 3.87 (2H, bs), 6.66 (2H, d), 7.39 (2H, d) MS: m/z=(MH$^+$, 430)

ABBREVIATIONS

API=atmospheric pressure ionisation (in relation to MS)
br=broad (in relation to NMR)
d=doublet (in relation to NMR)
DCM=dichloromethane
DMF=N,N-dimethylformamide
DMSO=dimethylsulfoxide
dd=doublet of doublets (in relation to NMR)
Et=ethyl
eq.=equivalents
GC=gas chromatography
h=hour(s)
HCl=hydrochloric acid
HPLC=high performance liquid chromatography
IMS=industrial methylated spirit
IPA=iso-propyl alcohol
KF=Karl-Fischer
m=multiplet (in relation to NMR)
Me=methyl
MeCN=acetonitrile
min.=minute(s)
m.p.=melting point
MS=mass spectroscopy
Pd/C=palladium on carbon
q=quartet (in relation to NMR)
rt=room temperature
s=singlet (in relation to NMR)
t=triplet (in relation to NMR)
TLC=thin layer chromatography
UV=ultraviolet Prefixes n-, s-, i-, t- and tert- have their usual meanings: normal, secondary, iso, and tertiary.

The invention claimed is:

1. A pharmaceutically-acceptable salt of one of the following compounds:

4-({3-[7-(3,3-dimethyl-2-oxobutyl)-9-oxa-3,7-diazabicyclo[3.3.1]non-3-yl]-propyl}amino)benzonitrile;

tert-butyl 2-{7-[3-(4-cyanoanilino)propyl]-9-oxa-3,7-diazabicyclo[3.3.1]-non-3-yl}ethylcarbamate;

tert-butyl 2-{7-[4-(4-cyanophenyl)butyl]-9-oxa-3,7-diazabicyclo[3.3.1]-non-3-yl}ethylcarbamate; or tert-butyl 2-{7-[(2S)-3-(4-cyanophenoxy)-2-hydroxypropyl]-9-oxa-3,7-diazabicyclo[3.3.1]non-3-yl}ethylcarbamate, provided that the salt is not 4-({3-[7-(3,3-dimethyl-2-oxobutyl)-9-oxa-3,7-diazabicyclo[3.3.1]non-3-yl]propyl}amino)benzonitrile, benzenesulphonic acid salt.

2. 4-({3-[7-(3,3-Dimethyl-2-oxobutyl)-9-oxa-3,7-diazabicyclo[3.3.1]-non-3-yl]propyl}amino)benzonitrile; tert-butyl 2-{7-[3-(4-cyanoanilino)propyl]-9-oxa-3,7-diazabicyclo-[3.3.1]-non-3-yl}ethylcarbamate; tert-butyl 2-{7-[4-(4cyanophenyl)butyl]-9-oxa-3,7-diazabicyclo-[3.3.1]-non-3-yl}ethylcarbamate; or tert-butyl 2-}7-[(2S)-3-(4-cyanophenoxy)-2-hydroxypropyl]-9-oxa-3,7-di-azabicyclo[3.3.1]non-3-yl}ethylcarbamate, or a pharmaceutically-acceptable salt of any of those compounds, in greater than 20% crystalline form.

3. A compound as claimed in claim 2 which compound is 4-({3-[7-(3,3-dimethyl-2-oxobutyl)-9-oxa-3,7-diazabicyclo[3.3.1]non-3-yl]-propyl}-amino)benzonitrile.

4. A compound as claimed in claim 3 characterised by a differential scanning calorimetry curve, at a heating rate of 10° C./min in a closed cup with a pinhole under flowing nitrogen, exhibiting endotherms with extrapolated onset temperatures of about 121° C. and 126° C.; and/or an X-ray powder diffraction pattern characterised by peaks with d-values at 11.0, 7.8, 7.0, 5.7, 5.4, 5.1, 4.94, 4.71, 4.62, 4.54, 4.44, 4.34, 4.20, 3.92, 3.65, 3.51, 3.41, 3.34 and 2.89 Å, and/or at 11.0, 8.3, 7.8, 7.0, 6.7, 5.9, 5.7, 5.5, 5.4, 5.1, 4.94, 4.71, 4.62, 4.54, 4.44, 4.34, 4.20, 4.12, 3.92, 3.65, 3.51, 3.47, 3.41, 3.34, 3.31, 3.26, 3.04, 2.89, 2.82, 2.77, 2.70, 2.58, 2.44, 2.34, 2.18 and 2.06 Å and/or in FIG. 1, wherein the d-values vary in the range ±2 on the last decimal place.

5. A compound as claimed in claim 3 characterised by a differential scanning calorimetry curve, at a heating rate of 10° C./min in a closed cup with a pinhole under flowing nitrogen, exhibiting an endotherm with an extrapolated onset temperature of about 125° C.; and/or an X-ray powder diffraction pattern characterised by peaks with d-values at 10.9, 8.3, 7.8, 6.9, 6.7, 5.6 (5.64), 5.6 (5.56), 5.5, 5.4, 5.1, 5.0, 4.84, 4.78, 4.70, 4.49, 4.45, 4.36, 4.15, 4.10, 4.03, 3.97, 3.90, 3.80, 3.73, 3.47, 3.31, 2.95, 2.89, 2.85 and 2.80 Å, and/or at 10.9, 8.3, 7.8, 7.5, 7.0, 6.9, 6.8, 6.7, 6.4, 5.9, 5.64, 5.56, 5.5, 5.4, 5.3, 5.1, 5.0, 4.90, 4.84, 4.78, 4.70, 4.49, 4.45, 4.36, 4.25, 4.15, 4.10, 4.03, 3.97, 3.90, 3.80, 3.73, 3.60, 3.52, 3.47, 3.44, 3.39, 3.35, 3.31, 3.23, 3.13, 3.01, 2.95, 2.93, 2.89, 2.85, 2.80, 2.74, 2.69, 2.63 and 2.56 Å and/or in FIG. 2, wherein the d-values vary in the range ±2 on the last decimal place.

6. A compound as claimed in claim 3 characterised by a differential scanning calorimetry curve, at a heating rate of 10° C./min in a closed cup with a pinhole under flowing nitrogen, exhibiting an endotherm with an extrapolated onset temperature of about 122° C.; and/or an X-ray powder diffraction pattern characterised by peaks with devalues at 10.4, 9.6, 5.7, 5.3, 5.2, 4.83, 4.71, 4.55, 3.83, 3.58, 3.50, 3.29, 3.22 and 3.19 Å, and/or at 10.4, 9.6, 8.5, 7.0, 5.7, 5.3, 5.2, 4.83, 4.71, 4.55, 4.39, 3.96, 3.83, 3.58, 3.50, 3.43, 3.29, 3.22, 3.19, 3.12, 3.08, 2.99, 2.86, 2.66, 2.63, 2.55, 2.37, 2.31, 2.19, 2.13 and 2.10 Å and/or in FIG. 3, wherein the d-values vary in the range ±2 on the last decimal place.

7. A salt as claimed in claim 2 which salt is a 4-({3-[7-(3,3-dimethyl-2-oxobutyl)-9-oxa-3,7-diazabicyclo[3.3.1] non-3-yl]propyl}amino)benzonitrile, benzenesulphonic acid salt.

8. A salt as claimed in claim 7 characterised by an X-ray powder diffraction pattern characterised by peaks with d-values at 18.7, 9.4, 6.3, 4.69, 4.48, 3.76, 3.35, 3.13, 2.68, 2.35 and 1.88 Å, and/or at 18.7, 9.4, 7.5, 6.6, 6.4, 6.3, 5.1, 4.85, 4.77, 4.69, 4.63, 4.48, 4.40, 4.19, 4.13, 4.05, 3.92, 3.89, 3.76, 3.61, 3.35, 3.31, 3.21, 3.13, 3.07, 3.00, 2.68, 2.35, 2.31, 2.09, 2.00 and 1.88 Å and/or in FIG. 4, wherein the d-values vary in the range ±2 on the last decimal place.

9. A salt as claimed in claim 2 which salt is a 4-({3-[7-(3,3-dimethyl-2-oxobutyl)-9-oxa-3,7-diazabicyclo[3.3.1] non-3-yl]-propyl}-amino)benzonitrile, toluenesulphonic acid salt.

10. A salt as claimed in claim 9 characterised by a differential scanning calorimetry curve, at a heating rate of 10° C./min in a closed cup with a pinhole under flowing nitrogen, exhibiting an endotherm with an extrapolated onset temperature of about 145° C.; and/or an X-ray powder diffraction pattern characterised by peaks with d-values at 19.9, 10.0, 6.0, 4.99, 4.86, 4.38, 4.36, 4.19, 3.99 and 3.33 Å, and/or at 19.9, 10.0, 8.7, 7.6, 7.0, 6.6, 6.4, 6.0, 5.7, 5.5, 5.2, 4.99, 4.86, 4.49, 4.38, 4.36, 4.19, 3.99, 3.93, 3.77, 3.59, 3.40, 3.33, 3.29, 3.19, 3.08, 2.86, 2.22, 2.11, 2.09 and 2.00 Å and/or in FIG. 5(*a*), wherein the d-values vary in the range ±2 on the last decimal place.

11. A salt as claimed in claim 9 characterised by a differential scanning calorimetry curve, at a heating rate of 10° C. in a closed cup with a pinhole under flowing nitrogen, exhibiting an endotherm with an extrapolated onset temperature of about 153° C.; and/or an X-ray powder diffraction pattern characterised by peaks with d-values at 18.6, 9.3, 6.2, 4.66, 4.49, 3.73 and 3.11 Å, and/or at 18.6, 9.7, 9.3, 7.6, 6.2, 5.0, 4.66, 4.49, 3.73, 3.11 and 2.33 Å and/or in FIG. 5(*b*), wherein the d-values vary in the range ±2 on the last decimal place.

12. A salt as claimed in claim 2 which salt is a 4-({3-[7-(3,3-dimethyl-2-oxobutyl)-9-oxa-3,7-diazabicyclo[3.3.1] non-3-yl]-propyl}-amino)benzonitrile, hydroxynaphthoic acid salt.

13. A salt as claimed in claim 12 characterised by an X-ray powder diffraction pattern characterised by peaks with d-values at 17.6, 12.4, 8.8, 5.7, 5.6, 5.1, 4.95, 4.88, 4.47, 4.16, 4.08, 3.84, 3.80, 3.33 and 3.03 Å, and/or at 17.6, 12.4, 8.8, 7.9, 7.5, 6.6, 6.4, 6.2, 5.7, 5.6, 5.2, 5.1, 4.95, 4.88, 4.47, 4.40, 4.21, 4.16, 4.08, 3.95, 3.84, 3.80, 3.64, 3.55, 3.33, 3.03, 2.96 and 2.63 Å and/or in FIG. 6, wherein the d-values vary in the range ±2 on the last decimal place.

14. A salt as claimed in claim 2 which salt is a 4-({3-[7-(3,3-dimethyl-2-oxobutyl)-9-oxa-3,7-diazabicyclo[3.3.1] non-3-yl]-propyl}-amino)benzonitrile, naphthalenesulphonic acid salt.

15. A salt as claimed in claim 14 characterised by an X-ray powder diffraction pattern characterised by peaks with d-values at 16.1, 8.1, 7.1, 6.3, 6.0, 5.4 (5.39), 4.96, 4.88, 4.68, 4.49, 4.34, 4.10, 4.04, 3.94, 3.44, 3.40, 3.23, 3.20 and 3.15 Å, and/or at 16.1, 8.6, 8.1, 7.8, 7.1, 6.8, 6.3, 6.0, 5.5, 5.43, 5.39, 5.3, 4.96, 4.88, 4.68, 4.62, 4.49, 4.34, 4.10, 4.04, 3.94, 3.55, 3.44, 3.40, 3.23, 3.20, 3.15, 2.87, 2.72, 2.19 and 2.18 Å and/or in FIG. 7, wherein the d-values vary in the range ±2 on the last decimal place.

16. A salt as claimed in claim 2 which salt is a 4-({3-[7-(3,3-dimethyl-2-oxobutyl)-9-oxa-3,7-diazabicyclo[3.3.1] non-3-yl]-propyl}-amino)benzonitrile, mesitylenesulphonic acid salt.

17. A salt as claimed in claim 16 characterised by an X-ray powder diffraction pattern characterised by peaks with d-values at 18.8, 9.5, 6.3 (6.33), 6.3 (6.26), 4.75, 4.50, 4.46, 3.92, 3.80 and 3.17 Å, and/or at 18.9, 9.5, 8.8, 7.8, 6.33, 6.26, 5.7, 5.3, 5.1, 4.98, 4.75, 4.62, 4.50, 4.46, 4.41, 4.29, 4.24, 4.13, 3.92, 3.80, 3.69, 3.54, 3.36, 3.17, 3.04, 2.38 and 2.11 Å and/or in FIG. 8, wherein the d-values vary in the range ±2 on the last decimal place.

18. A compound as claimed in claim 2 which compound is tert-butyl 2-{7-[(2S)-3-(4-cyanophenoxy)-2-hydroxypropyl]-9-oxa-3,7-diazabicyclo-[3.3.1]non-3-yl}ethylcarbamate.

19. A compound as claimed in claim 18 characterised by a differential scanning calorimetry curve, at a heating rate of 10° C./min in a closed cup with a pinhole under flowing nitrogen, exhibiting an endotherm with an extrapolated onset temperature of about between 100 and 102° C. and/or an X-ray powder diffraction pattern characterised by peaks with d-values at 22.3, 11.2, 8.4, 7.1, 6.4, 5.8, 5.5, 5.2, 4.91, 4.81, 4.62, 4.52, 4.32, 4.22, 4.12, 4.06, 3.91, 3.81, 3.50, 3.34 and 3.15 Å, and/or at 22.3, 11.2, 8.4, 7.5, 7.1, 6.4, 5.8, 5.5, 5.2, 4.91, 4.81, 4.69, 4.62, 4.52, 4.32, 4.22, 4.12, 4.06, 3.91, 3.81, 3.72, 3.53, 3.50, 3.42, 3.34, 3.15, 3.03, 2.98, 2.92, 2.83, 2.77, 2.75, 2.67, 2.37 and 2.11 Å and/or in FIG. 9, wherein the d-values vary in the range ±2 on the last decimal place.

20. A salt as claimed in claim 2 which salt is a tert-butyl 2-{7-[(2S)-3-(4-cyanophenoxy)-2-hydroxypropyl]-9-oxa-3, 7-diazabicyclo-[3.3.1]non-3-yl}ethylcarbamate, methanesulphonic acid salt.

21. A salt as claimed in claim 20 characterised by a differential scanning calorimetry curve, at a heating rate of 10° C./min in a closed cup with a pinhole under flowing nitrogen, exhibiting an endotherm with an extrapolated onset temperature of about 167° C.; and/or an X-ray powder diffraction pattern characterised by peaks with d-values at 12.7, 9.4, 7.3, 7.1, 6.6, 6.0, 5.4, 5.1, 4.92, 4.83, 4.27, 4.14, 4.05, 3.99, 3.87, 3.73, 3.65, 3.42, 3.37 and 3.00 Å, and/or at 12.7, 9.4, 7.3, 7.1, 6.8, 6.6, 6.4, 6.0, 5.4, 5.1, 4.92, 4.83, 4.74, 4.66, 4.45, 4.27, 4.14, 4.05, 3.99, 3.87, 3.73, 3.65, 3.42, 3.37, 3.31, 3.22, 3.12, 3.00, 2.96, 2.92, 2.89, 2.81, 2.71, 2.63, 2.57, 2.50 and 2.41 Å and/or in FIG. 10, wherein the d-values vary in the range ±2 on the last decimal place.

22. A salt as claimed in claim 2 which salt is a tert-butyl 2-{7-[(2S)-3-(4-cyanophenoxy)-2-hydroxypropyl]-9-oxa-3, 7-diazabicyclo-[3.3.1]non-3-yl}ethylcarbamate, hippuric acid salt.

23. A salt as claimed in claim 22 characterised by an X-ray powder diffraction pattern characterised by peaks with d-values at 16.4, 6.9, 6.2, 6.1, 5.5, 5.2, 5.1, 4.93, 4.61, 4.50, 4.28, 4.20, 4.11 and 3.68 Å, and/or at 16.4, 13.8, 6.9, 6.2, 6.1, 5.6, 5.5, 5.2, 5.1, 4.93, 4.82, 4.61, 4.50, 4.28, 4.20, 4.11, 3.68, 3.54 and 3.27 Å and/or in FIG. 11, wherein the d-values vary in the range ±2 on the last decimal place.

24. A compound as claimed in claim 2 which compound is tert-butyl 2-{7-[4-(4-cyanophenyl)butyl]-9-oxa-3,7-diazabicyclo[3.3.1]non-3-yl}ethyl-carbamate.

25. A compound as claimed in claim 24 characterised by a differential scanning calorimetry curve, at a heating rate of 10° C./min in a closed cup with a pinhole under flowing nitrogen, exhibiting an endotherm with an extrapolated onset temperature of about 97° C.; and/or an X-ray powder diffraction pattern characterised by peaks with d-values at 19.4, 10.0, 9.1, 8.1, 6.5, 5.5, 5.2, 5.1, 4.99, 4.90, 4.46, 4.32, 4.06, 4.00, 3.85 and 3.80 Å, and/or at 19.4, 10.0, 9.1, 8.1, 6.5, 5.5, 5.2, 5.1, 4.99, 4.90, 4.60, 4.46, 4.32, 4.06, 4.00, 3.85, 3.80, 3.66, 3.56, 3.44, 3.33, 3.16, 2.94, 2.82, 2.69 and 2.44 Å and/or in FIG. 12, wherein the d-values vary in the range ±2 on the last decimal place.

26. A salt as claimed in claim 2 which salt is a tert-butyl 2-{7-[4-(4-cyanophenyl)butyl]-9-oxa-3,7-diazabicyclo[3.3.1]non-3-yl}ethyl-carbamate, methanesulphonic acid salt.

27. A salt as claimed in claim 26 characterised by a differential scanning calorimetry curve, at a heating rate of 10° C./min in a closed cup with a pinhole under flowing nitrogen, exhibiting endotherms with extrapolated onset temperatures of about 145° C. and 170° C.; and/or an X-ray powder diffraction pattern characterised by peaks with d-values at 13.3, 12.3, 9.6, 7.5, 6.9, 6.7, 5.5, 5.1, 5.0, 4.89, 4.81, 4.34, 4.23, 4.20, 4.08, 3.89, 3.85 and 3.80 Å, and/or at 13.3, 12.3, 9.6, 7.5, 6.9, 6.8, 6.7, 6.4, 6.2, 6.0, 5.5, 5.3, 5.1, 5.0, 4.89, 4.81, 4.34, 4.23, 4.20, 4.08, 3.99, 3.89, 3.85, 3.80, 3.68, 3.52, 3.49, 3.43, 3.39, 3.33, 3.25, 3.01, 2.94, 2.90, 2.80, 2.49 and 2.40 Å and/or in FIG. 13, wherein the d-values vary in the range ±2 on the last decimal place.

28. A salt as claimed in claim 2 which salt is a tert-butyl 2-{7-[4-(4-cyanophenyl)butyl]-9-oxa-3,7-diazabicyclo[3.3.1]non-3-yl}ethyl-carbamate, toluenesulphonic acid salt.

29. A salt as claimed in claim 28 characterised by a differential scanning calorimetry curve, at a heating rate of 10° C./min in a closed cup with a pinhole under flowing nitrogen, exhibiting an endotherm with an extrapolated onset temperature of about 138° C.; and/or an X-ray powder diffraction pattern characterised by peaks with d-values at 13.2, 7.1, 5.2, 5.0, 4.67, 4.28, 4.24, 4.19, 4.08, 3.36 and 3.12 Å, and/or at 13.2, 8.1, 7.5, 7.1, 6.6, 6.4, 6.3, 6.0, 5.6, 5.4, 5.2, 5.0, 4.97, 4.86, 4.67, 4.42, 4.28, 4.24, 4.19, 4.12, 4.08, 4.03, 4.01, 3.92, 3.82, 3.78, 3.66, 3.57, 3.46, 3.36, 3.32 and 3.12 Å and/or in FIG. 14, wherein the d-values vary in the range ±2 on the last decimal place.

30. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, [(biphenyl-4-carbonyl)amino]acetic acid salt.

31. A salt as claimed in claim 30 characterised by an X-ray powder diffraction pattern characterised by peaks with d-values at 20.4, 15.3, 11.5, 9.4, 7.7, 7.2, 5.9, 5.7, 5.4, 5.3, 5.2, 4.60, 4.54, 4.13, 3.85, 3.79, 3.64, 3.61, 3.40 and 2.94 Å, and/or at 20.4, 15.3, 11.5, 10.3, 10.0, 9.4, 7.7, 7.2, 6.2, 5.9, 5.7, 5.6, 5.4, 5.3, 5.2, 5.0, 4.89, 4.81, 4.70, 4.60, 4.54, 4.36, 4.22, 4.13, 4.06, 3.85, 3.79, 3.64, 3.61, 3.40, 3.31, 2.98, 2.94 and 2.88 Å and/or in FIG. 15, wherein the d-values vary in the range ±2 on the last decimal place.

32. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, hemisuccinic acid salt.

33. A salt as claimed in claim 32 characterised by an X-ray powder diffraction pattern characterised by peaks with d-values at 18.0, 8.3, 8.0, 7.5, 7.3, 6.8, 6.1, 5.8, 5.4, 4.89, 4.79, 4.68, 4.59, 4.54, 4.43, 4.35, 4.18, 4.04, 3.99, 3.90, 3.83, 3.67, 3.58, 3.07 and 2.47 Å, and/or at 35.4, 18.0, 12.1, 8.3, 8.0, 7.5, 7.3, 6.8, 6.1, 5.8, 5.4, 4.89, 4.79, 4.68, 4.59, 4.54, 4.43, 4.35, 4.18, 4.04, 3.99, 3.90, 3.83, 3.67, 3.58, 3.13, 3.07, 3.03, 2.47 and 2.44 Å and/or in FIG. 16, wherein the d-values vary in the range ±2 on the last decimal place.

34. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, (3,4-dichlorobenzoylamino)acetic acid salt.

35. A salt as claimed in claim 34 characterised by an X-ray powder diffraction pattern characterised by peaks with d-values at 16.6, 13.8, 10.9, 6.3, 6.2, 5.5, 5.3, 5.1, 5.0, 4.60, 4.33, 4.30, 4.22, 3.85, 3.70, 3.50, 3.30, 3.16, 3.06 and 2.99 Å, and/or at 16.6, 13.8, 10.9, 10.3, 6.3, 6.2, 5.5, 5.3, 5.1, 5.0, 4.60, 4.33, 4.30, 4.22, 4.11, 3.85, 3.70, 3.50, 3.30, 3.16, 3.06, 2.99 and 2.95 Å and/or in FIG. 17, wherein the d-values vary in the range ±2 on the last decimal place.

36. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, [(naphthalene-2-carbonyl)amino]acetic acid salt.

37. A salt as claimed in claim 36 characterised by an X-ray powder diffraction pattern characterised by peaks with d-values at 16.8, 6.2, 5.8, 5.6, 5.2, 5.1, 4.90, 4.76, 4.66, 4.53, 4.37, 4.31, 4.23, 4.08, 3.51, 3.25 and 3.12 Å, and/or at 16.8, 6.2, 5.8, 5.6, 5.2, 5.1, 4.90, 4.76, 4.66, 4.53, 4.37, 4.31, 4.23, 4.08, 3.70, 3.51, 3.25 and 3.12 Å and/or in FIG. 18, wherein the d-values vary in the range ±2 on the last decimal place.

38. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, 2,2,3,3,-tetramethyl-1,4-dibutanoic acid salt.

39. A salt as claimed in claim 38 characterised by an X-ray powder diffraction pattern characterised by peaks with d-values at 14.2, 10.3, 7.1, 6.4, 6.0, 5.6, 5.4, 5.1, 4.84, 4.77, 4.73, 4.66, 4.50, 422, 3.78, 3.62, 3.49, 3.35 and 3.09 Å, and/or at 14.2, 10.3, 7.1, 6.4, 6.0, 5.6, 5.4, 5.1, 4.84, 4.77, 4.73, 4.66, 4.50, 4.29, 4.22, 3.87, 3.78, 3.62, 3.49, 3.35, 3.09 and 2.75 Å and/or in FIG. 19, wherein the d-values vary in the range ±2 on the last decimal place.

40. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, 1,2-cyclopentanedicarboxylic acid salt.

41. A salt as claimed in claim 40 characterised by an X-ray powder diffraction pattern characterised by peaks with d-values at 12.9, 11.1, 10.7, 9.0, 7.7, 7.0, 6.5, 6.3, 6.1, 6.0, 5.6, 5.4, 5.3, 5.2, 4.73, 4.68, 4.31, 4.26, 4.02, 3.86, 3.61, 3.50, 3.24 and 2.90 Å, and/or at 12.9, 11.1, 10.7, 9.0, 7.7, 7.0, 6.5, 6.3, 6.1, 6.0, 5.6, 5.4, 5.3, 5.2, 4.73, 4.68, 4.31, 4.26, 4.02, 3.86, 3.61, 3.50, 3.24 and 2.90 Å and/or in FIG. 20, wherein the d-values vary in the range ±2 on the last decimal place.

42. A salt as claimed in claim 2 which salt is a tert-butyl 2-{7-[(2S)-3-(4-cyanophenoxy)-2-hydroxypropyl]-9-oxa-3,7-diazabicyclo-[3.3.1]non-3-yl}ethylcarbamate, O,O'-dibenzoyltartaric acid salt.

43. A salt as claimed in claim 42 characterised by an X-ray powder diffraction pattern characterised by peaks with d-values at 15.1, 13.5, 7.1, 6.6, 5.3, 5.2, 4.79, 4.50, 4.38, 4.25, 3.49 and 2.92 Å, and/or at 15.1, 13.5, 8.7, 7.7, 7.1, 6.6, 5.7, 5.5, 5.3, 5.2, 4.79, 4.50, 4.38, 4.25, 3.53, 3.49 and 2.92 Å and/or in FIG. 21, wherein the d-values vary in the range ±2 on the last decimal place.

44. A salt as claimed in claim 2 which salt is a tert-butyl 2-{7-[(2S)-3-(4-cyanophenoxy)-2-hydroxypropyl]-9-oxa-3, 7-diazabicyclo-[3.3.1]non-3-yl}ethylcarbamate, O,O'-di-para-toluoyltartaric acid salt.

45. A salt as claimed in claim 44 characterised by an X-ray powder diffraction pattern characterised by peaks with devalues at 15.8, 6.8, 5.7, 5.6, 5.3 (5.25), 4.84, 4.80, 4.75, 4.39, 4.37 and 3.98 Å, and/or at 15.8, 14.4, 13.1, 6.8, 6.2, 5.7, 5.6, 5.32, 5.25, 4.84, 4.80, 4.75, 4.59, 4.39, 4.37, 4.26, 4.10, 3.98, 3.82, 3.32 and 3.05 Å and/or in FIG. 22, wherein the d-values vary in the range ±2 on the last decimal place.

46. A process for the preparation of a salt as claimed in claim 2 comprising addition of an acid, or a base (as appropriate), to the appropriate free base compound.

47. A process as claimed in claim 46 wherein the process comprises addition of an acid to the appropriate free base compound.

48. A process for the preparation of a compound as claimed in claim 2 comprising crystallising the appropriate free base compound, or the appropriate pharmaceutically acceptable salt thereof.

49. A process as claimed in claim 48 which comprises crystallising the compound or salt from a solvent.

50. A process as claimed in claim 49 wherein the solvent is selected from the group: acetates, lower alkyl alcohols, aliphatic and aromatic hydrocarbons, dialkyl ethers, dialkyl ketones, acetonitrile, chlorinated alkanes, aqueous solvents, or mixtures thereof.

51. A process as claimed in claim 50 wherein the solvent is selected from the group: $C_{1-6}$ alkyl acetates, linear or branched $C_{1-6}$ alkyl alcohols, $C_{6-12}$ aliphatic hydrocarbons, $C_{6-10}$ aromatic hydrocarbons, di-$C_{1-6}$ alkyl ethers, di-$C_{1-6}$ alkyl ketones, chlorinated methanes or ethanes, acetonitrile, water, or mixtures thereof.

52. A process as claimed in claim 51 wherein the solvent is selected from the group: ethyl acetate, isopropyl acetate, methanol, ethanol, isopropanol, n-heptane, diethyl ether, acetone, dichloromethane, water, or mixtures thereof.

53. A process for the preparation of a salt as claimed in claim 2 comprising addition of an acid to the appropriate free base compound followed by crystallisation.

54. A process for the preparation of a crystalline form of 4-({3-[7-(3,3-dimethyl-2-oxobutyl)-9-oxa-3,7-diazabicyclo [3.3.1]non-3-yl]-propyl}-amino)benzonitrile; tert-butyl 2-{7-[3-(4-cyanoanilino)propyl]-9-oxa-3,7-diazabicyclo [3.3.1]non-3-yl}ethylcarbamate; tert-butyl 2-{7-[4-(4-cyanophenyl)butyl]-9-oxa-3,7-diazabicyclo [3.3.1]non-3-yl}ethyl-carbamate; or tert-butyl 2-{7-[(2S)-3-(4-cyanophenoxy)-2-hydroxypropyl]-9-oxa-3,7-diazabicyclo [3.3.1]non-3-yl}ethylcarbamate, or a pharmaceutically-acceptable salt of any of those compounds, which process comprises crystallising the relevant compound or salt from a solvent system comprising a combination of a $C_{3-7}$ alkyl alcohol and a di-$C_{3-5}$-alkyl ether.

55. A process as claimed in claim 54 wherein the ether is di-n-propyl ether, di-iso-propyl ether or di-n-butyl ether.

56. A process as claimed in claim 54 wherein the alcohol is n-propanol, iso-propanol, n-butanol, 4-methyl-2-pentanol, 3-methyl-1-butanol, 2-methyl-1-propanol or pentan-1-ol.

57. A process as claimed in claim 54 wherein the solvent combination is n-propanol and di-n-propyl ether, iso-propanol and di-iso-propyl ether; n-butanol and di-n-butyl ether; 4-methyl-2-pentanol and di-n-butyl ether; iso-propanol and di-n-butyl ether; 4-methyl-2-pentanol and di-iso-propyl ether, or pentan-1-ol and di-iso-propyl ether.

58. A process as claimed in claim 57 wherein the solvent combination is iso-propanol and di-iso-propyl ether.

59. A process as claimed in claim 54 wherein the compound is heated in the solvent combination to a temperature in the range 50 to 100° C.

60. A process as claimed in claim 54 wherein the compound to be crystallised is tert-butyl 2-{7-[(2S)-3-(4-cyanophenoxy)-2-hydroxypropyl]-9-oxa-3,7-diazabicyclo [3.3.1]non-3-yl}ethylcarbamate or a pharmaceutically-acceptable salt thereof.

61. A process as claimed in claim 60 wherein the compound is tert-butyl 2-{7-[(2S)-3-(4-cyanophenoxy)-2-hydroxypropyl]-9-oxa-3,7-di-azabicyclo[3.3.1]non-3-yl}ethylcarbamate.

62. A pharmaceutical formulation including a compound as defined in claim 1 in admixture with a pharmaceutically acceptable adjuvant, diluent or carrier.

63. A pharmaceutical formulation including a compound as defined in claim 2 in admixture with a pharmaceutically acceptable adjuvant, diluent or carrier.

64. A method of treatment of an arrhythmia which method comprises administration of a compound of claim 1 to a person suffering from such a condition.

65. The method as claimed in claim 64 wherein the arrhythmia is an atrial or a ventricular arrhythmia.

66. The method as claimed in claim 64 wherein the arrhythmia is atrial fibrillation.

67. The method as claimed in claim 64 wherein the arrhythmia is atrial flutter.

68. A method of treatment of an arrhythmia which method comprises administration of a compound of claim 2 to a person suffering from such a condition.

69. The method as claimed in claim 68 wherein the arrhythmia is an atrial or a ventricular arrhythmia.

70. The method as claimed in claim 68 wherein the arrhythmia is atrial fibrillation.

71. The method as claimed in claim 68 wherein the arrhythmia is atrial flutter.

* * * * *